US012522659B2

(12) United States Patent
Monseur et al.

(10) Patent No.: US 12,522,659 B2
(45) Date of Patent: Jan. 13, 2026

(54) ANTI-CD8 ALPHA DEPLETING ANTIBODIES

(71) Applicant: POLYGON THERAPEUTICS, Levallois-perret (FR)

(72) Inventors: Tatiana Monseur, Levallois-perret (FR); Mohamed Abou Ali, Levallois-perret (FR)

(73) Assignee: POLYGON THERAPEUTICS, Levallois-perret (FR)

( * ) Notice: Subject to any disclaimer, the term of this patent is extended or adjusted under 35 U.S.C. 154(b) by 0 days.

(21) Appl. No.: 19/209,867

(22) Filed: May 16, 2025

(65) Prior Publication Data

US 2025/0277036 A1 Sep. 4, 2025

Related U.S. Application Data

(63) Continuation of application No. PCT/EP2023/082168, filed on Nov. 17, 2023.

(30) Foreign Application Priority Data

Nov. 17, 2022 (EP) .................................... 22306689

(51) Int. Cl.

| | |
|---|---|
| ***C07K 16/28*** | (2006.01) |
| ***A61K 39/395*** | (2006.01) |
| ***A61P 9/10*** | (2006.01) |
| ***G01N 33/567*** | (2006.01) |
| *A61K 39/00* | (2006.01) |
| *C07K 14/705* | (2006.01) |

(52) U.S. Cl.

CPC ...... *C07K 16/2815* (2013.01); *A61K 39/3955* (2013.01); *A61P 9/10* (2018.01); *G01N 33/567* (2013.01); *A61K 2039/505* (2013.01); *C07K 14/70517* (2013.01); *C07K 2317/56* (2013.01); *C07K 2317/565* (2013.01); *G01N 2333/70517* (2013.01)

(58) Field of Classification Search

CPC .......... C07K 16/2815; C07K 14/70517; A61K 39/3955

See application file for complete search history.

(56) References Cited

FOREIGN PATENT DOCUMENTS

| | | |
|---|---|---|
| CN | 110237250 A | 9/2019 |
| WO | 2022185081 A1 | 9/2022 |

OTHER PUBLICATIONS

Search Report issued on Apr. 4, 2023, in corresponding European Application No. 22306689.5, 5 pages.
International Search Report issued on May 4, 2024, in corresponding International Application No. PCT/EP2023/082168, 7 pages.
Barry et al., "Depletion of CD8+ Cells in Sooty Mangabey Monkeys Naturally Infected with Simian Immunodeficiency Virus Reveals Limited Role for Immune Control of Virus Replication in a Natural Host Species", The Journal of Immunology, The American Association of Immunologists, Jun. 15, 2007, vol. 178, No. 12, pp. 8002-8012.
Schmitz et al., "A Nonhuman Primate Model for the Selective Elimination of CD8+ Lymphocytes Using a Mouse-Human Chimeric Monoclonal Antibody", Animal Model, American Journal of Pathology, American Society for Investigative Pathology, Jun. 1999, vol. 154, No. 6, pp. 1923-1932.
Rudikoff et al., "Single Amino Acid Substitution Altering Antigen-Binding Specificity", Proc. Natl. Acad. Sci., Immunology, Mar. 1982, vol. 79, No. 6, pp. 1979-1983.
Winkler et al., "Changing the Antigen Binding Specificity by Single Point Mutations of an Anti-P24 (HIV-1) Antibody", The Journal of Immunology, The American Association of Immunologists, Oct. 15, 2000, vol. 165, No. 8, pp. 4505-4514.
Laface et al., "Human CD8 Transgene Regulation of HLA Recognition by Murine T Cells", J. Exp Med., The Rockefeller University Press, Nov. 1, 1995, vol. 182, No. 5, pp. 1315-1325.
Zouggari et al., "B Lymphocytes Trigger Monocyte Mobilization and Impair Heart Function After Acute Myocardial Infarction", Nature Medicine, Author Manuscript, Nature America, Inc., Oct. 2013, vol. 19 No. 10, 22 pages.

*Primary Examiner* — Zachary C Howard
(74) *Attorney, Agent, or Firm* — Maier & Maier, PLLC

(57) ABSTRACT

Novel anti-CD8α (cluster of differentiation 8 alpha) antibodies and antigen-binding fragments thereof, a fusion protein including the anti-CD8α antibodies and antigen-binding fragments thereof, and a nucleic acid molecule encoding the anti-CD8α antibodies and antigen-binding fragments thereof. Also, pharmaceutical compositions including the anti-CD8α antibodies and antigen-binding fragments thereof. Further, methods using the anti-CD8α antibodies and antigen-binding fragments thereof for treating CD8-related diseases and in vitro methods in which CD8a-expressing cells are depleted in a sample or in which CD8α is detected or quantified in a sample.

13 Claims, 11 Drawing Sheets

Specification includes a Sequence Listing.

Rat IgG2b antibody clones

HPB-ALL cells hMP08-R3-F08 hMP08-R3-C11 hMP09-R3-D03

Irrelevant IgG1

Commercial anti-CD8α antibody 1299 cells hMP08-R3-F08 hMP08-R3-C11 hMP09-R3-D03

Irrelevant IgG1

Commercial anti-CD8α antibody

Primary CD8+ T cells

ANTI-CD8 ALPHA DEPLETING ANTIBODIES

REFERENCE TO RELATED APPLICATIONS

This application is a continuation of International Patent Application No. PCT/EP2023/082168, filed on Nov. 17, 2023, which claims the benefit of EP 22306689.5, filed Nov. 22, 2022, each of which is incorporated by reference herein in its entirety.

REFERENCE TO A SEQUENCE LISTING

In accordance with 37 CFR § 1.831, the present specification makes reference to a Sequence Listing submitted electronically as a .xml file named "2490 PCT—Sequence listing.xml". The .xml file was generated on Oct. 4, 2023 and is 45,256 bytes in size. The entire contents of the Sequence Listing are hereby incorporated by reference.

FIELD

The present invention relates to anti-CD8α (cluster of differentiation 8 alpha) antibodies and antigen-binding fragments thereof.

BACKGROUND

CD8α (cluster of differentiation 8 alpha) is a glycoprotein, member of the immunoglobulin superfamily. CD8α either homodimerizes with another CD8α protein, or heterodimerizes with a CD8β (cluster of differentiation 8 beta) protein to form the dimeric CD8 molecule expressed at the surface of CD8+ cytotoxic T cells. On CD8+ T cells, the dimeric CD8 molecule serves as a co-receptor for the T-cell receptor (TCR) to recognize antigens displayed by an antigen presenting cell in the context of class I MHC molecules. Therefore, the dimeric CD8 molecule plays a role of interaction reinforcement between the T cell and the antigen-presenting cell.

Both CD8α and CD8β proteins are constituted of an immunoglobulin-like extracellular domain, and of a long glycosylated peptide chain which serves both as transmembrane and intracellular domains. Thus, the dimeric CD8 molecule is also important for transmitting signals to the T cell through its intracellular domain which recruits the tyrosine kinase $p56^{lck}$, important for the phosphorylation cascade taking place after antigen recognition.

CD8+ cytotoxic T cells have been shown to mediate the clearance of cancer cells, cells infected by intracellular pathogens (such as viruses or bacteria), as well as damaged cells. When exposed to infected or dysfunctional cells, CD8+ cytotoxic T cells express death-inducing ligands, and they also release cytotoxins such as perforin, granzymes, and granulysin, which will induce the apoptosis or lysis of the target cells. Therefore, CD8+ cytotoxic T cells play an important role in the immune response and the fight against intracellular pathogens and tumor cells.

However, CD8+ cytotoxic T cells have also been involved in the development of various diseases and disorders, and it may thus be advantageous in certain circumstances to be able to deplete CD8+ cytotoxic T cells in a controlled manner. Therefore, there is a need for a new therapeutic tool specifically targeting CD8+ cytotoxic T cells that would allow to transiently deplete CD8+ cytotoxic T cells in a controlled manner.

Consequently, the Inventors herein aimed at developing novel antibodies that specifically bind CD8α and allow the depletion of CD8α-expressing cells, mainly CD8+ cytotoxic T cells. Advantageously, the anti-CD8α antibodies as described herein are capable of inducing a fast and almost complete depletion of CD8α-expressing cells, followed by a controlled repopulation of CD8α-expressing cells. Thus, the anti-CD8α antibodies as described herein would make a valuable therapeutic tool for transiently depleting CD8α-expressing cells.

SUMMARY

The present invention relates to an isolated anti-CD8α antibody, or an antigen-binding fragment thereof, wherein:

a) the variable region of the heavy chain (VH) of said isolated anti-CD8α antibody, or antigen-binding fragment thereof, comprises the three following CDRs:
  - $V_H$-CDR1: $NX_1X_2MN$, wherein
    - $X_1$ is N or Y,
    - $X_2$ is D or A or Y,
  - $V_H$-CDR2: $X_3ISGSSX_4YIX_5YADFVKG$ (SEQ ID NO: 1), wherein
    - $X_3$ is D or S,
    - $X_4$ is S or R,
    - $X_5$ is D or G or Y,
  - $V_H$-CDR3: $SSX_6X_7X_8X_9YX_{10}X_{11}X_{12}X_{13}MDV$ (SEQ ID NO: 2), wherein
    - $X_6$ is N or no amino acid,
    - $X_7$ is Y or no amino acid,
    - $X_8$ is Y or G or no amino acid,
    - $X_9$ is D or S or no amino acid,
    - $X_{10}$ is S or N or F,
    - $X_{11}$ is A or G,
    - $X_{12}$ is S or D or N,
    - $X_{13}$ is A or G; and b) the variable region of the light chain (VL) of said isolated anti-CD8α antibody, or antigen-binding fragment thereof, comprises the three following CDRs:
  - VL-CDR1: $AGTSSDVGGX_{14}X_{15}X_{16}VS$ (SEQ ID NO: 3), wherein
    - $X_{14}$ is G or N or Y,
    - $X_{15}$ is S or Y,
    - $X_{16}$ is S or Y,
  - $V_L$-CDR2: $X_{17}DSX_{18}RPS$ (SEQ ID NO: 4), wherein
    - $X_{17}$ is Q or S or Y,
    - $X_{18}$ is Y or S,
  - VL-CDR3: $SSX_{19}TX_{20}YSTRV$ (SEQ ID NO: 5), wherein
    - $X_{19}$ is Y or D,
    - $X_{20}$ is Y or Q or S.

In some embodiments, the isolated anti-CD8α antibody, or antigen-binding fragment thereof, comprises:

```
a) a VH comprising the three following CDRs:
VH-CDR1:
                                    (SEQ ID NO: 6)
NNAMN,

                                   (SEQ ID NO: 12)
NYDMN,
or

                                   (SEQ ID NO: 18)
NYYMN;

VH-CDR2:
                                    (SEQ ID NO: 7)
DISGSSRYIGYADFVKG,
```

-continued (SEQ ID NO: 13)
DISGSSSYIDYADFVKG,
or (SEQ ID NO: 19)
SISGSSRYIYYADFVKG;

$V_H$-CDR3:
(SEQ ID NO: 8)
SSNYYDYNADAMDV, (SEQ ID NO: 14)
SSYYSGSGMDV,
or (SEQ ID NO: 20)
SSGSYFGNAMDV;
and b) a VL comprising the three following CDRs:
$V_L$-CDR1:
(SEQ ID NO: 9)
AGTSSDVGGNSYVS, (SEQ ID NO: 15)
AGTSSDVGGGSSVS,
or (SEQ ID NO: 21)
AGTSSDVGGYYSVS;

$V_L$-CDR2:
(SEQ ID NO: 10)
SDSSRPS, (SEQ ID NO: 16)
QDSYRPS,
or (SEQ ID NO: 22)
YDSSRPS $V_L$-CDR3:
(SEQ ID NO: 11)
SSYTQYSTRV, (SEQ ID NO: 17)
SSYTYYSTRV,
or (SEQ ID NO: 23)
SSDTSYSTRV.

In some embodiments, the isolated anti-CD8α antibody, or antigen-binding fragment thereof, comprises the six following CDRs:

$V_H$-CDR1:
(SEQ ID NO: 6)
NNAMN, $V_H$-CDR2:
(SEQ ID NO: 7)
DISGSSRYIGYADFVKG, $V_H$-CDR3:
(SEQ ID NO: 8)
SSNYYDYNADAMDV, $V_L$-CDR1:
(SEQ ID NO: 9)
AGTSSDVGGNSYVS,

VL-CDR2:
(SEQ ID NO: 10)
SDSSRPS,
and

-continued $V_L$-CDR3:
(SEQ ID NO: 11)
SSYTQYSTRV;
or $V_H$-CDR1:
(SEQ ID NO: 12)
NYDMN, $V_H$-CDR2:
(SEQ ID NO: 13)
DISGSSSYIDYADFVKG, $V_H$-CDR3:
(SEQ ID NO: 14)
SSYYSGSGMDV, $V_L$-CDR1:
(SEQ ID NO: 15)
AGTSSDVGGGSSVS, $V_L$-CDR2:
(SEQ ID NO: 16)
QDSYRPS,
and $V_L$-CDR3:
(SEQ ID NO: 17)
SSYTYYSTRV;
or $V_H$-CDR1:
(SEQ ID NO: 18)
NYYMN, $V_H$-CDR2:
(SEQ ID NO: 19)
SISGSSRYIYYADFVKG, $V_H$-CDR3:
(SEQ ID NO: 20)
SSGSYFGNAMDV, $V_L$-CDR1:
(SEQ ID NO: 21)
AGTSSDVGGYYSVS, $V_L$-CDR2:
(SEQ ID NO: 22)
YDSSRPS,
and $V_L$-CDR3:
(SEQ ID NO: 23)
SSDTSYSTRV.

In some embodiments, the isolated anti-CD8α antibody, or antigen-binding fragment thereof, comprises a variable region of the heavy chain (VH) comprising a sequence as set forth in SEQ ID NO: 24, SEQ ID NO: 26, or SEQ ID NO: 28, or a sequence having at least 80% identity with SEQ ID NO: 24, SEQ ID NO: 26, or SEQ ID NO: 28. In some embodiments, the isolated anti-CD8α antibody, or antigen-binding fragment thereof, comprises a variable region of the light chain (VL) comprising a sequence as set forth in SEQ ID NO: 25, SEQ ID NO: 27, or SEQ ID NO: 29, or a sequence having at least 80% identity with SEQ ID NO: 25, SEQ ID NO: 27, or SEQ ID NO: 29.

In some embodiments, the isolated anti-CD8α antibody, or antigen-binding fragment thereof, comprises:

- a VH comprising a sequence as set forth in SEQ ID NO: 24, or a sequence having at least 80% identity with SEQ ID NO: 24, and a VL comprising a sequence as set forth in SEQ ID NO: 25, or a sequence having at least 80% identity with SEQ ID NO: 25; or
- a VH comprising a sequence as set forth in SEQ ID NO: 26, or a sequence having at least 80% identity with SEQ ID NO: 26, and a VL comprising a sequence as set forth in SEQ ID NO: 27, or a sequence having at least 80% identity with SEQ ID NO: 27; or a VH comprising a sequence as set forth in SEQ ID NO: 28, or a sequence having at least 80% identity with SEQ ID NO: 28, and a VL comprising a sequence as set forth in SEQ ID NO: 29, or a sequence having at least 80% identity with SEQ ID NO: 29.

In some embodiments, the isolated anti-CD8α antibody, or antigen-binding fragment thereof, is a CD8α-expressing cell depleting antibody.

The present invention also relates to a fusion protein comprising said anti-CD8α antibody, or antigen-binding fragment thereof; and to a nucleic acid molecule encoding said anti-CD8α antibody, or antigen-binding fragment thereof, or said fusion protein.

The present invention also relates to a pharmaceutical composition comprising said isolated anti-CD8α antibody, or antigen-binding fragment thereof, said fusion protein, and/or said nucleic acid molecule, and at least one pharmaceutically acceptable excipient.

The present invention also relates to said isolated anti-CD8α antibody, or antigen-binding fragment thereof, said fusion protein, said nucleic acid molecule, or said pharmaceutical composition, for use as a medicament.

The present invention also relates to said isolated anti-CD8α antibody, or antigen-binding fragment thereof, said fusion protein, said nucleic acid molecule, or said pharmaceutical composition, for use in the treatment of a CD8-related disease. In some embodiments, the CD8-related disease is a cardiovascular disease.

The present invention also relates an in vitro method for depleting CD8α-expressing cells in a sample, comprising a step of contacting said sample with the isolated anti-CD8α antibody, or antigen-binding fragment thereof, as described herein, or with the fusion protein as described herein. The present invention also relates to an in vitro method for detecting and/or quantifying CD8α in a sample, cell, tissue or organ, comprising contacting said sample, cell, tissue or organ with the isolated anti-CD8α antibody, or antigen-binding fragment thereof, as described herein, or with the fusion protein as described herein.

3A represents MP08-R3-F08 human IgG1 clone.

3B represents MP08-R3-C11 human IgG1 clone.

3C represents MP09-R3-D03 human IgG1 clone.

3D represents irrelevant human IgG1 13R4 antibody control.

3E represents a commercial mouse anti-human CD8α antibody.

FIG. 4A-E is a combination of flow cytometry plots showing the binding of the 3 antibody clones (i.e., MP08-R3-F08, MP08-R3-C11 and MP09-R3-D03) in the human IgG1 format onto CD8− cells (H1299 cells). Irrelevant human IgG1 13R4 antibody was used as a negative control and a commercial mouse anti-human CD8α antibody was used as a positive control. Antibodies were used at a concentration of 3.3 μg/mL. Light grey represents cells alone (background signal), darker grey represents cells with one of the antibodies as indicated (binding signal).

4A represents MP08-R3-F08 human IgG1 clone.

4B represents MP08-R3-C11 human IgG1 clone.

4C represents MP09-R3-D03 human IgG1 clone.

4D represents irrelevant human IgG1 13R4 antibody control.

4E represents a commercial mouse anti-human CD8α antibody.

FIG. 5A-E is a combination of flow cytometry plots showing the binding of the 3 antibody clones (i.e., MP08-R3-F08, MP08-R3-C11 and MP09-R3-D03) in the human IgG1 format onto human primary CD8+ T cells. Irrelevant human IgG1 13R4 antibody was used as a negative control and a commercial mouse anti-human CD8α antibody was used as a positive control. Antibodies were used at a concentration of 1.1 μg/mL. Light grey represents cells alone (background signal), darker grey represents cells with one of the antibodies as indicated (binding signal).

5A represents MP08-R3-F08 human IgG1 clone.

5B represents MP08-R3-C11 human IgG1 clone.

5C represents MP09-R3-D03 human IgG1 clone.

5D represents irrelevant human IgG1 13R4 antibody control.

5E represents a commercial mouse anti-human CD8α antibody.

Figure 6A:
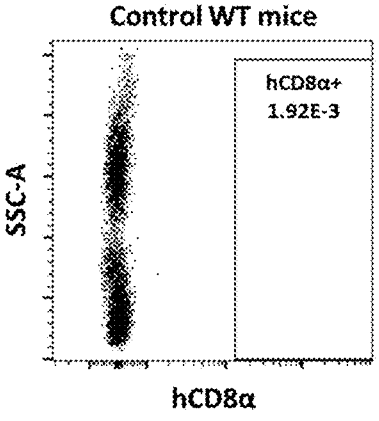
Figure 6B:
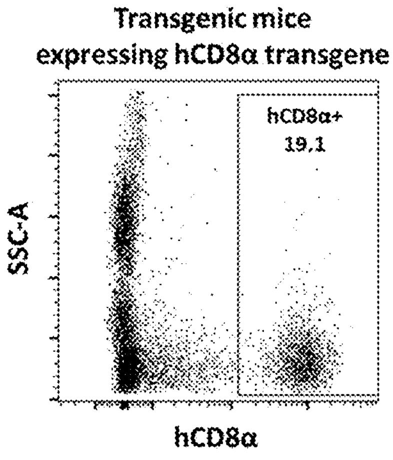

FIG. 6A-B is a combination of flow cytometry plots showing the percentage of cells expressing the human CD8α transgene from CD45+ cells in control WT mice (6A) and transgenic mice expressing the human CD8α transgene (6B).

Figure 7A:
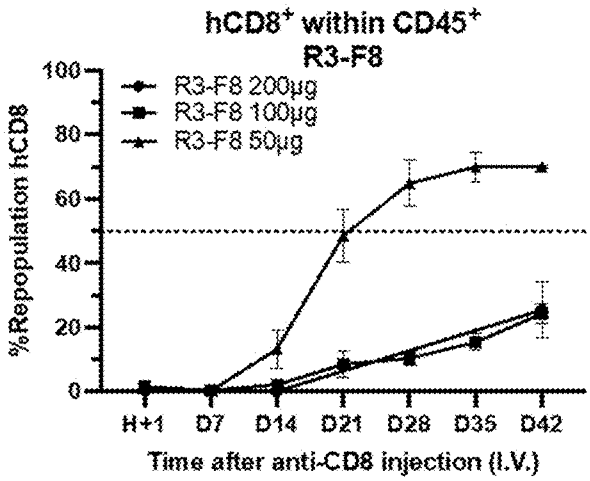
Figure 7B:
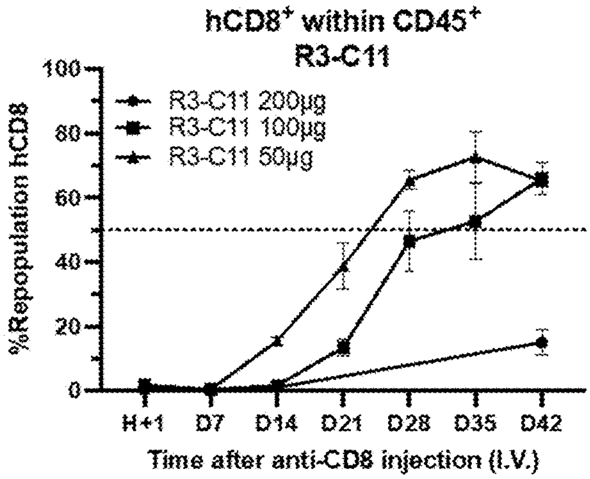
Figure 7C:
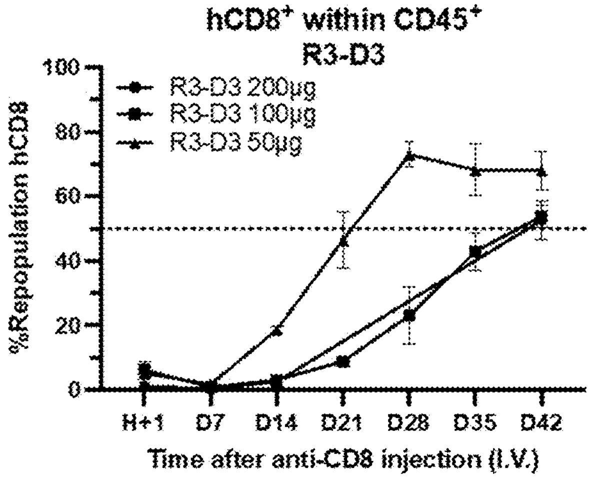

FIG. 7A-C is a combination of graphs showing the depletion and subsequent repopulation of human CD8α-expressing cells in mice after injection with antibody MP08-R3-F08 (7A), MP08-R3-C11 (7B) or MP09-R3-D03 (7C) at a dose of 50 μg, 100 μg or 200 μg as indicated.

Figure 8A:
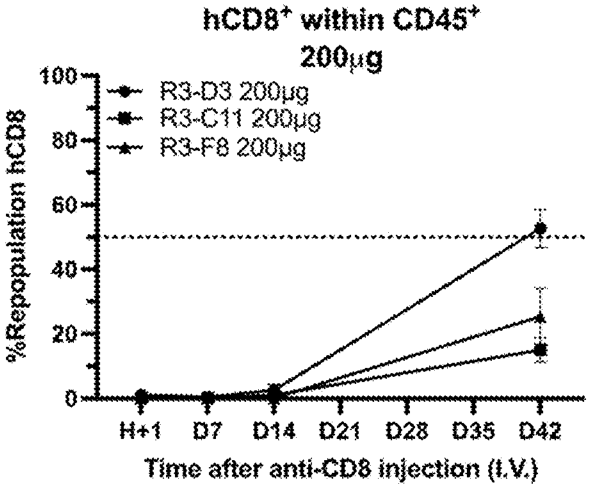
Figure 8B:
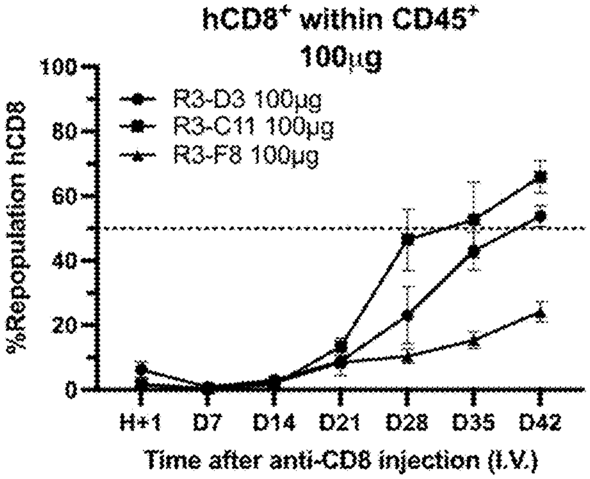
Figure 8C:
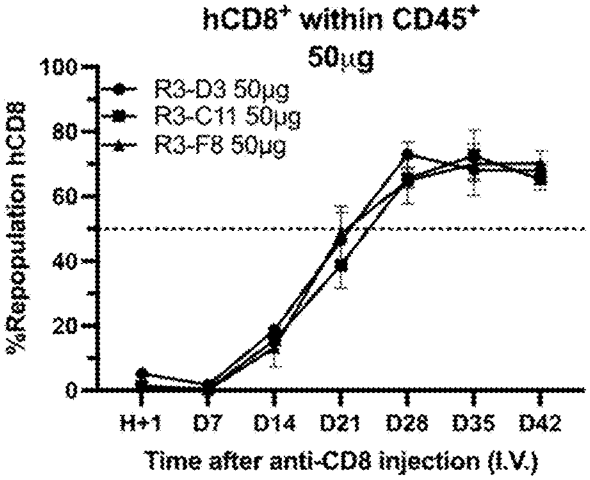
Figure 9A:
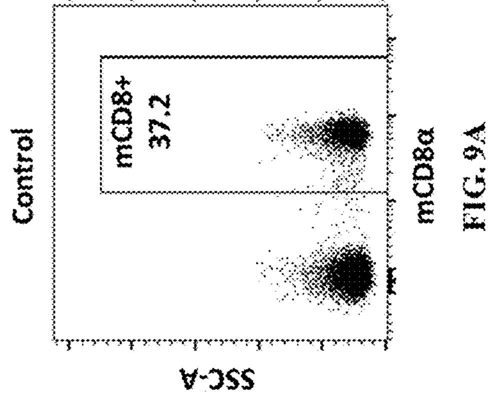
Figure 9B:
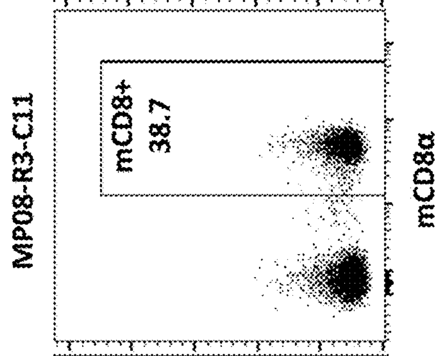
Figure 9C:
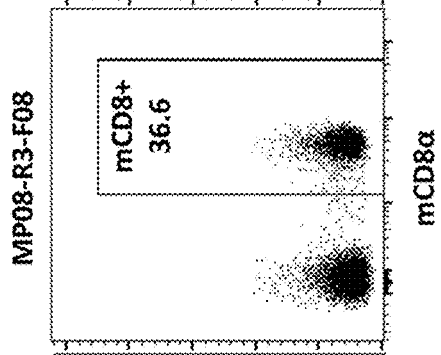
Figure 9D:
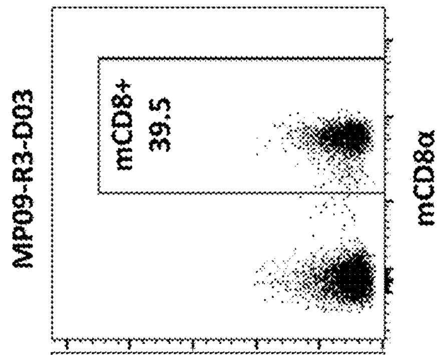
Figure 9E:
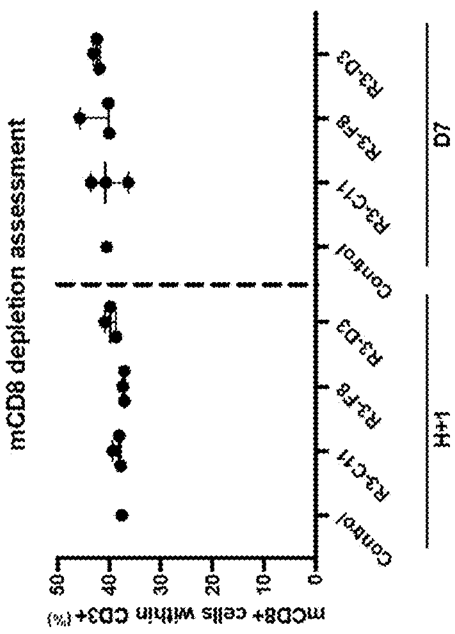

FIG. 8A-C is a combination of histograms showing the depletion and subsequent repopulation of human CD8α-expressing cells in mice after injection with a dose of 200 μg (8A), 100 μg (8B) or 50 μg (8C) of antibody MP08-R3-F08, MP08-R3-C11 or MP09-R3-D03 as indicated.

FIG. 9A-E is a combination of flow cytometry plots showing the percentage of mouse CD8α+ cells in control C56B16 mice after injection with a control IgG1 isotype antibody (9A), MP08-R3-C11 (9B), MP08-R3-F08 (9C) or MP09-R3-D03 (9D) and of a histogram showing the quantification 1 hour and 7 days after injection (9E).

Figure 10A:
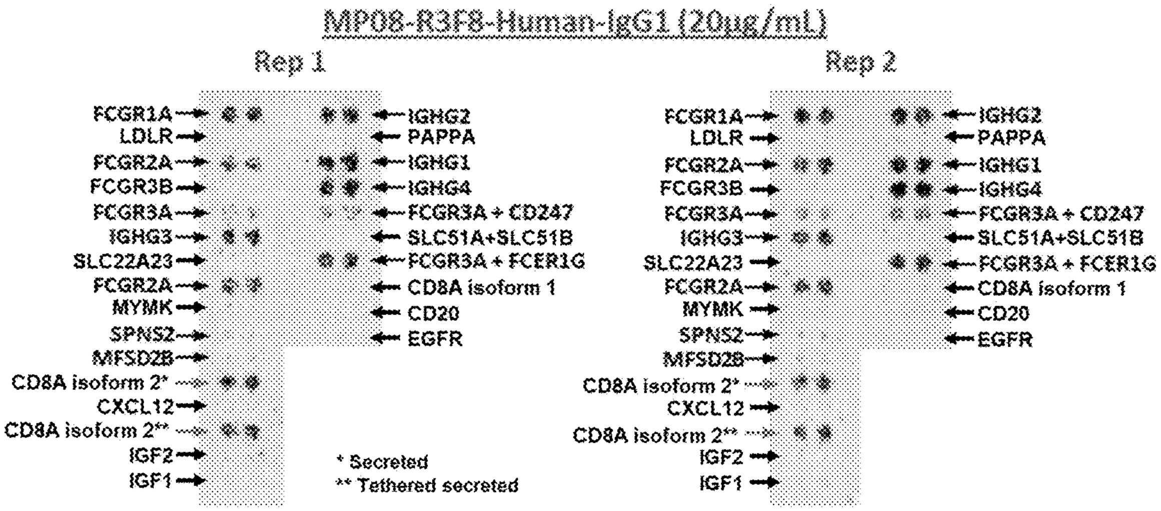
Figure 10B:
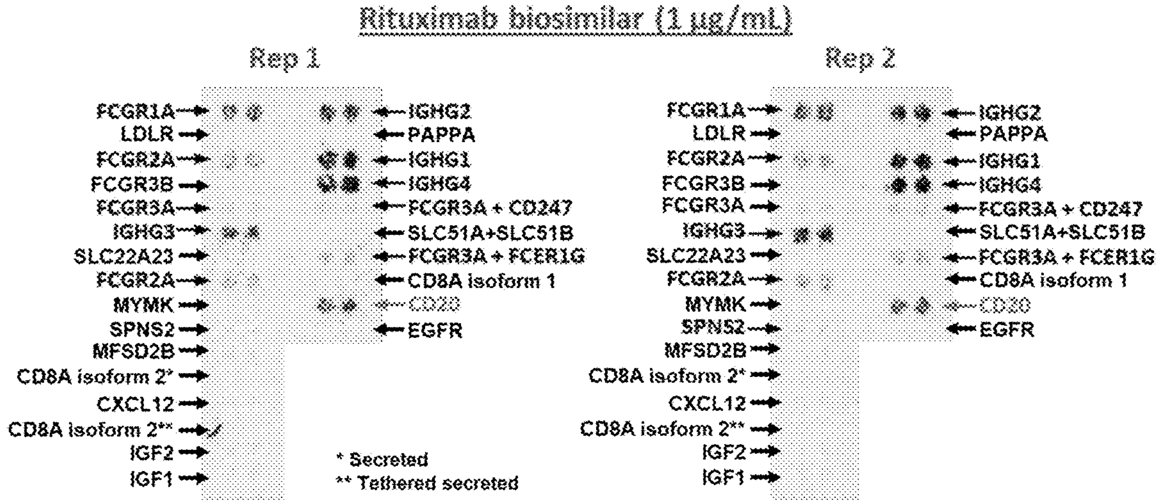
Figure 10C:
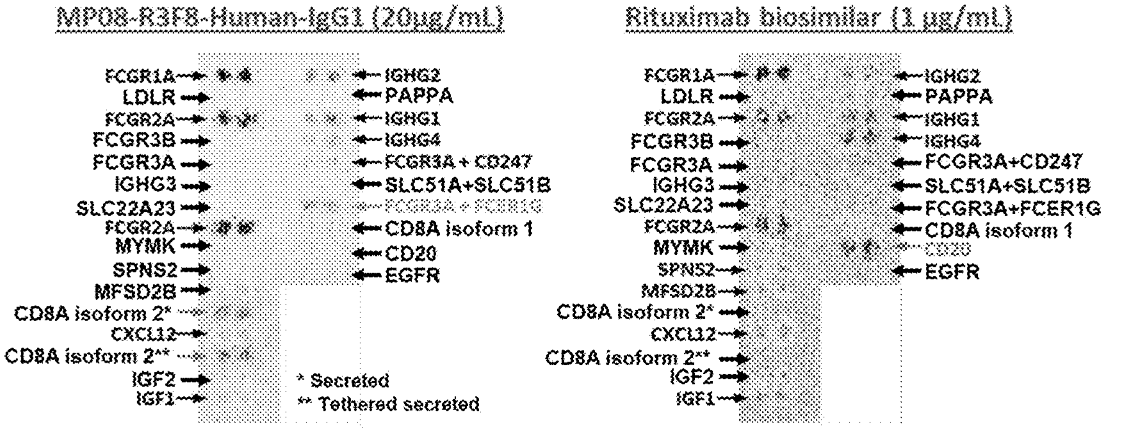

FIG. 10A-C is a combination of fluorescent images showing the confirmation screen on fixed cells (10A-B) and on non-fixed cells (10C) for anti-CD8α antibody clone MP08-R3-F08 (10A & C) and control antibody Rituximab (10B & C). Each spot corresponds to cells transfected with an expression vector expressing proteins as indicated.

Figure 11A:
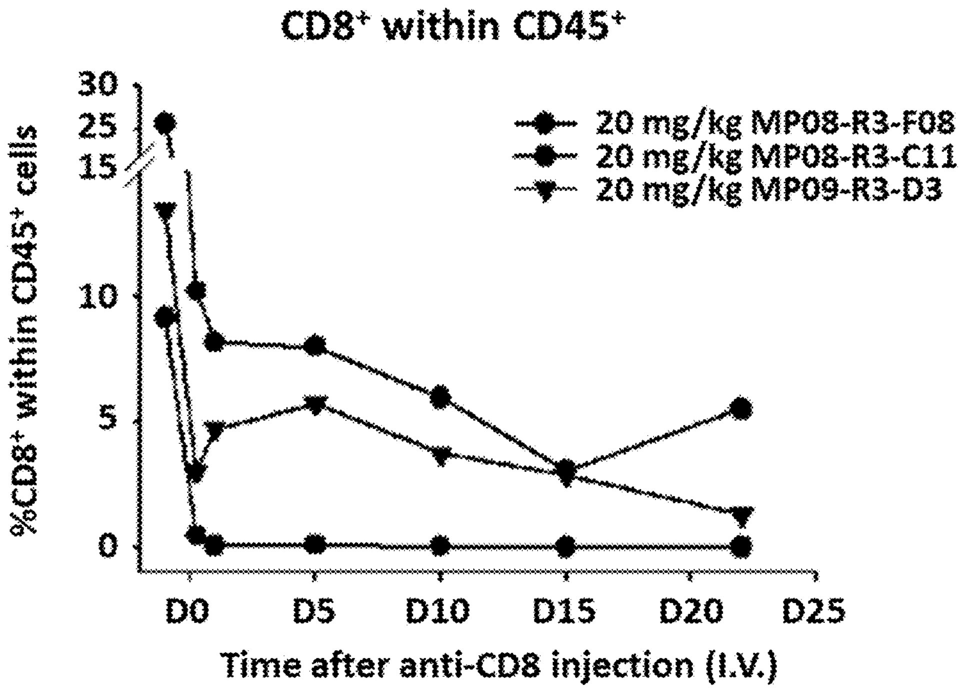
Figure 11B:
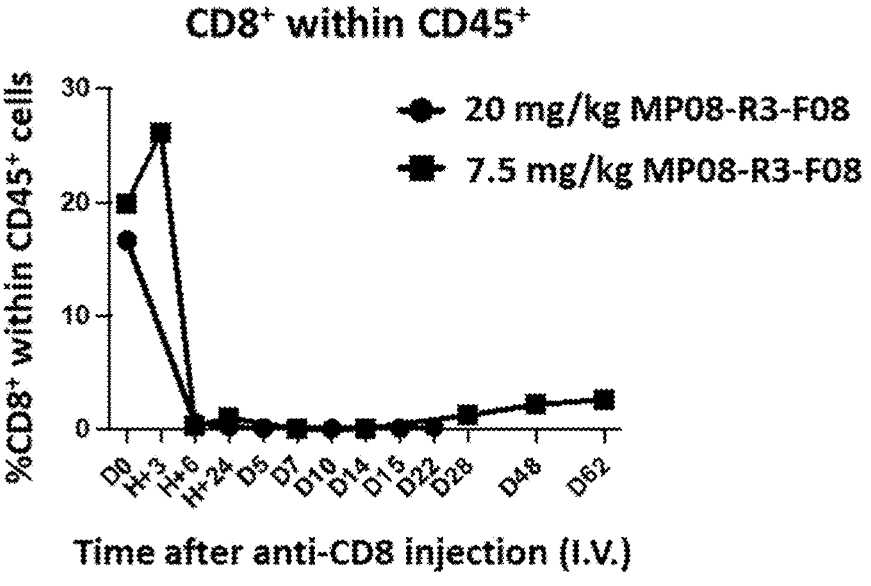

FIG. 11A-B is a combination of histograms showing the depletion of CD8α-expressing cells in Cynomolgus monkeys after injection with anti-CD8α antibody. 11A represents the percentage of CD8+ cells within CD45+ cells in Cynomolgus monkeys which received 20 mg/kg bodyweight of anti-CD8α antibody clone MP08-R3-F08, MP08-R3-C11 or MP09-R3-D03 as indicated. 11B represents the percentage of CD8+ cells within CD45+ cells in Cynomolgus monkeys which received 7.5 mg/kg or 20 mg/kg bodyweight of anti-CD8α antibody clone MP08-R3-F08, as indicated.

Figure 12A:
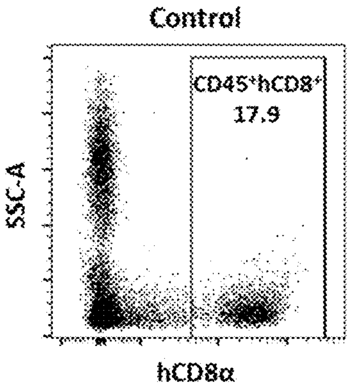
Figure 12B:
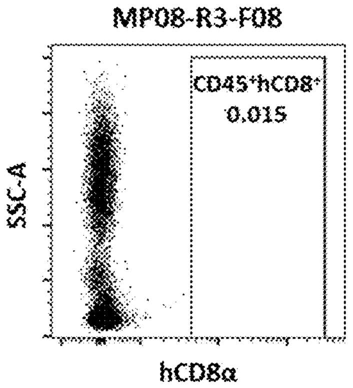
Figure 12C:
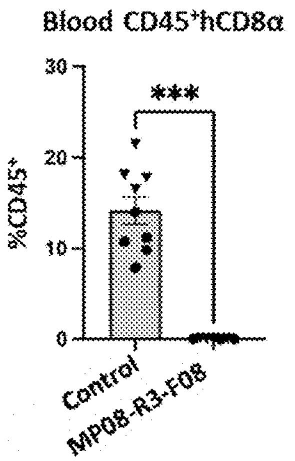

FIG. 12A-C is a combination of flow cytometry plots showing the percentage of $CD45^{+}hCD8\alpha^{+}$ cells in the blood of control transgenic mice expressing the human CD8α transgene which received saline solution (12A) and transgenic mice expressing the human CD8α transgene which received anti-CD8α antibody clone MP08-R3-F08 (12B), 3 days after injection, and of a histogram showing the quantification (12C). Males are represented by black circles and females by inverted black triangle. Control n=9 vs MP08-R3-F08 n=7. (***p<0.001).

Figure 13A:
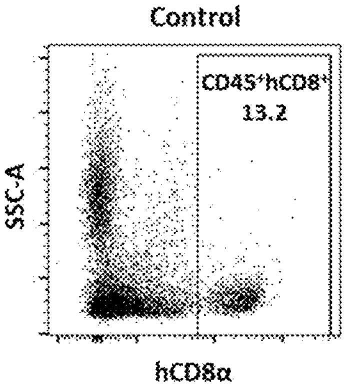
Figure 13B:
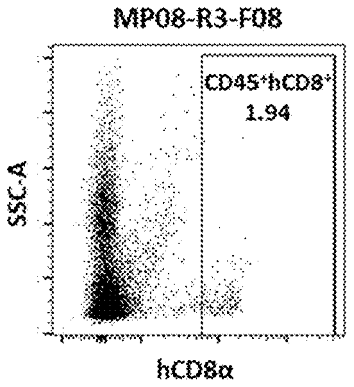
Figure 13C:
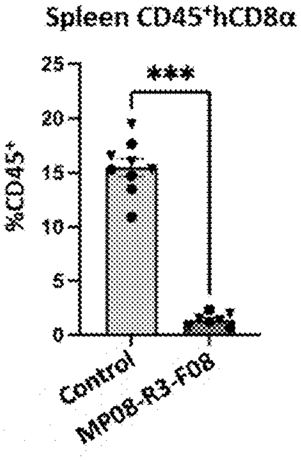

FIG. 13A-C is a combination of flow cytometry plots showing the percentage of $CD45^{+}hCD8\alpha^{+}$ cells in the spleen of control transgenic mice expressing the human CD8α transgene which received saline solution (13A) and transgenic mice expressing the human CD8α transgene which received anti-CD8α antibody clone MP08-R3-F08 (13B), 3 days after injection, and of a histogram showing the quantification (13C). Males are represented by black circles and females by inverted black triangle. Control n=9 vs MP08-R3-F08 n=7. (***p<0.001).

Figure 14:
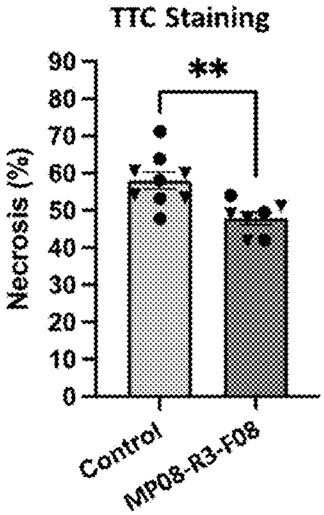

FIG. 14 is a histogram showing the percentage of necrosis measured by staining with 2,3,5-triphenyltetrazolium chloride (TTC) on heart sections from control transgenic mice expressing the human CD8α transgene which received saline solution or transgenic mice expressing the human CD8α transgene which received anti-CD8α antibody clone MP08-R3-F08, 3 days after induction of myocardial infarction. Males are represented by black circles and females by inverted black triangle. Control n=9 vs MP08-R3-F08 n=7. (**p<0.01).

DETAILED DESCRIPTION

In the present invention, the following terms have the following meanings:

"About" preceding a figure encompasses plus or minus 10%, or less, of the value of said figure. It is to be understood that the value to which the term "about" refers is itself also specifically, and preferably, disclosed.

"Affinity" is used to define the strength of an antibody-antigen complex. Affinity measures the strength of interaction between an antigen and an antibody, or an antigen-binding fragment thereof. It may be expressed by an affinity constant $K_A$ or by a dissociation constant $K_D$.

"Anti-CD8α" (also sometimes referred to as "anti-CD8α"), when qualifying an antibody, or an antigen-binding fragment thereof, means that said antibody, or antigen-binding fragment thereof, specifically binds to or specifically recognizes CD8α (cluster of differentiation 8 alpha).

"Antibody (Ab)" and "immunoglobulin (Ig)" may be used interchangeably and refer to a protein having a combination of two heavy chains (H chains) and two light chains (L chains). In particular, the term "antibodies" refers to such assemblies which have significant known specific immunoreactive activity to an antigen of interest (e.g., CD8α, in particular human CD8α). As explained elsewhere herein, "specificity" for human CD8α, does not exclude cross-reactivity with orthologs of human CD8α, such as, for example, with simian or murine CD8α. As mentioned above, antibodies and immunoglobulins comprise light and heavy chains, with or without an interchain covalent linkage between them. Basic immunoglobulin structures in vertebrate systems are relatively well-understood. The generic term "immunoglobulin" comprises five distinct classes of immunoglobulins that can be distinguished biochemically: IgG, IgM, IgA, IgD, and IgE. IgG immunoglobulins comprise two identical light chains with a molecular weight of about 23 kDa, and two identical heavy chains with a molecular weight of about 53-70 kDa. The four chains are joined by disulfide bonds in a "Y" configuration wherein the light chains bracket the heavy chains starting at the mouth of the "Y" and continuing through the variable region. The light chains of an immunoglobulin are classified as either kappa (κ) or lambda (λ). Each heavy chain class may be bonded with either a κ or λ light chain. In general, the light and heavy chains are covalently bonded to each other, and the "tail" regions of the two heavy chains are bonded to each other by covalent disulfide linkages or non-covalent linkages when the immunoglobulins are generated either by hybridomas, B cells or genetically engineered host cells. In the heavy chains, the amino acid sequence runs from the N-terminus at the forked ends of the Y configuration to the C-terminus at the bottom of each chain. Those skilled in the art will appreciate that heavy chains are classified as gamma (γ), mu (μ), alpha (α), delta (δ), or epsilon (ε) with some subclasses among them (e.g., γ1-γ4). It is the nature of the heavy chain that determines the "class" of the antibody as IgG, IgM, IgA, IgD, or IgE, respectively. The immunoglobulin subclasses or "isotypes" (e.g., IgG1, IgG2, IgG3, IgG4, IgA1, etc.) are well-characterized and are known to confer functional specialization. The variable region of an antibody allows the antibody to selectively recognize and specifically bind to an epitope on an antigen. That is, the light chain variable region (VL) and heavy chain variable region (VH) of an antibody combine to form the variable region that defines a three-dimensional antigen-binding site. This quaternary antibody structure thus forms the antigen-binding site present at the end of each arm of the "Y". More specifically, the antigen-binding site is defined by three complementarity determining regions (CDRs) on each of the VH and VL.

"Antigen-binding fragment" of an antibody, which is interchangeable with the term "antigen-binding domain" of an antibody, refers to a part or region of an antibody, or immunoglobulin, which comprises fewer amino acid residues than a whole antibody, or immunoglobulin, and which is capable of binding to an antigen and/or of competing with a whole antibody for antigen binding (e.g., for specific binding to CD8α). Examples of antigen-binding antibody fragments include, but are not limited to, Fab, Fab', $F(ab')_2$, Fv fragments, scFv fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR of an antibody.

Papain digestion of antibodies produces two identical antigen-binding fragments, called “Fab” fragments, and a residual “Fc” fragment, a designation reflecting the ability to crystallize readily. A Fab fragment consists of one entire L chain (variable region of the L chain (VL) and constant domain of the L chain (CL)), along with part of one H chain consisting of the variable region of the H chain (VH) and the first constant domain of the heavy chain (CH1). Each Fab fragment is monovalent with respect to antigen binding, i.e., it has a single antigen-binding site.

Pepsin treatment of an antibody yields a single large $F(ab')_2$ fragment that roughly corresponds to two disulfide-linked Fab fragments having divalent antigen-binding activity and is still capable of crosslinking antigen.

Fab' fragments differ from Fab fragments by having additional few amino acid residues at the carboxy terminus of the CH1 domain including one or more cysteines from the antibody hinge region.

Fab'-SH is the designation for Fab' in which the cysteine residue(s) of the constant domains bear(s) a free thiol group.

$F(ab')_2$ antibody fragments originally were produced as pairs of Fab' fragments that have hinge cysteines between them. Other chemical couplings of antibody fragments are also known.

“Antigen” or “Ag” as used herein refers to a protein (e.g., CD8α), which is specifically recognized by an antibody or antibody-binding fragment thereof.

“CD8”, or “cluster of differentiation 8” refer to a transmembrane glycoprotein notably expressed on cytotoxic T lymphocytes. The CD8 molecule serves as co-receptor for the T-cell receptor (TCR) on T cells to recognize antigens displayed by antigen presenting cells in the context of class I MHC molecules. CD8 functions either as a homodimer composed of two CD8α chains, or as a heterodimer composed of one CD8α chain and one CD8β chain. Both CD8α and CD8β are members of the immunoglobulin superfamily. Both CD8α and CD8β chains comprise one unique immunoglobulin-like domain constituting the extracellular part of the protein, which is anchored to the cell membrane through a long glycosylated peptide chain. The two chains constituting the CD8 dimer (i.e., heterodimer CD8α/CD8P or homodimer CD8α/CD8α) are associated through a disulfide bond.

In the NCBI databases (https://www.ncbi.nlm.nih.gov), the reference human CD8α gene sequence corresponds to NCBI Gene ID: 925, as updated on Aug. 5, 2022. The human CD8α (hCD8α) gene consists of 10 exons on chromosome 2p11.2, and encodes a 235 amino acid protein for isoform 1 and a 198 amino acid protein for isoform 2. Human CD8α isoform 1 refers to the protein referenced as NP_001139345.1, NP_001759.3 or NP_001369627.1 in the NCBI databases, while isoform 2 refers to the protein referenced as NP_741969.1. Alternative names for CD8α include “T-cell surface glycoprotein CD8 alpha chain”, “CD8 antigen”, “alpha polypeptide”, “Leu2 T-lymphocyte antigen”, “OKT8 T-cell antigen”, “T cell co-receptor”, “T-cell antigen Leu2”, “T-lymphocyte differentiation antigen T8”, “T8 T-cell antigen”, “p32”, “Leu-2” and “Leu2” as non-limiting examples. Herein, the expressions “CD8α” and “CD8” are used indifferently.

In the NCBI databases, the reference human CD8β gene sequence corresponds to NCBI Gene ID: 926, as updated on Aug. 5, 2022. The human CD8β gene consists of 8 exons on chromosome 2p11.2, and encodes 6 isoforms by alternative splicing: a 246 amino acid protein for isoform 1, a 243 amino acid protein for isoform 2, a 221 amino acid protein for isoform 3, a 213 amino acid protein for isoform 4, a 210 amino acid protein for isoform 5 and a 198 amino acid protein for isoform 6. Human CD8β isoform 1 refers to the protein referenced as XP_011531466.1 in the NCBI databases, isoform 2 refers to the protein referenced as NP_757362.1, isoform 3 refers to the protein referenced as NP_742099.1, isoform 4 refers to the protein referenced as NP_742100.1, isoform 5 refers to the protein referenced as NP_004922.1, and isoform 6 refers to the protein referenced as NP_001171571.1. Alternatives names for CD8β include “LY3”, “P37”, “LEU2”, “LYT3”, “CD8B1”, “T-cell surface glycoprotein CD8 beta chain”, “CD8 antigen”, “beta polypeptide 1”, “T lymphocyte surface glycoprotein beta chain” as non-limiting examples.

“CDR” or “complementarity determining region” means the non-contiguous antigen combining sites found within the variable region of both the heavy chain and the light chain. The precise amino acid sequence boundaries of a given CDR can be determined using any of a number of well-known schemes, including those described by Kabat et al. (1991), “Sequences of Proteins of Immunological Interest” 5th Ed. Public Health Service, National Institutes of Health, Bethesda, MD (“Kabat” numbering scheme); Al-Lazikani et al., (1997) JMB 273,927-948 (“Chothia” numbering scheme); or a combination thereof such as the AbM definition which is a compromise between the two used by Oxford Molecular's AbM antibody modelling software. More recently, a universal numbering system has been developed and widely adopted, ImMunoGeneTics (IMGT) Information System® (Lefranc et al., Nucleic Acids Res. 27: 209-212 1999). IMGT® is an integrated information system specializing in immunoglobulins (Ig), T cell receptors (TCR) and major histocompatibility complex (MHC) of human and other vertebrates. Herein, the CDRs are referred to in terms of both the amino acid sequence and the location within the light or heavy chain (e.g., $_{VH}$-CDR1, $_{VH}$-CDR2, $_{VH}$-CDR3, $_{VL}$-CDR1, $_{VL}$-CDR2, $_{VL}$-CDR3). As the “location” of the CDRs within the structure of the immunoglobulin variable region is conserved between species and present in structures called loops, by using numbering systems that align variable region sequences according to structural features, CDR and framework amino acid residues may be readily identified. This information can be used in grafting and replacement of CDRs from immunoglobulins of one species into an acceptor framework from, typically, a human antibody. Correspondence between the Kabat numbering and the IMGT® unique numbering system is also well-known to one skilled in the art (e.g., Lefranc et al., supra).

“Epitope” refers to a specific arrangement of amino acids located on a protein or proteins to which an antibody, or an antigen-binding fragment thereof, specifically binds. Epitopes often consist of a chemically active surface grouping of molecules such as amino acids or sugar side chains, and have specific three-dimensional structural characteristics as well as specific charge characteristics. Epitopes can be linear (or sequential) or conformational, i.e., involving two or more sequences of amino acids in various regions of the antigen that may not necessarily be contiguous.

“Fc domain,” “Fe portion,” and “Fe region” may be used interchangeably and refer to a C-terminal fragment of an antibody heavy chain, e.g., from about amino acid (aa) 230 to about aa 450 of human gamma heavy chain or its counterpart sequence in other types of antibody heavy chains (e.g., α, δ, ε and for human antibodies), or a naturally occurring allotype thereof.

"Framework region" or "FR region" or "non-CDR region" includes the amino acid residues that are part of the variable region, but are not part of the CDRs (e.g., using the Kabat definition of CDRs, the Chothia definition of CDRs, or the IMGT® numbering definition of CDRs). Therefore, a variable region framework ranges from about 100 to 120 amino acids in length but includes only those amino acids outside of the CDRs.

For the specific example of a heavy chain variable region (VH) and for the CDRs as defined by Kabat or Chothia:

FR1 may correspond to the domain of the variable region encompassing amino acids 1-25 according to Chothia/AbM's definition, or 5 amino acid residues later according to Kabat's definition;

FR2 may correspond to the domain of the variable region encompassing amino acids 36-49;

FR3 may correspond to the domain of the variable region encompassing amino acids 67-98; and FR4 may correspond to the domain of the variable region from amino acid 104-110 to the end of the variable region.

The framework regions for the light chain are similarly separated by each of the CDRs of the light chain variable region (VL).

In naturally occurring antibodies, the six CDRs present on each monomeric antibody are short, non-contiguous sequences of amino acids that are specifically positioned to form the antigen-binding site as the antibody assumes its three-dimensional configuration in an aqueous environment. As indicated above, the remainders of the heavy and light variable regions show less inter-molecular variability in amino acid sequence and correspond to the framework regions. The framework regions largely adopt a β-sheet conformation and the CDRs form loops which connect, and in some cases form part of, the β-sheet structure. Thus, these framework regions act to form a scaffold for positioning the six CDRs in correct orientation by inter-chain, non-covalent interactions. The antigen-binding site formed by the positioned CDRs defines a surface complementary to the epitope on the immunoreactive antigen. This complementary surface promotes the non-covalent binding of the antibody to the immunoreactive antigen epitope.

"Heavy chain region" includes amino acid sequences derived from the constant domains of an immunoglobulin heavy chain. A protein comprising a heavy chain region comprises at least one of a CH1 domain, a hinge region (e.g., upper, middle, and/or lower hinge domain), a CH2 domain, a CH3 domain, or a variant or fragment thereof. In some embodiments, the antibody, or the antigen-binding fragment thereof, as described herein may comprise the Fc region of an immunoglobulin heavy chain (e.g., a hinge portion, a CH2 domain, and a CH3 domain). In some embodiments, the antibody, or the antigen-binding fragment thereof, as described herein lacks at least a region of a constant domain (e.g., all or part of a CH2 domain). In some embodiments, at least one, and preferably all, of the constant domains are derived from a human immunoglobulin heavy chain. For example, in some embodiments, the heavy chain region comprises a fully human hinge domain. In some embodiments, the heavy chain region comprises a fully human Fc region (e.g., hinge, CH2 and CH3 domain from a human immunoglobulin). In some embodiments, the constituent constant domains of the heavy chain region are from different immunoglobulin molecules. For example, a heavy chain region of a protein may comprise a CH2 domain derived from an IgG1 molecule and a hinge region derived from an IgG3 or IgG4 molecule. In some embodiments, the constant domains are chimeric domains comprising regions of different immunoglobulin molecules. For example, a hinge may comprise a first region from an IgG1 molecule and a second region from an IgG3 or IgG4 molecule. In some embodiments, the constant domains of the heavy chain region may be modified such that they vary in amino acid sequence from the naturally occurring (wild-type) immunoglobulin molecule. That is, the antibody, or the antigen-binding fragment thereof, as described herein may comprise alterations or modifications to one or more of the heavy chain constant domains (CH1, hinge, CH2 or CH3) and/or to the light chain constant domain (CL). Exemplary modifications include additions, deletions or substitutions of one or more amino acids in one or more domains.

"Hinge region" includes the region of a heavy chain molecule that joins the CH1 domain to the CH2 domain. This hinge region comprises approximately 25 amino acid residues and is flexible, thus allowing the two N-terminal antigen-binding regions to move independently. Hinge regions can be subdivided into three distinct domains: upper, middle, and lower hinge domains.

"Identity" or "identical", when used in the present invention in a relationship between the sequences of two or more polypeptides or of two or more nucleic acids, refers to the degree of sequence relatedness between polypeptides or nucleic acids (respectively), as determined by the number of matches between strings of two or more amino acid residues or of two or more nucleotides, respectively. "Identity" measures the percent of identical matches between the smaller of two or more sequences with gap alignments (if any) addressed by a particular mathematical model or computer program (i.e., "algorithms"). Identity of related polypeptides or nucleic acid sequences can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucleic Acids Res. 1984 Jan. 11; 12(1 Pt 1):387-95; Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., J. Mol. Biol. 215, 403-410 (1990)). The well-known Smith Waterman algorithm may also be used to determine identity.

"Isolated" or "non-naturally occurring" with reference to a biological component (such as an antibody or a nucleic acid) refers to a biological component altered or removed from the natural state. For example, an antibody or a nucleic acid naturally present in a living animal is not “isolated” but the same antibody or nucleic acid partially or completely separated from the coexisting materials of its natural state is “isolated”. An isolated antibody or nucleic acid can exist in substantially purified form, or can exist in a non-native environment such as, for example, a host cell. Typically, a preparation of isolated antibody or nucleic acid contains the antibody or nucleic acid at least about 80% pure, at least about 85% pure, at least about 90% pure, at least about 95% pure, greater than 95% pure, greater than about 96% pure, greater than about 97% pure, greater than about 98% pure, or greater than about 99% pure. Nucleic acids and proteins, such an antibodies, that are “non-naturally occurring” or have been “isolated” include nucleic acids and proteins purified by standard purification methods. The term also embraces nucleic acids and proteins prepared by recombinant expression in a host cell as well as chemically synthesized nucleic acids.

“Monoclonal antibody (mAb)” refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant (epitope) on the antigen. In addition to their specificity, the monoclonal antibodies are advantageous in that they may be synthesized uncontaminated by other antibodies. The modifier “monoclonal” is not to be construed as requiring production of the antibody by any particular method. For example, a monoclonal antibody, or an antigen-binding fragment thereof, as described herein may be prepared by the well-known hybridoma methodology, or may be made using recombinant DNA methods in bacterial, eukaryotic, animal, or plant cells. The “monoclonal antibodies” may also be isolated from phage antibody libraries using techniques commonly known in the field.

As used herein, the term “nucleic acid” or “polynucleotide” refers to a polymer of nucleotides covalently linked by phosphodiester bonds, such as deoxyribonucleic acids (DNA) or ribonucleic acids (RNA), in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues.

“Pharmaceutically acceptable excipient” or “pharmaceutically acceptable carrier” refers to an excipient or carrier that does not produce an adverse, allergic or other untoward reaction when administered to a mammal, preferably a human. It includes any and all solvents, such as, for example, dispersion media, coatings, antibacterial and antifungal agents, isotonic and absorption delaying agents. A pharmaceutically acceptable excipient or carrier refers to a non-toxic solid, semi-solid or liquid filler, diluent, encapsulating material or formulation auxiliary of any type. For human administration, preparations should meet sterility, pyrogenicity, general safety and purity standards as required by the regulatory offices such as the FDA (US Food and Drug Administration) or EMA (European Medicines Agency).

“Single-chain Fv”, also abbreviated as “sFv” or “scFv”, refers to a fusion protein comprising at least one antibody fragment comprising a variable region of a light chain (VL) and at least one antibody fragment comprising a variable region of a heavy chain (VH), wherein the light and heavy chain variable regions are contiguously linked, e.g., via a synthetic linker, such as a short flexible polypeptide linker, and capable of being expressed as a single chain polypeptide, and wherein the scFv retains the specificity of the intact antibody from which it is derived.

“Subject” refers to a warm-blooded animal, more preferably a mammal. The term “mammal” refers here to any mammal, including humans. Preferably, the mammal is a primate, more preferably a human. In some embodiments, a subject may be a “patient”, who/which is awaiting the receipt of, or is receiving medical care or was/is/will be the object of a medical procedure, or is monitored for the development of the targeted disease or condition. In some embodiments, the subject is an adult (for example a subject above the age of 18). In some embodiments, the subject is a child (for example a subject below the age of 18). In some embodiments, the subject is a male. In some embodiments, the subject is a female.

“Variable”, “variable region” or “variable domain” refer to the fact that certain regions of the variable domains $V_H$ and $V_L$ differ extensively in sequence among antibodies and are used in the binding and specificity of each particular antibody for its target antigen. However, the variability is not evenly distributed throughout the variable domains of antibodies. It is concentrated in three segments called “hypervariable loops” in each of the VL domain and the VH domain which form part of the antigen-binding site. The 6 hypervariable loops may each comprise part of a CDR, as defined hereinabove.

A first object of the present invention relates to an isolated antibody, or to an antigen-binding fragment thereof, which specifically binds to cluster of differentiation 8 alpha (CD8α). A first object of the present invention thus relates to an isolated anti-CD8α antibody, or to an antigen-binding fragment thereof.

As used herein, an antibody or antigen-binding fragment thereof is said to be “specific for”, “immunospecific” or to “specifically bind” its cognate antigen (e.g., CD8α) if it reacts at a detectable level with said antigen. The binding properties of an antibody, or an antigen-binding fragment thereof, to its cognate antigen (or cells or tissues expressing said antigen) may generally be determined and assessed using immunodetection methods well-known in the art including, for example, enzyme-linked immunosorbent assay (ELISA), immunofluorescence-based assays, such as immunohistochemistry (IHC) and/or fluorescence-activated cell sorting (FACS); or by surface plasmon resonance (SPR).

The affinity of an antibody, or an antigen-binding fragment thereof, for its cognate antigen (e.g., CD8α) can be readily determined using conventional techniques, for example, those described by Scatchard, 1949. *Ann NY Acad Sci.* 51:660-672. Affinity of an antibody, or an antigen-binding fragment thereof, for its cognate antigen is commonly expressed as an equilibrium dissociation constant ($K_D$). Thus, in some embodiments, the isolated anti-CD8α antibody, or an antigen-binding fragment thereof, is said to be “immunospecific”, “specific for” or to “specifically bind”

to its cognate antigen CD8α if it reacts at a detectable level with said antigen with a $K_D$ of less than or equal to $10^{-6}$ M.

In some embodiments, the isolated anti-CD8α antibody, or the antigen-binding fragment thereof, as described herein specifically binds to human CD8α (hCD8α or huCD8α). In other words, in some embodiments, the isolated antibody, or the antigen-binding fragment thereof, is an anti-hCD8α antibody, or anti-hCD8α antigen-binding fragment thereof.

The binding of an antibody, or an antigen-binding fragment thereof, for its cognate antigen may also be assessed through the determination of the concentration of antibody, or antigen-binding fragment thereof, that gives half-maximal binding (i.e., EC50). For example, the EC50 of an antibody, or an antigen-binding fragment thereof, may be determined with an enzyme-linked immunosorbent assay (ELISA), in particular with a dose-response ELISA. In some embodiments, the isolated anti-CD8α antibody, or an antigen-binding fragment thereof, binds CD8α, preferably hCD8α, with an EC50 of less than 10 nM, preferably less than 5 nM, more preferable less than 2.5 nM, in particular as determined with dose-response ELISA.

In some embodiments, the isolated anti-CD8α antibody, or antigen-binding fragment thereof, as described herein specifically binds human CD8α having an amino acid sequence as set forth in SEQ ID NO: 30, corresponding to NCBI accession number NP_001759.3, last modified on Jun. 12, 2022.

In some embodiments, the isolated anti-CD8α antibody, or antigen-binding fragment thereof, specifically binds to the extracellular domain of CD8α.

In some embodiments, the isolated anti-CD8α antibody, or antigen-binding fragment thereof, as described herein specifically binds to human CD8α isoform 1 and isoform 2. In some embodiments, the isolated anti-CD8α antibody, or antigen-binding fragment thereof, as described herein specifically binds to human CD8α isoform 1 and isoform 2 both secreted form and tethered secreted form.

In some embodiments, the isolated anti-CD8α antibody, or antigen-binding fragment thereof, as described herein specifically binds to CD8α, in particular to human CD8α, present at the surface of leukocytes. In some embodiments, leukocytes encompass CD8+T lymphocytes (also known as CD8+ T cells), CD8α-expressing dendritic cells (also referred to as CD8+ dendritic cells) and CD8α-expressing Natural Killer (NK) cells (also referred to as CD8+NK cells).

In some embodiments, the isolated anti-CD8α antibody, or antigen-binding fragment thereof, as described herein is able to deplete CD8α-expressing cells (which may also be referred to as CD8+ cells). Thus, in some embodiments, the isolated anti-CD8α antibody, or antigen-binding fragment thereof, is a depleting antibody, that is to say a CD8α-expressing cell depleting antibody (which may also be referred to as a CD8+ cell depleting antibody). The CD8α-expressing cells may be CD8α-expressing leucocytes, in particular CD8α-expressing T cells (also referred to as CD8+ T cells), CD8α-expressing NK cells (also referred to as CD8+NK cells) and/or CD8α-expressing dendritic cells (also referred to as CD8+ dendritic cells). The isolated anti-CD8α antibody, or antigen-binding fragment thereof, as described herein may thus be able to deplete CD8+ T cells and/or CD8+NK cells. Accordingly, in some embodiments, the isolated anti-CD8α antibody, or antigen-binding fragment thereof, is a CD8α-expressing T cell depleting antibody, also referred to as a CD8+ T cell depleting antibody.

The isolated anti-CD8α antibody, or antigen-binding fragment thereof, as described herein may be able to induce the in vitro depletion of CD8α-expressing cells in a sample upon contact with said sample. The isolated anti-CD8α antibody, or antigen-binding fragment thereof, as described herein may be able to induce the in vivo depletion of CD8α-expressing cells in an organism or subject upon administration to said organism or subject.

As used herein, the terms "a CD8α-expressing cell depleting antibody" or "a CD8+ cell depleting antibody" refer to an antibody which binds to CD8α (i.e., CD8) expressed at the surface of CD8α-expressing cells (i.e., CD8+ cells) and which mediate the destruction or depletion of said cells upon binding to CD8α (i.e., CD8).

As used herein "deplete", "depleting", "depletion" with respect to cells expressing CD8α as described herein refer to a measurable decrease or reduction in the number of CD8α-expressing cells in a sample, in an organism or in a subject. For example, depletion with respect to cells expressing CD8α as described herein may refer to a measurable decrease or reduction in the number of circulating CD8α-expressing cells, and/or tissue-infiltrating CD8α-expressing cells, and/or CD8α-expressing cells present in the lymph nodes and/or in the spleen in an organism or in a subject.

The decrease or reduction may be at least about 10%, e.g., at least about 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, or more, in particular with reference to the initial number of CD8α-expressing cells in the sample, organism or subject. As used herein, "initial number of CD8α-expressing cells" (or "number of CD8α-expressing cells at baseline") refers to the number of CD8α-expressing cells in a sample, organism or subject before depletion induced by the isolated anti-CD8α antibody, or antigen-binding fragment thereof, as described herein (i.e., before administration of the isolated anti-CD8α antibody, or antigen-binding fragment thereof, as described herein). In some embodiments, the initial number of CD8α-expressing cells in an organism or subject is a normal number of CD8α-expressing cells, that is to say a number of CD8α-expressing cells within the range considered normal or standard (i.e., normal range) for the organism or subject. For example, a normal number of CD8+ T cells (in particular circulating CD8+ T cells) in healthy human adults ranges from 150 to 1000 cells/$mm^3$. A normal mean number of CD8+ T cells (in particular circulating CD8+ T cells) in healthy human adults may thus be about 550 cells/μL. In some embodiments, the decrease or reduction may be at least about 10%, e.g., at least about 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%, or more, with reference to a number of CD8α-expressing cells in the organism or subject within the normal range for said organism or subject.

In some embodiments, the terms "deplete", "depleting", "depletion" with respect to cells expressing CD8α as described herein refer to a decrease or reduction in the number of CD8α-expressing cells in a sample, organism or subject to an amount below detectable limits.

As indicated above, the depletion of CD8α-expressing cells induced by the isolated anti-CD8α antibody, or antigen-binding fragment thereof, as described herein may be a complete depletion. By "complete depletion" it is meant that, after depletion induced by the isolated anti-CD8α antibody, or antigen-binding fragment thereof, CD8α-expressing cells are decreased by at least about 90%, preferably at least about 95%, 96%, 97%, 98%, or 99%, in particular with reference to the initial number of CD8α-expressing cells in the sample, organism or subject, preferably for at least about 1, 2, 3, 4, 5, 6, or 7 day(s).

The depletion of CD8α-expressing cells induced by the isolated anti-CD8α antibody, or antigen-binding fragment thereof, as described herein may be a transient depletion. By "transient depletion" it is meant that, depletion of the CD8α-expressing cells induced by the isolated anti-CD8α antibody, or antigen-binding fragment thereof, is followed by a repopulation of CD8α-expressing cells, preferably starting about 2, 3, 4, 5, 6, 7 or 8 week(s) after the initial depletion.

As used herein, "repopulation" means that after CD8α-expressing cell depletion, the number of CD8α-expressing cells in a sample, in an organism or in a subject increases. The increase may be sufficient to reach at least about 10%, e.g., at least about 15%, 20%, 25%, 30%, 35%, 40%, 45%, or 50%, preferably at least about 55%, 60%, 65%, 70%, or 75%, more preferably at least about 80%, 85%, 90%, or 95%, or more, in particular with reference to the initial number of CD8α-expressing cells in the sample, organism or subject. In some embodiments, the increase may be sufficient to reach at least about 10%, e.g., at least about 15%, 20%, 25%, 30%, 35%, 40%, 45%, or 50%, preferably at least about 55%, 60%, 65%, 70%, or 75%, more preferably at least about 80%, 85%, 90%, or 95%, or more, with reference to a number of CD8α-expressing cells in the organism or subject within the normal range for said organism or subject.

The isolated anti-CD8α antibody, or antigen-binding fragment thereof, may deplete CD8α-expressing cells as described herein by binding to CD8α and by activating antibody-dependent cell mediated cytotoxicity (ADCC), complement dependent cytotoxicity (CDC) and/or antibody dependent cellular phagocytosis (ADCP); and/or by inhibiting proliferation of CD8α-expressing cells; and/or by inducting CD8α-expressing cells cell death (for example via apoptosis).

The isolated anti-CD8α antibody, or antigen-binding fragment thereof, may be able to deplete CD8α-expressing cells as described herein through antibody-dependent cell mediated cytotoxicity.

As used herein the term "antibody-dependent cell mediated cytotoxicity" or "ADCC" refers to a form of cytotoxicity in which antibodies bound onto Fc receptors (FcRs) present on certain cytotoxic cells (e.g., NK cells, neutrophils, monocytes and macrophages) enable these cytotoxic effector cells to bind specifically to an antigen-bearing target cell (e.g., a CD8-expressing cell as described herein) and subsequently to kill the target cell. To assess the ADCC activity of a molecule of interest, an in vitro ADCC assay, such as that described in U.S. Pat. No. 5,500,362 or U.S. Pat. No. 5,821,337, may be performed.

The isolated anti-CD8α antibody, or antigen-binding fragment thereof, may be able to deplete CD8α-expressing cells as described herein through complement dependent cytotoxicity.

As used herein, the term "complement dependent cytotoxicity" or "CDC" refers to the lysis of a target cell in the presence of complement. Activation of the classical complement pathway is initiated by the binding of the first component of the complement system to antibodies which are bound to their cognate antigen (e.g., CD8α). To assess complement activation, a CDC assay such as that described in Gazzano-Santoro et al., 1997. J Immunol Methods. 202 (2):163-71, may be performed.

The isolated anti-CD8α antibody, or antigen-binding fragment thereof, may be able to deplete CD8α-expressing cells as described herein through antibody dependent phagocytosis.

As used herein the term "antibody dependent cellular phagocytosis" or "ADCP" refers to a form of phagocytosis in which antibodies bound onto Fc receptors (FcRs) present on certain phagocytic cells (e.g., monocytes, macrophages, neutrophils, dendritic cells, and mast cells) enable these phagocytic cells to bind specifically to an antigen-bearing target cell (e.g., a CD8-expressing cell as described herein) and subsequently to phagocyte the target cell.

Methods for assessing whether a compound, such as an antibody or antigen-binding fragment thereof, is able to deplete CD8α-expressing cells are well-known in the art and comprise, for example, the assays described hereinafter in the example section.

Assays for evaluating whether an anti-CD8α antibody, or antigen-binding fragment thereof, is depleting CD8α-expressing cells include the detection and quantification by flow cytometry of hCD8α-expressing cells in transgenic mice expressing the hCD8α transgene after injection of the anti-CD8α antibody, or antigen-binding fragment thereof. In some embodiments, an anti-CD8α antibody, or antigen-binding fragment thereof, able to decrease the number of hCD8α-expressing cells, in particular as compared to the baseline number of hCD8α-expressing cells (i.e., the number of hCD8α-expressing cells before injection of the anti-CD8α antibody, or antigen-binding fragment thereof), is a CD8α-expressing cell depleting antibody, or antigen-binding fragment thereof. In some embodiments, the decrease in the number of hCD8α-expressing cells is assessed 1, 2, 3, 4, or 5 hour(s) after injection of the anti-CD8α antibody, or antigen-binding fragment thereof. In some embodiments, the decrease in the number of hCD8α-expressing cells is assessed 1, 2, 3, 4, 5, 6 or 7 day(s) after injection of the anti-CD8α antibody, or antigen-binding fragment thereof. In some embodiments, the decrease in the number of hCD8α-expressing cells is assessed 1, 2, or 3 week(s) after injection of the anti-CD8α antibody, or antigen-binding fragment thereof.

Assays for evaluating whether an anti-CD8α antibody, or antigen-binding fragment thereof, is depleting CD8α-expressing cells also include the detection and quantification by flow cytometry of CD8α-expressing cells in non-human primates, for example in cynomolgus monkeys (*Macaca fascicularis*) after injection of the anti-CD8α antibody, or antigen-binding fragment thereof. In some embodiments, an anti-CD8α antibody, or antigen-binding fragment thereof, able to decrease the number of CD8α-expressing cells as compared to the baseline number of hCD8α-expressing cells (i.e., the number of hCD8α-expressing cells before injection of the anti-CD8α antibody, or antigen-binding fragment thereof), is a CD8α-expressing cell depleting antibody, or antigen-binding fragment thereof. In some embodiments, the decrease in the number of hCD8α-expressing cells is assessed 1, 2, 3, 4, 5, 6, 7, 8, 9, or 10 hour(s) after injection of the anti-CD8α antibody, or antigen-binding fragment thereof. In some embodiments, the decrease in the number of hCD8α-expressing cells is assessed 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 day(s) after injection of the anti-CD8α antibody, or antigen-binding fragment thereof. In some embodiments, the decrease in the number of hCD8α-expressing cells is assessed 1, 2, 3, 4, 5, 6, 7, 8, 9, or 10 week(s) after injection of the anti-CD8α antibody, or antigen-binding fragment thereof.

In some embodiments, the isolated anti-CD8α antibody, or antigen-binding fragment thereof, as described herein is able to limit necrosis after myocardial infarction. In some embodiments, the isolated anti-CD8α antibody, or antigen-binding fragment thereof, as described herein is able to reduce the infarct size after myocardial infarction. In some embodiments, the isolated anti-CD8α antibody, or antigen-binding fragment thereof, as described herein is able to improve cardiac function after myocardial infarction. In some embodiments, the isolated anti-CD8α antibody, or antigen-binding fragment thereof, as described herein is able to improve the left ventricular ejection fraction after myocardial infarction.

Methods for assessing whether a compound, such as an antibody or antigen-binding fragment thereof, is able to limit necrosis, reduce the infarct size, improve cardiac function, and/or improve the left ventricular ejection fraction after myocardial infarction are well-known in the art and comprise, for example, the assays described hereinafter in the example section.

Assays for evaluating whether an anti-CD8α antibody, or antigen-binding fragment thereof, is able to limit necrosis after myocardial infarction include measuring the percentage of necrosis on heart tissue slices from transgenic mice expressing the hCD8α transgene after injection of the anti-CD8α antibody, or antigen-binding fragment thereof. In some embodiments, the percentage of necrosis is assessed 3 days after myocardial infarction. In some embodiments, heart tissue slices are stained with 2,3,5-triphenyltetrazolium chloride (TTC).

Assays for evaluating whether an anti-CD8α antibody, or antigen-binding fragment thereof, is able to reduce the infarct size after myocardial infarction include calculating the infarct size by measuring the total tissue area and the infarcted tissue area on heart tissue slices from transgenic mice expressing the hCD8α transgene after injection of the anti-CD8α antibody, or antigen-binding fragment thereof. In some embodiments, the infarct size is assessed 3 days after myocardial infarction. In some embodiments, heart tissue slices are stained with 2,3,5-triphenyltetrazolium chloride (TTC).

Assays for evaluating whether an anti-CD8α antibody, or antigen-binding fragment thereof, is able to improve cardiac function and/or improve the left ventricular ejection fraction after myocardial infarction include calculating left ventricular end-diastolic volume (EDV) and end-systolic volume (ESV) in transgenic mice expressing the hCD8α transgene after injection of the anti-CD8α antibody, or antigen-binding fragment thereof. In some embodiments, cardiac function is assessed 21 days after myocardial infarction. In some embodiments, left ventricular end-diastolic volume (EDV) and end-systolic volume (ESV) are calculated 21 days after myocardial infarction. In some embodiments, cardiac function is recorded using an imaging system adapted for mouse cardiovascular imaging.

In some embodiments, "isolated", as in "isolated antibody or isolated antigen-binding fragment thereof", refers to an antibody, or antigen-binding fragment thereof, that is substantially free of other proteins or antibodies having different antigenic specificities. Thus, the isolated anti-CD8α antibody, or antigen-binding fragment thereof, as described herein is substantially free of proteins or antibodies, or antigen-binding fragments thereof, that specifically bind antigens other than CD8α. The isolated antibody, or the antigen-binding fragment thereof, that specifically binds CD8α as described herein may, however, have cross-reactivity to other related antigens, such as CD8α from other genera or species.

Moreover, the isolated anti-CD8α antibody, or antigen-binding fragment thereof, as described herein may be substantially free of other cellular material and/or chemicals, in particular those that would interfere with any uses (such as any therapeutic uses) of the antibody, or antigen-binding fragment thereof, including without limitation, enzymes, hormones, and other proteinaceous or non-proteinaceous components.

In some embodiments, the isolated anti-CD8α antibody, or antigen-binding fragment thereof, as described herein is purified.

In some embodiments, the isolated anti-CD8α antibody, or antigen-binding fragment thereof, is purified to obtain a purity greater than about 80%, 85%, 90%, 91%, 92%, 93%, 94%, 95%, 96%, 98%, or 99% by weight of antibody or antigen-binding fragment, preferably greater than about 95%, 96%, 97%, 98%, or 99% by weight of antibody or antigen-binding fragment. In some embodiments, the purity is determined by analytical size exclusion chromatography (SEC), such as size exclusion high-performance liquid chromatography (SE HPLC).

In some embodiments, the isolated anti-CD8α antibody, or antigen-binding fragment thereof, specifically binds to human CD8α and to at least one ortholog of human CD8α. Thus, in some embodiments, the isolated anti-CD8α antibody, or antigen-binding fragment thereof, binds to human CD8α and to at least one CD8α from another genus or species. In other words, in some embodiments, the isolated anti-CD8α antibody, or antigen-binding fragment thereof, displays cross-reactivity (cross-reacts). In some embodiments, the isolated anti-CD8α antibody, or antigen-binding fragment thereof, binds to human CD8α and to cynomolgus monkey CD8α (in particular to CD8α of *Macaca fascicularis*).

In some embodiments, the isolated anti-CD8α antibody, or antigen-binding fragment thereof, does not bind to mouse CD8α (in particular to CD8α of *Mus musculus*).

In some embodiments, the isolated anti-CD8α antibody, or antigen-binding fragment thereof, does not exhibit any off-target binding.

In some embodiments, the antigen-binding fragment of the anti-CD8α antibody is a molecule selected from the group comprising or consisting of a single-chain antibody or scFv, a dimeric single-chain antibody or di-scFv, a Fv, a Fab, a Fab', a Fab'-SH, and a $F(ab')_2$.

Antigen-binding fragments of antibodies can be obtained using standard methods. For instance, Fab or $F(ab')_2$ fragments may be produced by protease digestion of the isolated antibodies, according to conventional techniques. Alternatively, antigen-binding fragments of antibodies, such as Fab fragments, may be expressed as recombinant proteins.

In some embodiments, the isolated anti-CD8α antibody is a whole antibody. In some embodiments, the isolated anti-CD8α antibody, or the antigen-binding fragment thereof, is selected from the group comprising or consisting of a Fc silent antibody or antigen-binding fragment thereof (i.e., an antibody or antigen-binding fragment thereof comprising a Fc silent), an antibody or antigen-binding fragment thereof with an engineered Fc such as a defucosylated Fc (defucosylated antibody), and a bispecific antibody or antigen-binding fragment thereof. In some embodiments, the antigen-binding fragment of the anti-CD8α antibody is a diabody, a triabody, or a tetrabody.

In some embodiments, the anti-CD8α antibody, or the antigen-binding fragment thereof, is from the IgG class. The anti-CD8α antibody, or antigen-binding fragment thereof, may thus be from the IgG1, IgG2, IgG3, or IgG4 subclass.

In some embodiments, the anti-CD8α antibody, or the antigen-binding fragment thereof, is from the IgG1 subclass, preferably from the human IgG1 subclass. In some embodiments, the anti-CD8α antibody, or the antigen-binding fragment thereof, is thus an IgG1 antibody, preferably a human IgG1 antibody or a chimeric human IgG1 antibody.

In some embodiments, the anti-CD8α antibody, or the antigen-binding fragment thereof, is from the IgG2 subclass, preferably from the human IgG2 subclass. In some embodiments, the anti-CD8α antibody, or the antigen-binding fragment thereof, is thus an IgG2 antibody, preferably a human-IgG2 antibody or a chimeric human IgG2 antibody. In particular, the IgG2 antibody may be a IgG2b antibody.

As used herein, a "chimeric antibody" refers to an antibody or antigen-binding fragment thereof comprising a first amino acid sequence linked to a second amino acid sequence with which it is not naturally linked in nature. The amino acid sequences may normally exist in separate proteins that are brought together in the chimeric (or fusion) protein or may normally exist in the same protein but are placed in a new arrangement in the chimeric (or fusion) protein. A chimeric protein may be created, for example, by chemical synthesis, or by creating and translating a polynucleotide in which the peptide regions are encoded in the desired relationship. The term "chimeric antibody" comprises antibodies and antigen-binding fragment thereof in which:

(a) the constant region, or a portion thereof, is altered, replaced or exchanged so that the variable region is linked to a constant region of a different or altered class, effector function and/or species; or (b) the variable region, or a portion thereof, is altered, replaced or exchanged with a variable region, or portion thereof, having a different or altered antigen specificity; or with corresponding sequences from another species or from another antibody class or subclass.

In the present invention, unless otherwise specified, the position of the complementary-determining regions (CDRs) is determined using the Kabat nomenclature.

According to some embodiments, the isolated anti-CD8α antibody, or the antigen-binding fragment thereof, as described herein comprises a variable region of the heavy chain (also referred to as heavy chain variable region or VH) which comprises at least one, preferably at least two, more preferably the three following CDRs:

$V_H$-CDR1: $NX_1X_2MN$, wherein
  $X_1$ is N or Y,
  $X_2$ is D or A or Y;
$V_H$-CDR2: $X_3ISGSSX_4YIX_5YADFVKG$ (SEQ ID NO: 1), wherein
  $X_3$ is D or S,
  $X_4$ is S or R,
  $X_5$ is D or G or Y; and/or
$V_H$-CDR3: $SSX_6X_7X_8X_9YX_{10}X_{11}X_{12}X_{13}MDV$ (SEQ ID NO: 2), wherein
  $X_6$ is N or no amino acid,
  $X_7$ is Y or no amino acid,
  $X_8$ is Y or G or no amino acid,
  $X_9$ is D or S or no amino acid,
  $X_{10}$ is S or N or F,
  $X_1$ is A or G,
  $X_{12}$ is S or D or N,
  $X_{13}$ is A or G.

Examples of $V_H$-CDR1 having an amino acid sequence corresponding to $NX_1X_2MN$ as described above include, without being limited to: NNAMN (SEQ ID NO: 6), NYDMN (SEQ ID NO: 12), and NYYMN (SEQ ID NO: 18). Thus, in some embodiments, the $V_H$-CDR1 having an amino acid sequence as set forth in sequence $NX_1X_2MN$ is selected from the group comprising or consisting of SEQ ID NO: 6, SEQ ID NO: 12, and SEQ ID NO: 18.

Examples of $V_H$-CDR2 having an amino acid sequence as set forth in SEQ ID NO: 1 as described above include, without being limited to, DISGSSRYIGYADFVKG (SEQ ID NO: 7), DISGSSSYIDYADFVKG (SEQ ID NO: 13), and SISGSSRYIYYADFVKG (SEQ ID NO: 19). Thus, in some embodiments, the $V_H$-CDR2 having an amino acid sequence as set forth in SEQ ID NO: 1 is selected from the group comprising or consisting of SEQ ID NO: 7, SEQ ID NO: 13, and SEQ ID NO: 19.

Examples of $V_H$-CDR3 having an amino acid sequence as set forth in SEQ ID NO: 2 as described above include, without being limited to, SSNYYDYNADAMDV (SEQ ID NO: 8), SSYYSGSGMDV (SEQ ID NO: 14), and SSGSYFGNAMDV (SEQ ID NO: 20). Thus, in some embodiments, the $V_H$-CDR3 having an amino acid sequence as set forth in SEQ ID NO: 2 is selected from the group comprising or consisting of SEQ ID NO: 8, SEQ ID NO: 14, and SEQ ID NO: 20.

In some embodiments, the isolated anti-CD8α antibody, or the antigen-binding fragment thereof, comprises a VH which comprises at least one (e.g., 1, 2 or 3) of the following CDRs, and preferably the three following CDRs:

- a $V_H$-CDR1 selected from the group comprising or consisting of NNAMN (SEQ ID NO: 6), NYDMN (SEQ ID NO: 12), and NYYMN (SEQ ID NO: 18);
- a $V_H$-CDR2 selected from the group comprising or consisting of DISGSSRYIGYADFVKG (SEQ ID NO: 7), DISGSSSYIDYADFVKG (SEQ ID NO: 13), and SISGSSRYIYYADFVKG (SEQ ID NO: 19); and/or
- a $V_H$-CDR3 selected from the group comprising or consisting of SSNYYDYNADAMDV (SEQ ID NO: 8), SSYYSGSGMDV (SEQ ID NO: 14), and SSGSYFGNAMDV (SEQ ID NO: 20).

In some embodiments, the isolated anti-CD8α antibody, or the antigen-binding fragment thereof, comprises a VH which comprises at least one (e.g., 1, 2 or 3) of the following CDRs, and preferably the three following CDRs:

$V_H$-CDR1: (SEQ ID NO: 6)
NNAMN;

$V_H$-CDR2: (SEQ ID NO: 7)
DISGSSRYIGYADFVKG;
and/or

-$V_H$-CDR3: (SEQ ID NO: 8)
SSNYYDYNADAMDV.

In some embodiments, the isolated anti-CD8α antibody, or the antigen-binding fragment thereof, comprises a VH which comprises at least one (e.g., 1, 2 or 3) of the following CDRs, and preferably the three following CDRs:

$V_H$-CDR1: (SEQ ID NO: 12)
NYDMN;

-continued $V_H$-CDR2: (SEQ ID NO: 13)
DISGSSSYIDYADFVKG;
and/or $V_H$-CDR3: (SEQ ID NO: 14)
SSYYSGSGMDV.

In some embodiments, the isolated anti-CD8α antibody, or the antigen-binding fragment thereof, comprises a VH which comprises at least one (e.g., 1, 2 or 3) of the following CDRs, and preferably the three following CDRs:

$V_H$-CDR1: (SEQ ID NO: 18)
NYYMN;

$V_H$-CDR2: (SEQ ID NO: 19)
SISGSSRYIYYADFVKG;
and/or $V_H$-CDR3: (SEQ ID NO: 20)
SSGSYFGNAMDV.

In some embodiments, $V_H$-CDR1, $V_H$-CDR2 and/or $V_H$-CDR3 have an amino acid sequence as set forth in any one of SEQ ID NOs 6-8, 12-14, and 18-20, as described above with 1, 2, or 3, or more amino acid(s) being substituted by a different amino acid. For example, in some embodiments, the isolated anti-CD8α antibody, or the antigen-binding fragment thereof, comprises a $V_H$-CDR1 having an amino acid sequence as set forth in SEQ ID NO: 6, SEQ ID NO: 12, or in SEQ ID NO: 18 with 1, 2, or 3, or more amino acid(s) being substituted by a different amino acid. In some embodiments, $V_H$-CDR1, $V_H$-CDR2 and/or $V_H$-CDR3 as described above have an amino acid sequence that shares at least 70%, 75%, 80%, 85%, 90%, 95%, 96%, 97%, 98%, or 99%, or more identity with the corresponding amino acid sequence as set forth in any one of SEQ ID NOs 6-8, 12-14, and 18-20. For example, in some embodiments, the isolated anti-CD8α antibody, or the antigen-binding fragment thereof, comprises a $V_H$-CDR1 having an amino acid sequence that shares at least 70%, 75%, 80%, 85%, 90%, 95%, 96%, 97%, 98%, or 99%, or more identity with the amino acid sequence as set forth in SEQ ID NO: 6, SEQ ID NO: 12, or in SEQ ID NO: 18.

According to some embodiments, the isolated anti-CD8α antibody, or the antigen-binding fragment thereof, comprises a variable region of the light chain (also referred to as light chain variable region or VL) which comprises at least one, preferably at least two, more preferably the three following CDRs:

$V_L$-CDR1: AGTSSDVGG$X_{14}X_{15}X_{16}$VS (SEQ ID NO: 3), wherein
- $X_{14}$ is G or N or Y,
- $X_{15}$ is S or Y,
- $X_{16}$ is S or Y;

$V_L$-CDR2: $X_{17}$DS$X_{18}$RPS (SEQ ID NO: 4), wherein
- $X_{17}$ is Q or S or Y,
- $X_{18}$ is Y or S; and/or $V_L$-CDR3: SS$X_{19}$T$X_{20}$YSTRV (SEQ ID NO: 5), wherein
- $X_{19}$ is Y or D,
- $X_{20}$ is Y or Q or S.

Examples of $V_L$-CDR1 having an amino acid sequence as set forth in SEQ ID NO: 3 as described above include, without being limited to, AGTSSDVGGNSYVS (SEQ ID NO: 9), AGTSSDVGGGSSVS (SEQ ID NO: 15), and AGTSSDVGGYYSVS (SEQ ID NO: 21). Thus, in some embodiments, the $V_L$-CDR1 having an amino acid sequence as set forth in SEQ ID NO: 3 is selected from the group comprising or consisting of SEQ ID NO: 9, SEQ ID NO: 15, and SEQ ID NO: 21.

Examples of $V_L$-CDR2 having an amino acid sequence as set forth in SEQ ID NO: 4 as described above include, without being limited to, SDSSRPS (SEQ ID NO: 10), QDSYRPS (SEQ ID NO: 16), and YDSSRPS (SEQ ID NO: 22). Thus, in some embodiments, the $V_L$-CDR2 having an amino acid sequence as set forth in SEQ ID NO: 4 is selected from the group comprising or consisting of SEQ ID NO: 10, SEQ ID NO: 16, and SEQ ID NO: 22.

Examples of $V_L$-CDR3 having an amino acid sequence as set forth in SEQ ID NO: 5 as described above include, without being limited to, SSYTQYSTRV (SEQ ID NO: 11), SSYTYYSTRV (SEQ ID NO: 17), and SSDTSYSTRV (SEQ ID NO: 23). Thus, in some embodiments, the $V_L$-CDR3 having an amino acid sequence as set forth in SEQ ID NO: 5 is selected from the group comprising or consisting of SEQ ID NO: 11, SEQ ID NO: 17, and SEQ ID NO: 23.

In some embodiments, the isolated anti-CD8α antibody, or the antigen-binding fragment thereof, comprises a VL which comprises at least one (e.g., 1, 2 or 3) of the following CDRs, and preferably the three following CDRs:

- a $V_L$-CDR1 selected from the group comprising or consisting of AGTSSDVGGNSYVS (SEQ ID NO: 9, AGTSSDVGGGSSVS (SEQ ID NO: 15), and AGTSSDVGGYYSVS (SEQ ID NO: 21);
- a $V_L$-CDR2 selected from the group comprising or consisting of SDSSRPS (SEQ ID NO: 10), QDSYRPS (SEQ ID NO: 16), and YDSSRPS (SEQ ID NO: 22); and/or
- a $V_L$-CDR3 selected from the group comprising or consisting of SSYTQYSTRV (SEQ ID NO: 11), SSYTYYSTRV (SEQ ID NO: 17), and SSDTSYSTRV (SEQ ID NO: 23).

In some embodiments, the isolated anti-CD8α antibody, or the antigen-binding fragment thereof, comprises a VL which comprises at least one (e.g., 1, 2 or 3) of the following CDRs, and preferably the three following CDRs:

$V_L$-CDR1: (SEQ ID NO: 9)
AGTSSDVGGNSYVS;

$V_L$-CDR2: (SEQ ID NO: 10)
SDSSRPS;
and/or $V_L$-CDR3: (SEQ ID NO: 11)
SSYTQYSTRV.

In some embodiments, the isolated anti-CD8α antibody, or the antigen-binding fragment thereof, comprises a VL which comprises at least one (e.g., 1, 2 or 3) of the following CDRs, and preferably the three following CDRs:

$V_L$-CDR1: (SEQ ID NO: 15)
AGTSSDVGGGSSVS;

$V_L$-CDR2:

-continued $V_L$-CDR2: (SEQ ID NO: 16)
QDSYRPS;
and/or $V_L$-CDR3: (SEQ ID NO: 17)
SSYTYYSTRV.

In some embodiments, the isolated anti-CD8α antibody, or the antigen-binding fragment thereof, comprises a VL which comprises at least one (e.g., 1, 2 or 3) of the following CDRs, and preferably the three following CDRs:

$V_L$-CDR1: (SEQ ID NO: 21)
AGTSSDVGGYYSVS;

$V_L$-CDR2: (SEQ ID NO: 22)
YDSSRPS;
and/or $V_L$-CDR3: (SEQ ID NO: 23)
SSDTSYSTRV.

In some embodiments, $V_L$-CDR1, $V_L$-CDR2 and/or $V_L$-CDR3 have an amino acid sequence as set forth in any one of SEQ ID NOs 9-11, 15-17, and 21-23 as described above with 1, 2, 3 or more amino acid(s) being substituted by a different amino acid. For example, in some embodiments, the isolated anti-CD8α antibody, or the antigen-binding fragment thereof, comprises a $V_L$-CDR1 having an amino acid sequence as set forth in SEQ ID NO: 9, SEQ ID NO: 15, or in SEQ ID NO: 21 with 1, 2, or 3, or more amino acid(s) being substituted by a different amino acid. In some embodiments, $V_L$-CDR1, $V_L$-CDR2 and/or $V_L$-CDR3 as described above have an amino acid sequence that shares at least 70%, 75%, 80%, 85%, 90%, 95%, 96%, 97%, 98%, or 99%, or more identity with the corresponding amino acid sequence as set forth in any one of SEQ ID NOs 9-11, 15-17, and 21-23. For example, in some embodiments, the isolated anti-CD8α antibody, or the antigen-binding fragment thereof, comprises a $V_L$-CDR1 having an amino acid sequence that shares at least 70%, 75%, 80%, 85%, 90%, 95%, 96%, 97%, 98%, or 99%, or more identity with the amino acid sequence as set forth in SEQ ID NO: 9, SEQ ID NO: 15, or in SEQ ID NO: 21.

In some embodiments, the isolated anti-CD8α antibody, or the antigen-binding fragment thereof, comprises:

a variable region of the heavy chain (VH) which comprises at least one, preferably at least two, more preferably the three following CDRs:

$V_H$-CDR1: $NX_1X_2MN$, wherein
$X_1$ is N or Y,
$X_2$ is D or A or Y;
$V_H$-CDR2: $X_3ISGSSX_4YIX_5YADFVKG$ (SEQ ID NO: 1), wherein
$X_3$ is D or S,
$X_4$ is S or R,
$X_5$ is D or G or Y; and/or
$V_H$-CDR3: $SSX_6X_7X_8X_9YX_{10}X_{11}X_{12}X_{13}MDV$ (SEQ ID NO: 2), wherein
$X_6$ is N or no amino acid,
$X_7$ is Y or no amino acid,
$X_8$ is Y or G or no amino acid,
$X_9$ is D or S or no amino acid,
$X_{10}$ is S or N or F,
$X_{11}$ is A or G,
$X_{12}$ is S or D or N,
$X_{13}$ is A or G; and a variable region of the light chain (VL) which comprises at least one, preferably at least two, more preferably the three following CDRs:

VL-CDR1: $AGTSSDVGGX_{14}X_{15}X_{16}VS$ (SEQ ID NO: 3), wherein
$X_{14}$ is G or N or Y,
$X_{15}$ is S or Y,
$X_{16}$ is S or Y;
VL-CDR2: $X_{17}DSX_{18}RPS$ (SEQ ID NO: 4), wherein
$X_{17}$ is Q or S or Y,
$X_{18}$ is Y or S; and/or
VL-CDR3: $SSX_{19}TX_{20}YSTRV$ (SEQ ID NO: 5), wherein
$X_{19}$ is Y or D,
$X_{20}$ is Y or Q or S.

In some embodiments, the isolated anti-CD8α antibody, or the antigen-binding fragment thereof, comprises:

a VH which comprises the three following CDRs:

$V_H$-CDR1: $NX_1X_2MN$, wherein
$X_1$ is N or Y,
$X_2$ is D or A or Y;
$V_H$-CDR2: $X_3ISGSSX_4YIX_5YADFVKG$ (SEQ ID NO: 1), wherein
$X_3$ is D or S,
$X_4$ is S or R,
$X_8$ is D or G or Y; and
$V_H$-CDR3: $SSX_6X_7X_8X_9YX_{10}XlnX_{12}X_{13}MDV$ (SEQ ID NO: 2), wherein
$X_6$ is N or no amino acid,
$X_7$ is Y or no amino acid,
$X_8$ is Y or G or no amino acid,
$X_9$ is D or S or no amino acid,
$X_{10}$ is S or N or F,
$X_1$ is A or G,
$X_{12}$ is S or D or N,
$X_{13}$ is A or G; and a VL which comprises the three following CDRs:

VL-CDR1: $AGTSSDVGGX_{14}X_{15}X_{16}VS$ (SEQ ID NO: 3), wherein
$X_{14}$ is G or N or Y,
$X_{15}$ is S or Y,
$X_{16}$ is S or Y;
VL-CDR2: $X_{17}DSX_{18}RPS$ (SEQ ID NO: 4), wherein
$X_{17}$ is Q or S or Y,
$X_{18}$ is Y or S,
VL-CDR3: $SSX_{19}TX_{20}YSTRV$ (SEQ ID NO: 5), wherein
$X_{19}$ is Y or D,
$X_{20}$ is Y or Q or S.

In some embodiments, the isolated anti-CD8α antibody, or the antigen-binding fragment thereof, comprises:

a VH which comprises the three following CDRs:

a $V_H$-CDR1 selected from the group comprising or consisting of NNAMN (SEQ ID NO: 6), NYDMN (SEQ ID NO: 12), and NYYMN (SEQ ID NO: 18);
a $V_H$-CDR2 selected from the group comprising or consisting of DISGSSRYIGYADFVKG (SEQ ID NO: 7), DISGSSSYIDYADFVKG (SEQ ID NO: 13), and SISGSSRYIYYADFVKG (SEQ ID NO: 19); and
a $V_H$-CDR3 selected from the group comprising or consisting of SSNYYDYNADAMDV (SEQ ID NO: 8), SSYYSGSGMDV (SEQ ID NO: 14), and SSGSYFGNAMDV (SEQ ID NO: 20); and a VL which comprises the three following CDRs:

- a $V_L$-CDR1 selected from the group comprising or consisting of AGTSSDVGGNSYVS (SEQ ID NO: 9), AGTSSDVGGGSSVS (SEQ ID NO: 15), and AGTSSDVGGYYSVS (SEQ ID NO: 21);
- a $V_L$-CDR2 selected from the group comprising or consisting of SDSSRPS (SEQ ID NO: 10), QDSYRPS (SEQ ID NO: 16), and YDSSRPS (SEQ ID NO: 22); and
- a $V_L$-CDR3 selected from the group comprising or consisting of SSYTQYSTRV (SEQ ID NO: 11), SSYTYYSTRV (SEQ ID NO: 17), and SSDTSYSTRV (SEQ ID NO: 23).

In some embodiments, the isolated anti-CD8α antibody, or the antigen-binding fragment thereof, comprises the six following CDRs:

```
VH-CDR1:
                              (SEQ ID NO: 6)
NNAMN,

VH-CDR2:
                              (SEQ ID NO: 7)
DISGSSRYIGYADFVKG,

VH-CDR3:
                              (SEQ ID NO: 8)
SSNYYDYNADAMDV,

VL-CDR1:
                              (SEQ ID NO: 9)
AGTSSDVGGNSYVS,

VL-CDR2:
                              (SEQ ID NO: 10)
SDSSRPS,
and

VL-CDR3:
                              (SEQ ID NO: 11)
SSYTQYSTRV;
or

VH-CDR1:
                              (SEQ ID NO: 12)
NYDMN,

VH-CDR2:
                              (SEQ ID NO: 13)
DISGSSSYIDYADFVKG,

VH-CDR3:
                              (SEQ ID NO: 14)
SSYYSGSGMDV,

VL-CDR1:
                              (SEQ ID NO: 15)
AGTSSDVGGGSSVS,

VL-CDR2:
                              (SEQ ID NO: 16)
QDSYRPS,
and

VL-CDR3:
                              (SEQ ID NO: 17)
SSYTYYSTRV;
or

VH-CDR1:
                              (SEQ ID NO: 18)
NYYMN,
```

-continued

```
VH-CDR2:
                              (SEQ ID NO: 19)
SISGSSRYIYYADFVKG,

VH-CDR3:
                              (SEQ ID NO: 20)
SSGSYFGNAMDV,

VL-CDR1:
                              (SEQ ID NO: 21)
AGTSSDVGGYYSVS,

VL-CDR2:
                              (SEQ ID NO: 22)
YDSSRPS,
and

VL-CDR3:
                              (SEQ ID NO: 23)
SSDTSYSTRV.
```

In some embodiments, the isolated anti-CD8α antibody, or the antigen-binding fragment thereof, comprises:

a VH which comprises the three following CDRs:

```
VH-CDR1:
                              (SEQ ID NO: 6)
NNAMN,

VH-CDR2:
                              (SEQ ID NO: 7)
DISGSSRYIGYADFVKG,
and

VH-CDR3:
                              (SEQ ID NO: 8)
SSNYYDYNADAMDV;
```

and a VL which comprises the three following CDRs:

```
VL-CDR1:
                              (SEQ ID NO: 9)
AGTSSDVGGNSYVS,

VL-CDR2:
                              (SEQ ID NO: 10)
SDSSRPS,
and

VL-CDR3:
                              (SEQ ID NO: 11)
SSYTQYSTRV.
```

In some embodiments, the isolated anti-CD8α antibody, or the antigen-binding fragment thereof, comprises CDRs having an amino acid sequence as set forth in SEQ ID NOs: 6-11 as described above with 1, 2, 3 or more amino acid(s) being substituted by a different amino acid. In some embodiments, the isolated anti-CD8α antibody, or the antigen-binding fragment thereof, comprises CDRs as described above having an amino acid sequence that shares at least 70%, 75%, 80%, 85%, 90%, 95%, 96%, 97%, 98%, or 99%, or more identity with the corresponding amino acid sequence as set forth in SEQ ID NOs: 6-11.

An example of anti-CD8α antibody comprising a VH comprising $V_H$-CDR1, $V_H$-CDR2 and $V_H$-CDR3 as set forth in SEQ ID NOs: 6, 7 and 8, respectively, and a VL comprising $V_L$-CDR1, $V_L$-CDR2 and $V_L$-CDR3 as set forth in SEQ ID NOs: 9, 10 and 11, respectively, is hMP08-R3-F08.

In some embodiments, the isolated anti-CD8α antibody, or the antigen-binding fragment thereof, comprises:

a VH which comprises the three following CDRs:

```
VH-CDR1:                    (SEQ ID NO: 12)
NYDMN,

VH-CDR2:                    (SEQ ID NO: 13)
DISGSSSYIDYADFVKG,
and

VH-CDR3:                    (SEQ ID NO: 14)
SSYYSGSGMDV;
```

and a VL which comprises the three following CDRs:

```
VL-CDR1:                    (SEQ ID NO: 15)
AGTSSDVGGGSSVS,

VL-CDR2:                    (SEQ ID NO: 16)
QDSYRPS,
and

VL-CDR3:                    (SEQ ID NO: 17)
SSYTYYSTRV.
```

In some embodiments, the isolated anti-CD8α antibody, or the antigen-binding fragment thereof, comprises CDRs having an amino acid sequence as set forth in SEQ ID NOs: 12-17 as described above with 1, 2, 3 or more amino acid(s) being substituted by a different amino acid. In some embodiments, the isolated anti-CD8α antibody, or the antigen-binding fragment thereof, comprises CDRs as described above having an amino acid sequence that shares at least 70%, 75%, 80%, 85%, 90%, 95%, 96%, 97%, 98%, or 99%, or more identity with the corresponding amino acid sequence as set forth in SEQ ID NOs: 12-17.

An example of anti-CD8α antibody comprising a VH comprising $V_H$-CDR1, $V_H$-CDR2 and $V_H$-CDR3 as set forth in SEQ ID NOs: 12, 13 and 14, respectively, and a VL comprising $V_L$-CDR1, $V_L$-CDR2 and $V_L$-CDR3 as set forth in SEQ ID NOs: 15, 16 and 17, respectively, is hMP08-R3-C11.

In some embodiments, the isolated anti-CD8α antibody, or the antigen-binding fragment thereof, comprises:

a VH which comprises the three following CDRs:

```
VH-CDR1:                    (SEQ ID NO: 18)
NYYMN,

VH-CDR2:                    (SEQ ID NO: 19)
SISGSSRYIYYADFVKG,
and

VH-CDR3:                    (SEQ ID NO: 20)
SSGSYFGNAMDV;
```

and a VL which comprises the three following CDRs:

```
VL-CDR1:                    (SEQ ID NO: 21)
AGTSSDVGGYYSVS,
```

-continued

```
VL-CDR2:                    (SEQ ID NO: 22)
YDSSRPS,
and

VL-CDR3:                    (SEQ ID NO: 23)
SSDTSYSTRV.
```

In some embodiments, the isolated anti-CD8α antibody, or the antigen-binding fragment thereof, comprises CDRs having an amino acid sequence as set forth in SEQ ID NOs: 18-23 as described above with 1, 2, 3 or more amino acid(s) being substituted by a different amino acid. In some embodiments, the isolated anti-CD8α antibody, or the antigen-binding fragment thereof, comprises CDRs as described above having an amino acid sequence that shares at least 70%, 75%, 80%, 85%, 90%, 95%, 96%, 97%, 98%, or 99%, or more identity with the corresponding amino acid sequence as set forth in SEQ ID NOs: 18-23.

An example of anti-CD8α antibody comprising a VH comprising $V_H$-CDR1, $V_H$-CDR2 and $V_H$-CDR3 as set forth in SEQ ID NOs: 18, 19 and 20, respectively, and a VL comprising $V_L$-CDR1, $V_L$-CDR2 and $V_L$-CDR3 as set forth in SEQ ID NOs: 21, 22 and 23, respectively, is hMP09-R3-D03.

According to some embodiments, the isolated anti-CD8α antibody, or the antigen-binding fragment thereof, comprises a variable region of the heavy chain (VH) comprising or consisting of a sequence selected from the group comprising or consisting of SEQ ID NO: 24, SEQ ID NO: 26, SEQ ID NO: 28, and sequences having at least 70%, 75%, 80%, 85%, 90%, 95%, 96%, 97%, 98%, or 99%, or more identity with SEQ ID NO: 24, SEQ ID NO: 26, or SEQ ID NO: 28.

In some embodiments, the isolated anti-CD8α antibody, or the antigen-binding fragment thereof, comprises a VH comprising or consisting of a sequence selected from the group comprising or consisting of SEQ ID NO: 24, SEQ ID NO: 26, and SEQ ID NO: 28, with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid. In some embodiments, the isolated anti-CD8α antibody, or the antigen-binding fragment thereof, comprises a VH comprising or consisting of a sequence selected from the group comprising or consisting of SEQ ID NO: 24, SEQ ID NO: 26, and SEQ ID NO: 28, with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid, wherein said amino acid substitution(s) do(es) not occur in any of the three CDRs ($_{VH}$-CDR1, $_{VH}$-CDR2, and $_{VH}$-CDR3).

In some embodiments, the isolated anti-CD8α antibody, or the antigen-binding fragment thereof, comprises a VH comprising or consisting an amino acid sequence that shares at least 70%, 75%, 80%, 85%, 90%, 95%, 96%, 97%, 98%, or 99%, or more identity with SEQ ID NO: 24, SEQ ID NO: 26, or SEQ ID NO: 28. In some embodiments, the isolated anti-CD8α antibody, or the antigen-binding fragment thereof, comprises a VH comprising an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 24, SEQ ID NO: 26, or SEQ ID NO: 28. In some embodiments, the isolated anti-CD8α antibody, or the antigen-binding fragment thereof, comprises a VH comprising three CDRs ($_{VH}$-CDR1, $_{VH}$-CDR2, and $_{VH}$-CDR3) as described above and an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 24, SEQ ID NO: 26, or SEQ ID NO: 28.

In some embodiments, the isolated anti-CD8α antibody, or the antigen-binding fragment thereof, comprises a VH comprising or consisting of a sequence selected from the group comprising or consisting of SEQ ID NO: 24, SEQ ID NO: 26, and SEQ ID NO: 28.

According to some embodiments, the isolated anti-CD8α antibody, or the antigen-binding fragment thereof, comprises a variable region of the light chain (VL) comprising or consisting of a sequence selected from the group comprising or consisting of SEQ ID NO: 25, SEQ ID NO: 27, SEQ ID NO: 29 and sequences having at least 70%, 75%, 80%, 85%, 90%, 95%, 96%, 97%, 98%, or 99%, or more identity with SEQ ID NO: 25, SEQ ID NO: 27, or SEQ ID NO: 29.

In some embodiments, the isolated anti-CD8α antibody, or the antigen-binding fragment thereof, comprises a VL comprising or consisting of a sequence selected from the group comprising or consisting of SEQ ID NO: 25, SEQ ID NO: 27, and SEQ ID NO: 29, with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid. In some embodiments, the isolated anti-CD8α antibody, or the antigen-binding fragment thereof, comprises a VL comprising or consisting of a sequence selected from the group comprising or consisting of SEQ ID NO: 25, SEQ ID NO: 27, and SEQ ID NO: 29, with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid, wherein said amino acid substitution(s) do(es) not occur in any of the three CDRs ($_{VL}$-CDR1, $_{VL}$-CDR2, and $_{VL}$-CDR3).

In some embodiments, the isolated anti-CD8α antibody, or the antigen-binding fragment thereof, comprises a VL comprising or consisting an amino acid sequence that shares at least 70%, 75%, 80%, 85%, 90%, 95%, 96%, 97%, 98%, or 99%, or more identity with SEQ ID NO: 25, SEQ ID NO: 27, or SEQ ID NO: 29. In some embodiments, the isolated anti-CD8α antibody, or the antigen-binding fragment thereof, comprises a VL comprising an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 25, SEQ ID NO: 27, or SEQ ID NO: 29. In some embodiments, the isolated anti-CD8α antibody, or the antigen-binding fragment thereof, comprises a VL comprising three CDRs ($_{VL}$-CDR1, $_{VL}$-CDR2, and $_{VL}$-CDR3) as described above and an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 25, SEQ ID NO: 27, or SEQ ID NO: 29.

In some embodiments, the isolated anti-CD8α antibody, or the antigen-binding fragment thereof, comprises a VL comprising or consisting of a sequence selected from the group comprising or consisting of SEQ ID NO: 25, SEQ ID NO: 27, and SEQ ID NO: 29.

According to some embodiments, the isolated anti-CD8α antibody, or the antigen-binding fragment thereof, comprises:

- a variable region of the heavy chain (VH) comprising or consisting of a sequence selected from the group comprising or consisting of SEQ ID NO: 24, SEQ ID NO: 26, SEQ ID NO: 28, and sequences having at least 70%, 75%, 80%, 85%, 90%, 95%, 96%, 97%, 98%, or 99%, or more identity with SEQ ID NO: 24, SEQ ID NO: 26, or SEQ ID NO: 28; and
- a variable region of the light chain (VL) comprising or consisting of a sequence selected from the group comprising or consisting of SEQ ID NO: 25, SEQ ID NO: 27, SEQ ID NO: 29 and sequences having at least 70%, 75%, 80%, 85%, 90%, 95%, 96%, 97%, 98%, or 99%, or more identity with SEQ ID NO: 25, SEQ ID NO: 27, or SEQ ID NO: 29.

In some embodiments, the isolated anti-CD8α antibody, or the antigen-binding fragment thereof, comprises:

- a VH comprising three CDRs ($_{VH}$-CDR1, $_{VH}$-CDR2, and $_{VH}$-CDR3) as described above and an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 24, SEQ ID NO: 26, or SEQ ID NO: 28; and
- a VL comprising three CDRs ($_{VL}$-CDR1, $_{V}$L-CDR2, and $_{VL}$-CDR3) as described above and an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 25, SEQ ID NO: 27, or SEQ ID NO: 29.

In some embodiments, the isolated anti-CD8α antibody, or the antigen-binding fragment thereof, comprises:

- a VH comprising or consisting of a sequence as set forth in SEQ ID NO: 24 or a sequence having at least 70%, 75%, 80%, 85%, 90%, 95%, 96%, 97%, 98%, or 99%, or more identity with SEQ ID NO: 24; and
- a VL comprising or consisting of a sequence selected from the group comprising or consisting of SEQ ID NO: 25, SEQ ID NO: 27, SEQ ID NO: 29, and sequences having at least 70%, 75%, 80%, 85%, 90%, 95%, 96%, 97%, 98%, or 99%, or more identity with SEQ ID NO: 25, SEQ ID NO: 27, or SEQ ID NO: 29.

In some embodiments, the isolated anti-CD8α antibody, or the antigen-binding fragment thereof, comprises:

- a VH comprising three CDRs ($_{VH}$-CDR1, $_{VH}$-CDR2, and $_{VH}$-CDR3) as described above and an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 24; and
- a VL comprising three CDRs ($_{VL}$-CDR1, $_{VL}$-CDR2, and $_{VL}$-CDR3) as described above and an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 25, SEQ ID NO: 27, or SEQ ID NO: 29.

In some embodiments, the isolated anti-CD8α antibody, or the antigen-binding fragment thereof, comprises:

- a VH comprising or consisting of a sequence as set forth in SEQ ID NO: 26 or a sequence having at least 70%, 75%, 80%, 85%, 90%, 95%, 96%, 97%, 98%, or 99%, or more identity with SEQ ID NO: 26; and
- a VL comprising or consisting of a sequence selected from the group comprising or consisting of SEQ ID NO: 25, SEQ ID NO: 27, SEQ ID NO: 29 and sequences having at least 70%, 75%, 80%, 85%, 90%, 95%, 96%, 97%, 98%, or 99%, or more identity with SEQ ID NO: 25, SEQ ID NO: 27, or SEQ ID NO: 29.

In some embodiments, the isolated anti-CD8α antibody, or the antigen-binding fragment thereof, comprises:

- a VH comprising three CDRs ($_{VH}$-CDR1, $_{VH}$-CDR2, and $_{VH}$-CDR3) as described above and an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 26; and
- a VL comprising three CDRs ($_{VL}$-CDR1, $_{VL}$-CDR2, and $_{VL}$-CDR3) as described above and an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 25, SEQ ID NO: 27, or SEQ ID NO: 29.

In some embodiments, the isolated anti-CD8α antibody, or the antigen-binding fragment thereof, comprises:

- a VH comprising or consisting of a sequence as set forth in SEQ ID NO: 28 or a sequence having at least 70%, 75%, 80%, 85%, 90%, 95%, 96%, 97%, 98%, or 99%, or more identity with SEQ ID NO: 28; and
- a VL comprising or consisting of a sequence selected from the group comprising or consisting of SEQ ID NO: 25, SEQ ID NO: 27, SEQ ID NO: 29, and sequences having at least 70%, 75%, 80%, 85%, 90%, 95%, 96%, 97%, 98%, or 99%, or more identity with SEQ ID NO: 25, SEQ ID NO: 27, or SEQ ID NO: 29.

In some embodiments, the isolated anti-CD8α antibody, or the antigen-binding fragment thereof, comprises:

- a VH comprising three CDRs ($_{VH}$-CDR1, $_{VH}$-CDR2, and $_{VH}$-CDR3) as described above and an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 28; and
- a VL comprising three CDRs ($_{V}$L-CDR1, $_{VL}$-CDR2, and $_{VL}$-CDR3) as described above and an amino acid sequence of the framework regions (i.e., the non-CDR regions) that shares at least 70%, 75%, 80%, 85%, 90%, 95%, 96%, 97%, 98%, or 99%, or more identity with the amino acid sequence of the framework regions (i.e., the non-CDR regions) of SEQ ID NO: 25, SEQ ID NO: 27, or SEQ ID NO: 29.

According to some embodiments, the isolated anti-CD8α antibody, or the antigen-binding fragment thereof, comprises:

- a VH comprising or consisting of SEQ ID NO: 24, or a sequence having at least 70%, 75%, 80%, 85%, 90%, 95%, 96%, 97%, 98%, or 99%, or more identity with SEQ ID NO: 24, and a VL comprising or consisting of SEQ ID NO: 25, or a sequence having at least 70%, 75%, 80%, 85%, 90%, 95%, 96%, 97%, 98%, or 99%, or more identity with SEQ ID NO: 25; or
- a VH comprising or consisting of SEQ ID NO: 26, or a sequence having at least 70%, 75%, 80%, 85%, 90%, 95%, 96%, 97%, 98%, or 99%, or more identity with SEQ ID NO: 26, and a VL comprising or consisting of SEQ ID NO: 27, or a sequence having at least 70%, 75%, 80%, 85%, 90%, 95%, 96%, 97%, 98%, or 99%, or more identity with SEQ ID NO: 27; or
- a VH comprising or consisting of SEQ ID NO: 28, or a sequence having at least 70%, 75%, 80%, 85%, 90%, 95%, 96%, 97%, 98%, or 99%, or more identity with SEQ ID NO: 28, and a VL comprising or consisting of SEQ ID NO: 29, or a sequence having at least 70%, 75%, 80%, 85%, 90%, 95%, 96%, 97%, 98%, or 99%, or more identity with SEQ ID NO: 29.

In some embodiments, the isolated anti-CD8α antibody, or the antigen-binding fragment thereof, comprises:

- a VH comprising or consisting of SEQ ID NO: 24, or a sequence having at least 70%, 75%, 80%, 85%, 90%, 95%, 96%, 97%, 98%, or 99%, or more identity with SEQ ID NO: 24; and
- a VL comprising or consisting of SEQ ID NO: 25, or a sequence having at least 70%, 75%, 80%, 85%, 90%, 95%, 96%, 97%, 98%, or 99%, or more identity with SEQ ID NO: 25.

An example of anti-CD8α antibody comprising a VH as set forth in SEQ ID NO: 24, and a VL as set forth in SEQ ID NO: 25, is hMP08-R3-F08.

In some embodiments, the isolated anti-CD8α antibody, or the antigen-binding fragment thereof, comprises:

- a VH comprising or consisting of SEQ ID NO: 26, or a sequence having at least 70%, 75%, 80%, 85%, 90%, 95%, 96%, 97%, 98%, or 99%, or more identity with SEQ ID NO: 26; and
- a VL comprising or consisting of SEQ ID NO: 27, or a sequence having at least 70%, 75%, 80%, 85%, 90%, 95%, 96%, 97%, 98%, or 99%, or more identity with SEQ ID NO: 27.

An example of anti-CD8α antibody comprising a VH as set forth in SEQ ID NO: 26, and a VL as set forth in SEQ ID NO: 27, is hMP08-R3-C11.

In some embodiments, the isolated anti-CD8α antibody, or the antigen-binding fragment thereof, comprises:

- a VH comprising or consisting of SEQ ID NO: 28, or a sequence having at least 70%, 75%, 80%, 85%, 90%, 95%, 96%, 97%, 98%, or 99%, or more identity with SEQ ID NO: 28; and
- a VL comprising or consisting of SEQ ID NO: 29, or a sequence having at least 70%, 75%, 80%, 85%, 90%, 95%, 96%, 97%, 98%, or 99%, or more identity with SEQ ID NO: 29.

An example of anti-CD8α antibody comprising a VH as set forth in SEQ ID NO: 28, and a VL as set forth in SEQ ID NO: 29, is hMP09-R3-D03.

Another object of the present invention is a fusion protein comprising the anti-CD8α antibody, or the antigen-binding fragment thereof, as described herein.

Another object of the present invention is a nucleic acid encoding the anti-CD8α antibody, or the antigen-binding fragment thereof, as described herein. Another object of the present invention is a nucleic acid encoding the fusion protein as described herein.

In some embodiments, the nucleic acid is an isolated nucleic acid. In some embodiments, an "isolated nucleic acid" refers to a nucleic acid that is substantially separated from other nucleic acid sequences as well as proteins or complexes such as ribosomes and polymerases, which naturally accompany a native sequence. The term embraces a nucleic acid sequence that has been removed from its naturally occurring environment, and includes recombinant or cloned nucleic acid, chemically synthesized analogues, and analogues biologically synthesized by heterologous systems. A substantially pure nucleic acid includes isolated forms of the nucleic acid. This refers to the nucleic acid as originally isolated and does not exclude nucleic acid sequences later added to the isolated nucleic acid by the hand of man.

In some embodiments, the isolated nucleic acid is purified.

In some embodiments, the isolated nucleic acid is purified to (i) greater than about 80%, 85%, 90%, 91%, 92%, 93%, 94%, or 95%, or more by weight of nucleic acid as determined by absorbance methods or fluorescence methods (such as, for example, by measuring the ratio of absorbance at 260 and 280 nm (A260/280)), and most preferably to greater than about 96%, 97%, 98%, or 99% by weight; or (ii) homogeneity as shown by agarose gel electrophoresis and using an intercalating agent such as, for example, ethidium bromide, SYBR Green, GelGreen.

In some embodiments, the nucleic acid encodes at least a heavy chain variable region (VH) and/or a light chain variable region (VL) of the anti-CD8α antibody, or the antigen-binding fragment thereof, as described herein. In some embodiments, the nucleic acid encodes at least a VH and a VL of the anti-CD8α antibody, or the antigen-binding fragment thereof, as described herein on separate nucleic acid molecules or on the same nucleic acid molecule. The nucleic acid may encode variable and constant regions of the anti-CD8α antibody, or the antigen-binding fragment thereof, as described herein. The nucleic acid may encode heavy and light chains of the anti-CD8α antibody, or the antigen-binding fragment thereof, on separate nucleic acid molecules or on the same nucleic acid molecule.

According to some embodiments, the nucleic acid comprises or consists of a sequence encoding the VH of the anti-CD8α antibody, or the antigen-binding fragment thereof, as described above.

According to some embodiments, the nucleic acid comprises or consists of a sequence encoding the VL of the anti-CD8α antibody, or the antigen-binding fragment thereof, as described above.

According to some embodiments, the nucleic acid comprises or consists of:

- a sequence encoding the VH of the anti-CD8α antibody, or the antigen-binding fragment thereof, as described above; and/or
- a sequence encoding the VL of the anti-CD8α antibody, or the antigen-binding fragment thereof, as described above.

According to some embodiments, the nucleic acid comprises or consists of:

- a sequence encoding the VH of the anti-CD8α antibody, or the antigen-binding fragment thereof, said sequence being any one of SEQ ID NOs: 31, 33, or 35, or any sequence sharing at least 70%, 75%, 80%, 85%, 90%, 95%, 96%, 97%, 98%, or 99%, or more identity with SEQ ID NOs: 31, 33, or 35; and/or
- a sequence encoding the VL of the anti-CD8α antibody, or the antigen-binding fragment thereof, said sequence being any one of SEQ ID NOs: 32, 34, or 36, or any sequence sharing at least 70%, 75%, 80%, 85%, 90%, 95%, 96%, 97%, 98%, or 99%, or more identity with SEQ ID NOs: 32, 34, or 36.

According to some embodiments, the nucleic acid comprises or consists of:

- a sequence encoding the VH of the anti-CD8α antibody, or the antigen-binding fragment thereof, said sequence being SEQ ID NO: 31, or any sequence sharing at least 70%, 75%, 80%, 85%, 90%, 95%, 96%, 97%, 98%, or 99%, or more identity with SEQ ID NO: 31, and/or a sequence encoding the VL of the anti-CD8α antibody, or the antigen-binding fragment thereof, said sequence being SEQ ID NO: 32, or any sequence sharing at least 70%, 75%, 80%, 85%, 90%, 95%, 96%, 97%, 98%, or 99%, or more identity with SEQ ID NO: 32; or
- a sequence encoding the VH of the anti-CD8α antibody, or the antigen-binding fragment thereof, said sequence being SEQ ID NO: 33, or any sequence sharing at least 70%, 75%, 80%, 85%, 90%, 95%, 96%, 97%, 98%, or 99%, or more identity with SEQ ID NO: 33, and/or a sequence encoding the VL of the anti-CD8α antibody, or the antigen-binding fragment thereof, said sequence being SEQ ID NO: 34, or any sequence sharing at least 70%, 75%, 80%, 85%, 90%, 95%, 96%, 97%, 98%, or 99%, or more identity with SEQ ID NO: 34; or
- a sequence encoding the VH of the anti-CD8α antibody, or the antigen-binding fragment thereof, said sequence being SEQ ID NO: 35, or any sequence sharing at least 70%, 75%, 80%, 85%, 90%, 95%, 96%, 97%, 98%, or 99%, or more identity with SEQ ID NO: 35, and/or a sequence encoding the VL of the anti-CD8α antibody, or the antigen-binding fragment thereof, said sequence being SEQ ID NO: 36, or any sequence sharing at least 70%, 75%, 80%, 85%, 90%, 95%, 96%, 97%, 98%, or 99%, or more identity with SEQ ID NO: 36.

Typically, the nucleic acid described herein is a DNA (deoxyribonucleic acid) or RNA (ribonucleic acid) molecule, which may be included in any suitable vector.

Another object of the present invention is a vector, such as, for example, an expression vector or a cloning vector, comprising a nucleic acid encoding the anti-CD8α antibody, or the antigen-binding fragment thereof, or the fusion protein as described herein.

The terms "vector", "cloning vector" and "expression vector" mean the vehicle by which a nucleic acid sequence (e.g., a DNA molecule) encoding the anti-CD8α antibody, or the antigen-binding fragment thereof, or the fusion protein can be introduced into a host cell, so as to transform or transfect the host cell and promote expression (e.g., transcription and/or translation) of the introduced nucleic acid sequence.

In some embodiments, the vector, cloning vector, or expression vector, is a plasmid, a cosmid, an episome, an artificial chromosome, a phage, or a viral vector.

Examples of plasmids include replicating plasmids comprising an origin of replication, or integrative plasmids, such as for instance pUC, pcDNA, and pBR.

Examples of viral vector include adenoviral, adeno-associated virus (AAV), retroviral, herpes virus vectors. Such viral vectors may be produced by techniques known in the art, such as by transfecting packaging cells or by transient transfection with helper plasmids or viruses.

Any expression vector for animal cells can be used, so long as a nucleic acid encoding the anti-CD8α antibody, or the antigen-binding fragment thereof, or the fusion protein as described herein can be inserted and expressed.

The vector as described herein may comprise regulatory elements, such as a promoter, an enhancer, and/or a terminator, for example to cause or direct expression of the anti-CD8α antibody, or the antigen-binding fragment thereof, or the fusion protein upon introduction within a host cell or upon administration to a subject. Examples of promoters and enhancers used in expression vectors for animal cells include, but are not limited to, early promoter and enhancer of SV40, LTR promoter and enhancer of Moloney mouse leukemia virus, and promoter and enhancer of immunoglobulin H chain.

In some embodiments, the vector as described herein comprises a nucleic acid sequence encoding the variable region of the heavy chain (VH) of the anti-CD8α antibody, or the antigen-binding fragment thereof, as described above operably linked to regulatory elements. In some embodiments, the vector as described above comprises a sequence encoding the variable region of the light chain (VL) of the anti-CD8α antibody, or the antigen-binding fragment thereof, as described above operably linked to regulatory elements.

In some embodiments, the vector as described above is monocistronic. By "monocistronic", it is meant that a single nucleic acid is expressed with a single vector. In some embodiments, the vector as described above is polycistronic. By "polycistronic", it is meant that at least two or more nucleic acid sequences are expressed with a single vector.

Another object of the invention is a host cell comprising the vector as described herein. In some embodiments, the host cell is an isolated host cell. Said host cell may be used for the recombinant production of the anti-CD8α antibody, or the antigen-binding fragment thereof, or the fusion protein as described herein.

Host cells may be prokaryote cells, or eukaryote cells, such as, for example, yeast or mammalian cells.

It should be noted that, with regards to animal and human cells, the term "host cell" generally refers to a cell of a cultured cell line. Animals and human beings into whom a vector encoding the anti-CD8α antibody, or the antigen-binding fragment thereof, or the fusion protein as described herein, has been introduced are explicitly excluded from the definition of a "host cell".

Another object of the present invention is a method of producing, and optionally purifying, the isolated anti-CD8α antibody, or the antigen-binding fragment thereof, as described herein.

In some embodiments, the method comprises:
- introducing in vitro or ex vivo a nucleic acid or a vector as described herein into a host cell (that is to say transforming or transfecting a host cell with a nucleic acid or a vector as described herein);
- culturing in vitro or ex vivo host cells transformed or transfected with the nucleic acid or with the vector, under conditions suitable for expression of the anti-CD8α antibody, or the antigen-binding fragment thereof;
- optionally, selecting the host cells which express and/or secrete the anti-CD8α antibody, or the antigen-binding fragment thereof; and
- recovering the expressed and/or secreted anti-CD8α antibody, or the expressed and/or secreted antigen-binding fragment thereof.

Such a method is well-known in the art and can be used for large scale production of antibodies or antigen-binding fragments thereof, including monoclonal antibodies intended for in vitro, ex vivo and/or in vivo uses, such as therapeutic uses.

In some embodiments, the recovered anti-CD8α antibody, or the recovered antigen-binding fragment thereof, is further purified. Methods for purifying an antibody, or an antigen-binding fragment thereof, are well-known in the art and include, without limitation, use of an anti-CH1 antibody, protein A-Sepharose, gel electrophoresis, chromatography, in particular affinity chromatography.

Another object of the present invention is a composition comprising, consisting essentially of, or consisting of:
- at least one anti-CD8α antibody, or an antigen-binding fragment thereof, as described herein;
- at least one fusion protein as described herein,
- at least one nucleic acid encoding the anti-CD8α antibody, or the antigen-binding fragment thereof, or the fusion protein as described herein;
- at least one vector comprising such a nucleic acid molecule; or
- at least one host cell comprising such a vector.

As used herein, "consisting essentially of", with reference to a composition, means that the at least one anti-CD8α antibody, or the antigen-binding fragment thereof, fusion protein nucleic acid, vector, or host cell is the only active agent, therapeutic agent, or agent with a biologic activity within said composition.

Another object of the present invention is a pharmaceutical composition comprising, consisting essentially of, or consisting of:
- at least one anti-CD8α antibody, or an antigen-binding fragment thereof, as described herein;
- at least one fusion protein as described herein,
- at least one nucleic acid encoding the anti-CD8α antibody, or the antigen-binding fragment thereof, or the fusion protein as described herein;
- at least one vector comprising such a nucleic acid molecule; or
- at least one host cell comprising such a vector;

and at least one pharmaceutically acceptable excipient.

Pharmaceutically acceptable excipients that may be used in the pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

Another object of the present invention is a medicament comprising, consisting essentially of, or consisting of:
- at least one anti-CD8α antibody, or an antigen-binding fragment thereof, as described herein;
- at least one fusion protein as described herein,
- at least one nucleic acid encoding the anti-CD8α antibody, or the antigen-binding fragment thereof, or the fusion protein as described herein;
- at least one vector comprising such a nucleic acid molecule; or
- at least one host cell comprising such a vector.

In some embodiments, the composition, pharmaceutical composition, or medicament as described herein are formulated for administration to a subject.

The composition, pharmaceutical composition, or medicament as described herein may be administered or formulated to be administered systemically, orally, parenterally, by injection, topically, by inhalation spray, rectally, nasally, or via an implanted reservoir. The term administration used herein includes subcutaneous, intravenous, intramuscular, intra-articular, intra-synovial, intrasternal, intrathecal, intrahepatic, intralesional and intracranial injection or infusion techniques.

In some embodiments, the composition, pharmaceutical composition, or medicament as described herein are formulated for administration by injection, such as for example subcutaneous injection, or by infusion, such as for example intravenous infusion. Examples of forms adapted for injection include, but are not limited to, solutions, such as, for example, sterile aqueous solutions, gels, dispersions, emulsions, suspensions, solid forms suitable for using to prepare solutions or suspensions upon the addition of a liquid prior to use, such as, for example, powder, liposomal forms and the like.

In some embodiments, regimens or dosages used for administration of the composition, pharmaceutical composition, or medicament can be adapted as function of various parameters, and in particular as a function of the mode of administration used, of the relevant pathology, or of the desired duration of treatment. For example, it is well within the skill of the art to start with a dose at a level lower than those required to achieve the desired therapeutic effect and to gradually increase the dose of anti-CD8α antibody, an antigen-binding fragment thereof, or fusion protein as described herein until the desired effect is achieved. The dose of anti-CD8α antibody, an antigen-binding fragment thereof, or fusion protein as described herein may be varied over a wide range from 0.01 to 10 000 mg per adult per day. A composition, pharmaceutical composition or medicament typically may for example comprise from about 0.01 mg to about 10 000 mg, preferably from about 0.1 mg to about 5000 mg of anti-CD8α antibody, an antigen-binding fragment thereof, or fusion protein as described herein.

Another object of the present invention is an anti-CD8α antibody, or an antigen-binding fragment thereof, as described herein, for use as a medicament. Another object of the present invention is a fusion protein as described herein for use as a medicament.

Another object of the present invention is a nucleic acid encoding an anti-CD8α antibody, or an antigen-binding fragment thereof, or a fusion protein as described herein, or a vector comprising such a nucleic acid molecule, or a host cell comprising such a vector, for use as a medicament.

Another object of the present invention is an anti-CD8α antibody, or antigen binding fragment thereof, as described herein for use in the treatment of a CD8-related disease.

As used herein "CD8-related disease" refers to a disease, disorder or condition caused by or potentialized by an increased proportion of cells expressing CD8, in particular cells expressing CD8α, in a subject and/or by an increased level of expression of CD8, in particular CD8α, in cells of the subject.

Another object of the present invention is a fusion protein as described herein for use in the treatment of a CD8-related disease.

Another object of the present invention is a nucleic acid encoding an anti-CD8α antibody, or antigen binding fragment thereof, or a fusion protein as described herein, or a vector comprising such a nucleic acid molecule, or a host cell comprising such a vector, for use in the treatment of a CD8-related disease.

In some embodiments, the CD8-related disease is a cardiovascular disease. In some embodiments the cardiovascular disease is myocardial infarction or acute myocardial infarction.

Examples of cardiovascular diseases include, but are not limited to, myocardial infarction, acute myocardial infarction, post-myocardial infarction cardiac remodeling, post-myocardial infarction heart failure, stroke, coronary artery disease (i.e., atherosclerosis), acute coronary syndrome, myocarditis, and atrial fibrillation.

In some embodiments, the cardiovascular disease is selected from myocardial infarction, acute myocardial infarction, post-myocardial infarction cardiac remodeling, post-myocardial infarction heart failure, stroke, coronary artery disease, acute coronary syndrome, myocarditis, and atrial fibrillation.

Another object of the present invention is a method for treating a disease as described herein in a subject in need thereof, said method comprising administering to the subject at least one of:

- an anti-CD8α antibody, or an antigen binding fragment thereof, as described herein;
- a fusion protein as described herein;
- a nucleic acid as described herein encoding an anti-CD8α antibody, an antigen-binding fragment thereof, or a fusion protein;
- a vector as described herein comprising such a nucleic acid molecule; or
- a host cell as described herein comprising such a vector.

As mentioned above, in some embodiments, the disease to be treated is a CD8-related disease. In some embodiments, the disease to be treated is a cardiovascular disease, in particular myocardial infarction or acute myocardial infarction. In some embodiments, the cardiovascular disease is selected from myocardial infarction, acute myocardial infarction, post-myocardial infarction cardiac remodeling, post-myocardial infarction heart failure, stroke, coronary artery disease, acute coronary syndrome, myocarditis, and atrial fibrillation.

In some embodiments, the method comprises administering a therapeutically effective dose of the anti-CD8α antibody, or the antigen binding fragment thereof, as described herein; the fusion protein as described herein; the nucleic acid encoding as described herein an anti-CD8α antibody, an antigen-binding fragment thereof, or a fusion protein; the vector as described herein comprising such a nucleic acid molecule; or the host cell as described herein comprising such a vector.

A therapeutically effective dose may for example correspond to a dose ranging from 0.0001 mg/kg to about 100 mg/kg of body weight per day, preferably from 0.001 mg/kg to about 50 mg/kg of body weight per day. It will be appreciated that these doses are exemplary and that an optimal dosage can be adapted taking into account the affinity and tolerability of the anti-CD8α antibody, antigen-binding fragment, or fusion protein in the composition, pharmaceutical composition, or medicament.

The specific therapeutically effective dose level for any particular patient may depend upon a variety of factors including the disease being treated and the severity of the disease; activity of the isolated anti-CD8α antibody or antigen-binding fragment thereof, fusion protein, nucleic acid, expression vector, composition, pharmaceutical composition or medicament employed; the age, body weight, general health, sex and diet of the subject; the time of administration, route of administration, and rate of excretion of the specific anti-CD8α antibody or antigen-binding fragment thereof, fusion protein, nucleic acid, expression vector, composition, pharmaceutical composition or medicament employed; the duration of the treatment; drugs used in combination or coincidental with the specific isolated anti-CD8α antibody or antigen-binding fragment thereof, fusion protein, nucleic acid, expression vector, composition, pharmaceutical composition or medicament employed; and like factors well-known in the medical arts. For example, it is well within the skill of the art to start doses of the compound at levels lower than those required to achieve the desired therapeutic effect and to gradually increase the dosage until the desired effect is achieved. The total dose required for each treatment may be administered by multiple doses or in a single dose.

Another object of the present invention is a pharmaceutical composition for treating or for use in the treatment of a disease as described herein in a subject in need thereof, wherein said pharmaceutical composition comprises at least one of:

- an anti-CD8α antibody, or an antigen-binding fragment thereof, as described herein;
- a fusion protein as described herein;
- a nucleic acid as described herein encoding an anti-CD8α antibody, an antigen-binding fragment thereof, or a fusion protein;
- a vector as described herein comprising such a nucleic acid molecule; or
- a host cell as described herein comprising such a vector;

and a least one pharmaceutically acceptable excipient.

Another object of the present invention is the use of at least one of:

- an anti-CD8α antibody, or an antigen-binding fragment thereof, as described herein;
- a fusion protein as described herein;
- a nucleic acid as described herein encoding an anti-CD8α antibody, an antigen-binding fragment thereof, or a fusion protein;
- a vector as described herein comprising such a nucleic acid molecule; or
- a host cell as described herein comprising such a vector;

in the manufacture of a medicament for the treatment of a disease as described herein in a subject in need thereof.

As mentioned above, in some embodiments, the disease to be treated is a CD8-related disease. In some embodiments, the disease to be treated is a cardiovascular disease, in particular myocardial infarction or acute myocardial infarction. In some embodiments, the cardiovascular disease is selected from myocardial infarction, acute myocardial infarction, post-myocardial infarction cardiac remodeling, post-myocardial infarction heart failure, stroke, coronary artery disease, acute coronary syndrome, myocarditis, and atrial fibrillation.

The present invention further relates to the use of the isolated anti-CD8α antibody, or antigen binding fragment thereof, or fusion protein as described herein for depleting CD8α-expressing cells in a sample, and to an in vitro method for depleting CD8α-expressing cells in a sample, said method comprising a step of contacting said sample with the isolated anti-CD8α antibody, or antigen binding fragment thereof, or fusion protein as described herein.

As used herein, a "sample" refers to any biological material obtained via suitable methods known to the person skilled in the art from a subject. The sample may be collected in a clinically acceptable manner, e.g., in a way that cells, nucleic acids (such as DNA and RNA), proteins and/or extracellular vesicles are preserved. A "sample" may be a body tissue and/or a bodily fluid, preferably a bodily fluid. Examples of bodily fluids include, but are not limited to, blood, plasma, serum, lymph, ascetic fluid, cystic fluid, urine, bile, nipple exudate, vomitus, breast milk, tears, wound drainage, feces, vaginal secretions, synovial fluid, bronchoalveolar lavage fluid, sputum, amniotic fluid, peritoneal fluid, cerebrospinal fluid, pleural fluid, pericardial fluid, semen, saliva, sweat and alveolar macrophages, tissue lysates, biopsies and extracts prepared from diseased tissues.

In some embodiments, the sample is previously taken or retrieved from a subject, i.e., the methods as described herein do not comprise an active step of recovering a sample from the subject. Consequently, according to some embodiments, the methods as described herein are non-invasive methods, i.e., the methods of the invention are in vitro methods.

The invention further relates to the use of the isolated anti-CD8α antibody, or antigen binding fragment thereof, or fusion protein as described herein for detecting or quantifying CD8α in a sample, cell, tissue, organ, organism or subject; and to methods for detecting and/or quantifying CD8α in a sample, cell, tissue, organ, organism, or subject comprising contacting said sample, cell, tissue, or organ or administering said organism or subject with the isolated anti-CD8α antibody, or antigen binding fragment thereof, or fusion protein as described herein.

The uses and methods for detecting and/or quantifying CD8α may be in vitro or in vivo.

In some embodiments, the isolated anti-CD8α antibody, or antigen binding fragment thereof, as described herein is labeled for detection or diagnostic purposes.

Assays suitable for detecting or quantifying CD8α using the isolated anti-CD8α antibody, or antigen binding fragment thereof, or fusion protein as described herein are well-known in the art, and include ELISA, sandwich ELISA, RIA, FACS, tissue immunohistochemistry, Western-blot and immunoprecipitation.

TABLE OF SEQUENCES

| SEQ ID NO | Sequence function | Sequence |
|---|---|---|
| | Consensus VH-CDR1 | $NX_1X_2MN$<br>$X_1$ is N or Y<br>$X_2$ is D or A or Y |
| 1 | Consensus VH-CDR2 | $X_3ISGSSX_4YIX_5YADFVKG$<br>$X_3$ is D or S<br>$X_4$ is S or R<br>$X_5$ is D or G or Y |
| 2 | Consensus VH-CDR3 | $SSX_6X_7X_8X_9YX_{10}X_{11}X_{12}X_{13}MDV$<br>$X_6$ is N or no amino acid<br>$X_7$ is Y or no amino acid<br>$X_8$ is Y or G or no amino acid |

-continued

TABLE OF SEQUENCES

| SEQ ID NO | Sequence function | Sequence |
|---|---|---|
| | | $X_9$ is D or S or no amino acid<br>$X_{10}$ is S or N or F<br>$X_{11}$ is A or G<br>$X_{12}$ is S or D or N<br>$X_{13}$ is A or G |
| 3 | Consensus VL-CDR1 | AGTSSDVGG$\mathbf{X}_{14}\mathbf{X}_{15}\mathbf{X}_{16}$VS<br>$X_{14}$ is G or N or Y<br>$X_{15}$ is S or Y<br>$X_{16}$ is S or Y |
| 4 | Consensus VL-CDR2 | $X_{17}$DS$\mathbf{X}_{18}$RPS<br>$X_{17}$ is Q or S or Y<br>$X_{18}$ is Y or S |
| 5 | Consensus VL-CDR3 | SS$\mathbf{X}_{19}$T$\mathbf{X}_{20}$ YSTRV<br>$X_{19}$ is Y or D<br>$X_{20}$ is Y or Q or S |
| 6 | hMP08-R3-F08-VH-CDR1 | NNAMN |
| 7 | hMP08-R3-F08-VH-CDR2 | DISGSSRYIGYADFVKG |
| 8 | hMP08-R3-F08-VH-CDR3 | SSNYYDYNADAMDV |
| 9 | hMP08-R3-F08-VL-CDR1 | AGTSSDVGGNSYVS |
| 10 | hMP08-R3-F08-VL-CDR2 | SDSSRPS |
| 11 | hMP08-R3-F08-VL-CDR3 | SSYTQYSTRV |
| 12 | hMP08-R3-C11-VH-CDR1 | NYDMN |
| 13 | hMP08-R3-C11-VH-CDR2 | DISGSSSYIDYADFVKG |
| 14 | hMP08-R3-C11-VH-CDR3 | SSYYSGSGMDV |
| 15 | hMP08-R3-C11-VL-CDR1 | AGTSSDVGGGSSVS |
| 16 | hMP08-R3-C11-VL-CDR2 | QDSYRPS |
| 17 | hMP08-R3-C11-VL-CDR3 | SSYTYYSTRV |
| 18 | hMP09-R3-D03-VH-CDR1 | NYYMN |
| 19 | hMP09-R3-D03-VH-CDR2 | SISGSSRYIYYADFVKG |

-continued

TABLE OF SEQUENCES

| SEQ ID NO | Sequence function | Sequence |
|---|---|---|
| 20 | hMP09-R3-D03-VH-CDR3 | SSGSYFGNAMDV |
| 21 | hMP09-R3-D03-VL-CDR1 | AGTSSDVGGYYSVS |
| 22 | hMP09-R3-D03-VL-CDR2 | YDSSRPS |
| 23 | hMP09-R3-D03-VL-CDR3 | SSDTSYSTRV |
| 24 | hMP08-R3-F08-VH | EVQLVESGGSLVKPGGSLRLSCAASGFTFSNNAMNWVRQAP GKGLEWISDISGSSRYIGYADFVKGRFTISRDNAKNSLYLQM NSLRAEDTAVYYCVRSSNYYDYNADAMDVWGRGTLVTVS S |
| 25 | hMP08-R3-F08-VL | QSVLTQPASVSGSPGQSITISCAGTSSDVGGNSYVSWYQQHP GKAPKLMIYSDSSRPSGVSNRFSGSKSGNTASLTISGLQAEDE ADYYCSSYTQYSTRVFGGGTKLAVL |
| 26 | hMP08-R3-C11-VH | EVQLVESGGSLVKPGGSLRLSCAASGFTFSNYDMNWVRQAP GKGLEWISDISGSSSYIDYADFVKGRFTISRDNAKNSLYLQM NSLRAEDTAVYYCVRSSYYSGSGMDVWGRGTLVTVSS |
| 27 | hMP08-R3-C11-VL | QSVLTQPASVSGSPGQSITISCAGTSSDVGGGSSVSWYQQHP GKAPKLMIYQDSYRPSGVSNRFSGSKSGNTASLTISGLQAED EADYYCSSYTYYSTRVFGGGTKLAVL |
| 28 | hMP09-R3-D03-VH | EVQLVESGGSLVKPGGSLRLSCAASGFTFSNYYMNWVRQAP GKGLEWISSISGSSRYIYYADFVKGRFTISRDNAKNSLYLQM NSLRAEDTAVYYCVRSSGSYFGNAMDVWGRGTLVTVSS |
| 29 | hMP09-R3-D03-VL | QSVLTQPASVSGSPGQSITISCAGTSSDVGGYYSVSWYQQHP GKAPKLMIYYDSSRPSGVSNRFSGSKSGNTASLTISGLQAED EADYYCSSDTSYSTRVFGGGTKLAVL |
| 30 | Human CD8a (NCBI Reference Sequence: NP_001759.3) | MALPVTALLLPLALLLHAARPSQFRVSPLDRTWNLGETVEL KCQVLLSNPTSGCSWLFQPRGAAASPTFLLYLSQNKPKAAE GLDTQRFSGKRLGDTFVLTLSDFRRENEGYYFCSALSNSIMY FSHFVPVFLPAKPTTTPAPRPPTPAPTIASQPLSLRPEACRPAA GGAVHTRGLDFACDIYIWAPLAGTCGVLLLSLVITLYCNHRN RRRVCKCPRPVVKSGDKPSLSARYV |
| 31 | hMP08-R3-F08-VH nucleic acid | GCGGCCGCAAACTACAAGACAGACTTGCAAAAGAAGGCA TGCACAGCTCAGCACTGCTCTGTTGCCTGGTCCTCCTGACT GGGGTGAGGGCCGAGGTGCAGCTGGTGGAGAGCGGGGGC AGCCTGGTGAAGCCAGGGGGAAGCCTGAGGCTGAGCTGT GCCGCATCCGGGTTTACATTTTCCAACAACGCCATGAACT GGGTGAGGCAGGCACCCGGCAAAGGGCTGGAGTGGATTT CAGACATTTCCGGCAGTAGCAGATACATCGGCTACGCCGA CTTCGTGAAGGGCAGGTTCACAATCAGCAGAGACAACGC TAAGAACAGCCTGTACCTGCAGATGAACTCCCTGAGGGCC GAGGACACAGCCGTGTACTACTGCGTGAGGAGCTCCAAC TACTATGACTACAACGCCGACGCTATGGATGTGTGGGGAA GGGGCACCCTGGTGACCGTGAGCTCCGCTAGCACCAAGG GCCCATCGGTCTTCCCCCTGGCACCCTCCTCCAAGAGCAC CTCTGGGGGCACAGCGGCCCTGGGCTGCCTGGTCAAGGA CTACTTCCCCGAACCGGTGACGGTGTCGTGGAACTCAGGC GCCCTGACCAGCGGCGTGCACACCTTCCCGGCTGTCCTAC AGTCCTCAGGACTCTACTCCCTCAGCAGCGTGGTGACCGT GCCCTCCAGCAGCTTGGGCACCCAGACCTACATCTGCAAC GTGAATCACAAGCCCAGCAACACCAAGGTGGACAAGAAA GTTGAGCCCAAATCTTGTGACAAAACTCACACATGCCCAC CGTGCCCAGCACCTGAACTCCTGGGGGGACCGTCAGTCTT CCTCTTCCCCCCAAAACCCAAGGACACCCTCATGATCTCC CGGACCCCCGAGGTCACATGCGTGGTGGTGGACGTGAGC CACGAAGACCCTGAGGTCAAGTTCAACTGGTACGTGGAC |

-continued

TABLE OF SEQUENCES

| SEQ ID NO | Sequence function | Sequence |
|---|---|---|
| | | GGCGTGGAGGTGCATAATGCCAAGACAAAGCCGCGGGAG<br>GAGCAGTACAACAGCACGTACCGTGTGGTCAGCGTCCTCA<br>CCGTCCTGCACCAGGACTGGCTGAATGGCAAGGAGTACA<br>AGTGCAAGGTCTCCAACAAAGCCCTCCCAGCCCCCATCGA<br>GAAAACCATCTCCAAAGCCAAAGGGCAGCCCCGAGAACC<br>ACAGGTGTACACCCTGCCCCCATCCCGGGAGGAGATGAC<br>CAAGAACCAGGTCAGCCTGACCTGCCTGGTCAAAGGCTTC<br>TATCCCAGCGACATCGCCGTGGAGTGGGAGAGCAATGGG<br>CAGCCGGAGAACAACTACAAGACCACGCCTCCCGTGCTG<br>GACTCCGACGGCTCCTTCTTCCTCTACAGCAAGCTCACCG<br>TGGACAAGAGCAGGTGGCAGCAGGGGAACGTCTTCTCAT<br>GCTCCGTGATGCATGAGGCTCTGCACAACCACTACACGCA<br>GAAGAGCCTCTCCCTGTCTCCGGGTAAATGATTCTAGA |
| 32 | hMP08-R3-F08-VL nucleic acid | GCGGCCGCAAACTACAAGACAGACTTGCAAAAGAAGGCA<br>TGCACAGCTCAGCACTGCTCTGTTGCCTGGTCCTCCTGACT<br>GGGGTGAGGGCCCAGTCCGTGCTGACCCAGCCCGCCTCCG<br>TGTCCGGAAGCCCAGGACAGTCCATCACCATCTCCTGCGC<br>CGGCACCTCCTCCGACGTGGGAGGAAACAGCTACGTGTCC<br>TGGTATCAACAGCACCCCGGCAAAGCACCCAAACTGATG<br>ATCTACTCCGACAGTTCCCGCCCCTCCGGCGTGTCCAACA<br>GGTTCAGCGGCTCCAAGAGCGGCAACACCGCCTCCCTGAC<br>TATCTCCGGCCTGCAGGCTGAAGACGAAGCCGACTACTAC<br>TGCTCCTCCTACACCCAGTACTCCACCCGCGTGTTCGGCG<br>GCGGCACCAAACTGGCCGTGCTGGGTCAGCCCAAGGCCA<br>ACCCCACTGTCACTCTGTTCCCGCCCTCCTCTGAGGAGCTC<br>CAAGCCAACAAGGCCACACTAGTGTGTCTGATCAGTGACT<br>TCTACCCGGGAGCTGTGACAGTGGCCTGGAAGGCAGATG<br>GCAGCCCCGTCAAGGCGGGAGTGGAGACCACCAAACCCT<br>CCAAACAGAGCAACAACAAGTACGCGGCCAGCAGCTACC<br>TGAGCCTGACGCCCGAGCAGTGGAAGTCCCACAGAAGCT<br>ACAGCTGCCAGGTCACGCATGAAGGGAGCACCGTGGAGA<br>AGACAGTGGCCCCTACAGAATGTTCATGATTCTAGA |
| 33 | hMP08-R3-C11-VH nucleic acid | GCGGCCGCAAACTACAAGACAGACTTGCAAAAGAAGGCA<br>TGCACAGCTCAGCACTGCTCTGTTGCCTGGTCCTCCTGACT<br>GGGGTGAGGGCCGAGGTGCAGCTGGTGGAGAGCGGGGGC<br>AGCCTGGTGAAGCCAGGGGGAAGCCTGAGGCTGAGCTGT<br>GCCGCATCCGGGTTTACATTTTCCAACTACGACATGAACT<br>GGGTGAGGCAGGCCCCCGGCAAAGGACTGGAGTGGATTT<br>CAGACATCTCCGGCAGCAGTTCCTACATCGACTACGCTGA<br>TTTTGTGAAGGGCAGGTTCACAATCTCCCGGGACAACGCT<br>AAGAACTCCCTGTACCTGCAGATGAACAGTCTGAGGGCC<br>GAGGACACCGCTGTGTACTACTGCGTGAGGTCCTCCTACT<br>ATAGTGGCAGCGGCATGGACGTGTGGGGCCGGGGAACCC<br>TGGTGACCGTGTCCTCTGCTAGCACCAAGGGCCCATCGGT<br>CTTCCCCCTGGCACCCTCCTCCAAGAGCACCTCTGGGGGC<br>ACAGCGGCCCTGGGCTGCCTGGTCAAGGACTACTTCCCCG<br>AACCGGTGACGGTGTCGTGGAACTCAGGCGCCCTGACCA<br>GCGGCGTGCACACCTTCCCGGCTGTCCTACAGTCCTCAGG<br>ACTCTACTCCCTCAGCAGCGTGGTGACCGTGCCCTCCAGC<br>AGCTTGGGCACCCAGACCTACATCTGCAACGTGAATCACA<br>AGCCCAGCAACACCAAGGTGGACAAGAAAGTTGAGCCCA<br>AATCTTGTGACAAAACTCACACATGCCCACCGTGCCCAGC<br>ACCTGAACTCCTGGGGGGACCGTCAGTCTTCCTCTTCCCC<br>CCAAAACCCAAGGACACCCTCATGATCTCCCGGACCCCCG<br>AGGTCACATGCGTGGTGGTGGACGTGAGCCACGAAGACC<br>CTGAGGTCAAGTTCAACTGGTACGTGGACGGCGTGGAGG<br>TGCATAATGCCAAGACAAAGCCGCGGGAGGAGCAGTACA<br>ACAGCACGTACCGTGTGGTCAGCGTCCTCACCGTCCTGCA<br>CCAGGACTGGCTGAATGGCAAGGAGTACAAGTGCAAGGT<br>CTCCAACAAAGCCCTCCCAGCCCCCATCGAGAAAACCATC<br>TCCAAAGCCAAAGGGCAGCCCCGAGAACCACAGGTGTAC<br>ACCCTGCCCCCATCCCGGGAGGAGATGACCAAGAACCAG<br>GTCAGCCTGACCTGCCTGGTCAAAGGCTTCTATCCCAGCG<br>ACATCGCCGTGGAGTGGGAGAGCAATGGGCAGCCGGAGA<br>ACAACTACAAGACCACGCCTCCCGTGCTGGACTCCGACGG<br>CTCCTTCTTCCTCTACAGCAAGCTCACCGTGGACAAGAGC<br>AGGTGGCAGCAGGGGAACGTCTTCTCATGCTCCGTGATGC<br>ATGAGGCTCTGCACAACCACTACACGCAGAAGAGCCTCTC<br>CCTGTCTCCGGGTAAATGATTCTAGA |

-continued

TABLE OF SEQUENCES

| SEQ ID NO | Sequence function | Sequence |
|---|---|---|
| 34 | hMP08-R3-C11-VL nucleic acid | GCGGCCGCAAACTACAAGACAGACTTGCAAAAGAAGGCA TGCACAGCTCAGCACTGCTCTGTTGCCTGGTCCTCCTGACT GGGGTGAGGGCCCAGTCCGTGCTGACCCAGCCCGCCTCCG TGTCCGGAAGCCCAGGACAGTCCATCACCATCTCCTGCGC CGGCACCTCCTCCGACGTGGGAGGAGGAAGCTCCGTGAG CTGGTATCAACAGCACCCCGGCAAAGCACCCAAACTGAT GATCTACCAGGACAGCTACAGGCCCTCCGGCGTGTCCAAC AGGTTCAGCGGCTCCAAGAGCGGAAACACAGCCTCTCTG ACCATCTCCGGCCTGCAGGCTGAGGACGAAGCCGACTACT ACTGCTCATCCTACACTTACTATTCCACCAGGGTGTTCGG AGGCGGAACAAAACTGGCCGTGCTGGGTCAGCCCAAGGC CAACCCCACTGTCACTCTGTTCCCGCCCTCCTCTGAGGAG CTCCAAGCCAACAAGGCCACACTAGTGTGTCTGATCAGTG ACTTCTACCCGGGAGCTGTGACAGTGGCCTGGAAGGCAG ATGGCAGCCCCGTCAAGGCGGGAGTGGAGACCACCAAAC CCTCCAAACAGAGCAACAACAAGTACGCGGCCAGCAGCT ACCTGAGCCTGACGCCCGAGCAGTGGAAGTCCCACAGAA GCTACAGCTGCCAGGTCACGCATGAAGGGAGCACCGTGG AGAAGACAGTGGCCCCTACAGAATGTTCATGATTCTAGA |
| 35 | hMP09-R3-D03-VH nucleic acid | GCGGCCGCAAACTACAAGACAGACTTGCAAAAGAAGGCA TGCACAGCTCAGCACTGCTCTGTTGCCTGGTCCTCCTGACT GGGGTGAGGGCCGAGGTGCAGCTGGTGGAGAGCGGGGGC AGCCTGGTGAAGCCAGGGGGAAGCCTGAGGCTGAGCTGT GCCGCATCCGGGTTTACATTTTCCAACTACTATATGAACT GGGTGAGGCAGGCCCCTGGCAAGGGCCTGGAGTGGATTT CATCTATCTCCGGCAGTAGTCGATACATCTACTACGCTGA CTTTGTGAAGGGCCGGTTCACCATCTCCAGGGACAACGCT AAGAACTCCCTGTATCTGCAGATGAACTCCCTGCGCGCCG AGGACACCGCCGTGTACTACTGCGTGCGCTCCTCCGGCAG CTACTTCGGAAATGCTATGGATGTGTGGGGGAGGGGGAC CCTGGTGACCGTGTCCTCCGCTAGCACCAAGGGCCCATCG GTCTTCCCCCTGGCACCCTCCTCCAAGAGCACCTCTGGGG GCACAGCGGCCCTGGGCTGCCTGGTCAAGGACTACTTCCC CGAACCGGTGACGGTGTCGTGGAACTCAGGCGCCCTGAC CAGCGGCGTGCACACCTTCCCGGCTGTCCTACAGTCCTCA GGACTCTACTCCCTCAGCAGCGTGGTGACCGTGCCCTCCA GCAGCTTGGGCACCCAGACCTACATCTGCAACGTGAATCA CAAGCCCAGCAACACCAAGGTGGACAAGAAAGTTGAGCC CAAATCTTGTGACAAAACTCACACATGCCCACCGTGCCCA GCACCTGAACTCCTGGGGGGACCGTCAGTCTTCCTCTTCC CCCCAAAACCCAAGGACACCCTCATGATCTCCCGGACCCC CGAGGTCACATGCGTGGTGGTGGACGTGAGCCACGAAGA CCCTGAGGTCAAGTTCAACTGGTACGTGGACGGCGTGGA GGTGCATAATGCCAAGACAAAGCCGCGGGAGGAGCAGTA CAACAGCACGTACCGTGTGGTCAGCGTCCTCACCGTCCTG CACCAGGACTGGCTGAATGGCAAGGAGTACAAGTGCAAG GTCTCCAACAAAGCCCTCCCAGCCCCCATCGAGAAAACCA TCTCCAAAGCCAAAGGGCAGCCCCGAGAACCACAGGTGT ACACCCTGCCCCCATCCCGGGAGGAGATGACCAAGAACC AGGTCAGCCTGACCTGCCTGGTCAAAGGCTTCTATCCCAG CGACATCGCCGTGGAGTGGGAGAGCAATGGGCAGCCGGA GAACAACTACAAGACCACGCCTCCCGTGCTGGACTCCGAC GGCTCCTTCTTCCTCTACAGCAAGCTCACCGTGGACAAGA GCAGGTGGCAGCAGGGGAACGTCTTCTCATGCTCCGTGAT GCATGAGGCTCTGCACAACCACTACACGCAGAAGAGCCT CTCCCTGTCTCCGGGTAAATGATTCTAGA |
| 36 | hMP09-R3-D03-VL nucleic acid | GCGGCCGCAAACTACAAGACAGACTTGCAAAAGAAGGCA TGCACAGCTCAGCACTGCTCTGTTGCCTGGTCCTCCTGACT GGGGTGAGGGCCCAGTCCGTGCTGACCCAGCCCGCCTCCG TGTCCGGAAGCCCAGGACAGTCCATCACCATCTCCTGCGC CGGCACCTCCTCCGACGTGGGAGGATACTACTCCGTGAGC TGGTATCAACAGCACCCCGGCAAAGCCCCCAAACTGATG ATCTACTACGACAGCTCCCGGCCCTCCGGCGTGTCTAACA GGTTCTCCGGCTCCAAGAGCGGCAACACCGCCAGCCTGAC CATCTCCGGCCTGCAGGCAGAAGACGAGGCCGACTACTA CTGCTCCTCCGACACCTCCTACAGCACCAGGGTGTTCGGC GGTGGCACCAAGCTGGCCGTGCTGGGTCAGCCCAAGGCC AACCCCACTGTCACTCTGTTCCCGCCCTCCTCTGAGGAGC TCCAAGCCAACAAGGCCACACTAGTGTGTCTGATCAGTGA CTTCTACCCGGGAGCTGTGACAGTGGCCTGGAAGGCAGAT GGCAGCCCCGTCAAGGCGGGAGTGGAGACCACCAAACCC |

-continued

| TABLE OF SEQUENCES | | |
|---|---|---|
| SEQ ID NO | Sequence function | Sequence |
| | | TCCAAACAGAGCAACAACAAGTACGCGGCCAGCAGCTAC<br>CTGAGCCTGACGCCCGAGCAGTGGAAGTCCCACAGAAGC<br>TACAGCTGCCAGGTCACGCATGAAGGGAGCACCGTGGAG<br>AAGACAGTGGCCCCTACAGAATGTTCATGATTCTAGA |

EXAMPLES

The present invention is further illustrated by the following examples.

TABLE 1

Sequences of the antibodies of the examples.

| | MP08-R3-F08 | MP08-R3-C11 | MP09-R3-D03 |
|---|---|---|---|
| $V_H$-CDR1 | SEQ ID NO: 6 | SEQ ID NO: 12 | SEQ ID NO: 18 |
| $V_H$-CDR2 | SEQ ID NO: 7 | SEQ ID NO: 13 | SEQ ID NO: 19 |
| $V_H$-CDR3 | SEQ ID NO: 8 | SEQ ID NO: 14 | SEQ ID NO: 20 |
| $V_L$-CDR1 | SEQ ID NO: 9 | SEQ ID NO: 15 | SEQ ID NO: 21 |
| $V_L$-CDR2 | SEQ ID NO: 10 | SEQ ID NO: 16 | SEQ ID NO: 22 |
| $V_L$-CDR3 | SEQ ID NO: 11 | SEQ ID NO: 17 | SEQ ID NO: 23 |
| VH sequence | SEQ ID NO: 24 | SEQ ID NO: 26 | SEQ ID NO: 28 |
| VL sequence | SEQ ID NO: 25 | SEQ ID NO: 27 | SEQ ID NO: 29 |

Example 1: Antibody Production

Materials and Methods

Three antibody clones (i.e., MP08-R3-F08, MP08-R3-C11 and MP09-R3-D03) were produced in both human IgG1 lambda and rat IgG2b kappa formats and purified. For IgG expression, the VH and VL chain fragments were cloned into an IgG expression system encoding heavy and light chains on separate pcDNA3.4 plasmids. Constructs were sequenced to validate correct insertion of VH and VL sequences.

Plasmids were transiently transfected into ExpiCHO cells and IgG containing supernatants were filtered (0.22 μm) and purified on protein A columns. Antibodies that did not reach 98% purity went through a second purification step by preparative SEC (size exclusion chromatography). A limulus amebocyte lysate test was conducted to measure endotoxin levels in purified IgGs.

Results

The summary of the antibody production, purification and quality control is presented in Table 2.

All three antibody clones displayed high expression yields both in the human IgG1 format, with high amounts recovered after protein A purification (up to 400 mg/L culture). In the rat IgG2b format, while clone MP08-R3-F08 expressed to a similar high yield, clones MP08-R3-C11 and MP09-R3-D3 expressed to a moderate yield, with 6.3 and 7.5 mg of purified IgG recovered respectively from 100 mL cultures.

The six antibodies were analyzed by SDS-PAGE: 1.3 μg of each antibody clone were loaded per well in reducing and non-reducing conditions. All six antibodies showed a standard migration profile with one band at 50 kDa and another band at 25 kDa, corresponding to the heavy and light chains respectively (data not shown).

TABLE 2

Summary of production purification and quality control of the 3 antibody clones in both human IgG1 and rat IgG2b formats.

| | | | Purity | | | | | | | | |
|---|---|---|---|---|---|---|---|---|---|---|---|
| | | Yield (mg) | | Analytical SEC after protein A purification | | Analytical SEC after preparative SEC | | | Yield (mg) after | Delivered | Endotoxin |
| | Antibody name | after protein A purification | SDS-PAGE | SEC-214 nm | SEC-280 nm | SEC-214 nm | SEC-280 nm | Yield (mg) after SEC | endotoxin removal | quantity (mg) | level (EU/mg) |
| Human | MP08-R3-F08 | 34.7 | >95% | 73.7% | 74.7% | 100% | 100% | 16.8 | 11.06 | 11.1 | <1 |
| IgG1 | MP08-R3-C11 | 46.4 | >95% | 91.4% | 91.5% | 99.3% | 99.4% | 27.3 | 24.96 | 25 | <1 |
| lambda | MP09-R3-D03 | 22.4 | >95% | 98.6% | 98.7% | / | / | / | / | 22.4 | <1 |
| Rat | MP08-R3-F08 | 16.4 | >95% | 53.1% | 53.4% | 99.4% | 99% | 4.1 | / | 4.1 | <1 |
| IgG2b | MP08-R3-C11 | 6.3 | >95% | 77.3% | 77.6% | 99.4% | 99% | 0.5 | / | 0.5 | <1 |
| kappa | MP09-R3-D03 | 7.5 | >95% | 82.4% | 83% | 99.5% | 99.5% | 0.2 | / | 0.2 | >1, <5 |

Example 2: Antibody Binding to Recombinant CD8α Protein

Materials and Methods

Five μg/mL of streptavidin were coated on Nunc Maxisorp 96-well plates (ThermoFisher #442404) at 100 μL/well and incubated 1 hour at room temperature. Biotinylated human CD8α (Fisher Scientific #17196181) and mouse CD8α (Sino biological #50389-M08H-B) were added at 0.5 μg/mL in 100 μL/well and incubated overnight at 4° C.

Human CD4 (Sino biological #10400-H08H) was coated passively at 1 μg/mL in 100 μL/well and incubated overnight at 4° C. Plates were then blocked using 200 μL of PBS containing 4% skimmed milk for 1 hour at room temperature.

The three antibody clones (in both human IgG1 lambda and rat IgG2b kappa formats) were diluted in milk-PBS and tested at different concentrations (75, 25, 8.3, 2.8, 0.93, 0.31, 0.103, 0.034, 0.011, 0.0038, 0.0013 and 0.00042 μg/mL). 100 μL/well were incubated 1 hour at room temperature.

Human IgGs were detected using an anti-hFab-HRP (Sigma #A0293, 1:4000 dilution), while rat IgGs were detected using an anti-rat-HRP (Sigma #A9037, 1:10 000 dilution), at 100 μL/well and incubated 1 hour at room temperature.

TMB ((3,3',5,5' tetramethylbenzidine) Thermo Scientific #12617087) was added for a 3-minute incubation. Reaction was stopped with $H_2SO_4$ and absorbance at 450 nm was read on a microplate reader (Pherastar FS, BMG Labtech).

Results

Figure 1A:
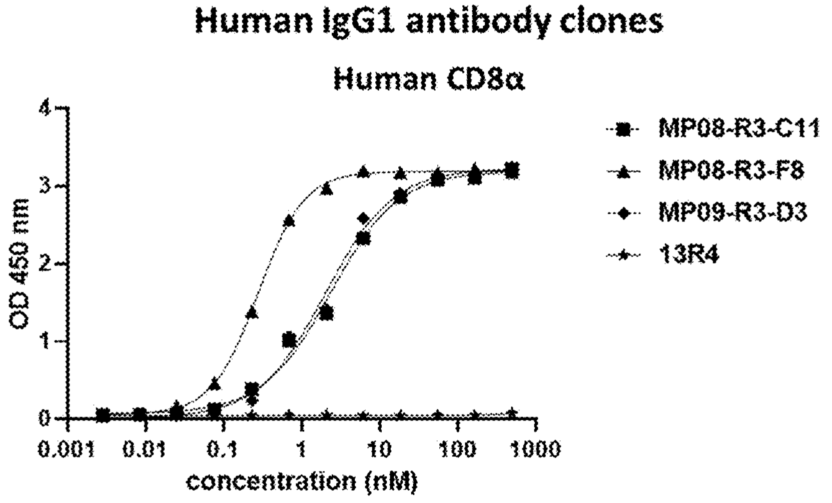
FIG. 1A-C is a combination of graphs showing the dose-response ELISA of the 3 antibody clones (i.e., MP08-R3-F08, MP08-R3-C11 and MP09-R3-D03) in the human IgG1 format on immobilized recombinant human CD8α, mouse CD8α and human CD4. 12 different concentrations were tested (75, 25, 8.3, 2.8, 0.93, 0.31, 0.103, 0.034, 0.011, 0.0038, 0.0013 and 0.00042 μg/mL). All antibodies had a mean molecular mass of about 150 kDa. An irrelevant human IgG1 antibody named 13R4 was included as negative control. 1A: human CD8α. 1B: mouse CD8α, 1C: human CD4.
Figure 1B:
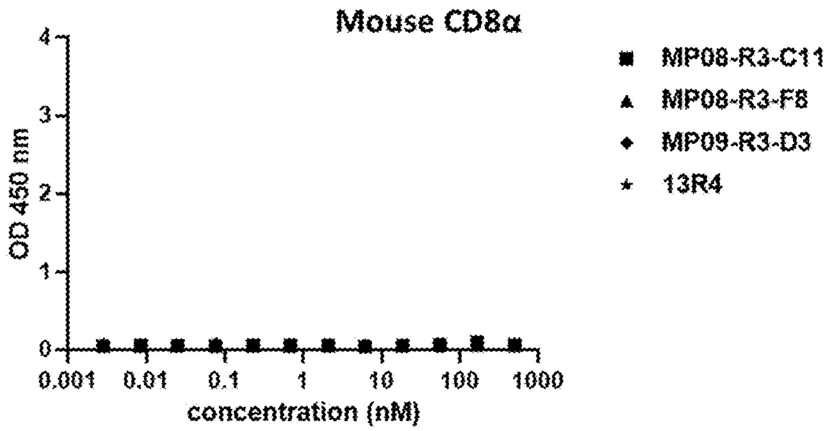
Figure 2A:
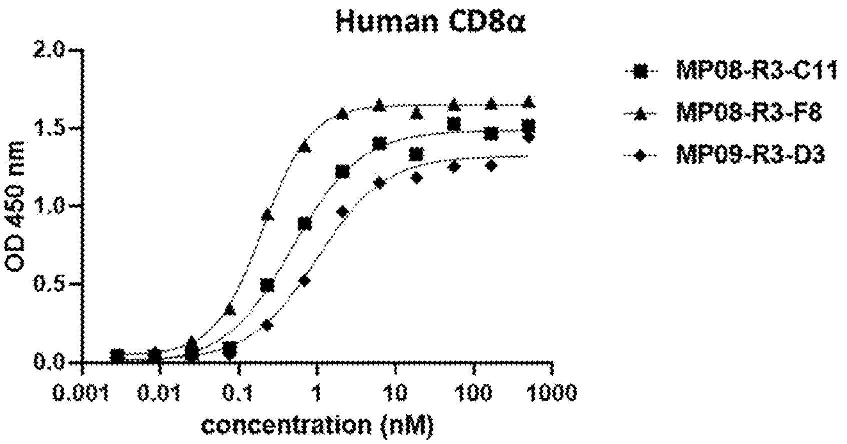
FIG. 2A-C is a combination of graphs showing the dose-response ELISA of the 3 antibody clones (i.e., MP08-R3-F08, MP08-R3-C11 and MP09-R3-D03) in the rat IgG2b format on immobilized recombinant human CD8α, mouse CD8α and human CD4. 12 different concentrations were tested (75, 25, 8.3, 2.8, 0.93, 0.31, 0.103, 0.034, 0.011, 0.0038, 0.0013 and 0.00042 μg/mL). All antibodies had a mean molecular mass of about 150 kDa. 2A: human CD8α. 2B: mouse CD8α, 2C: human CD4.
Figure 2B:
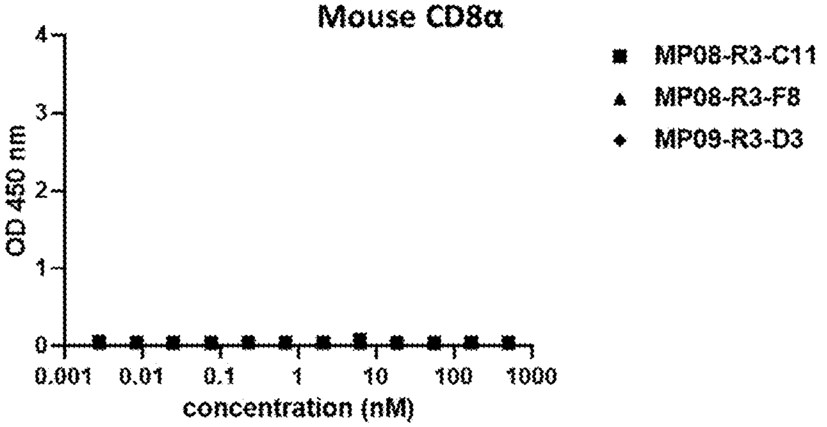

All three tested antibody clones were capable of binding to human CD8α, with EC50 ranging from 0.28 to 2.0 nM for clones in the human IgG1 format (FIG. 1A and Table 3) and ranging from 0.20 to 0.99 nM for clones in the rat IgG2b format (FIG. 2A and Table 3). No cross-reactivity was observed on mouse CD8α (FIG. 1B for human IgG1 clones and FIG. 2B for rat IgG2b clones).

Figure 1C:
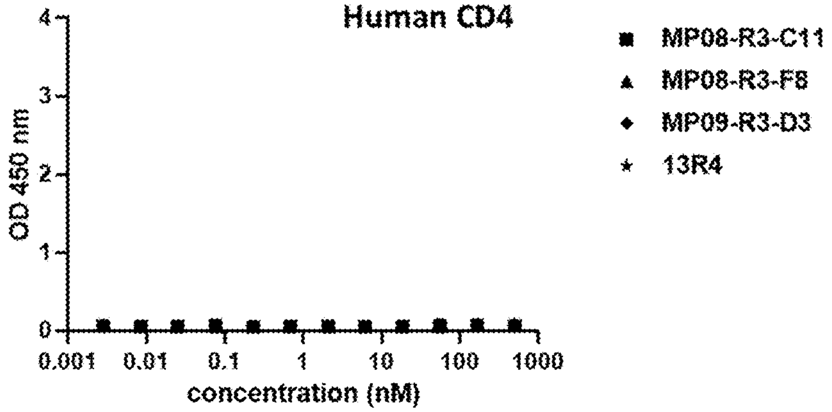
Figure 2C:
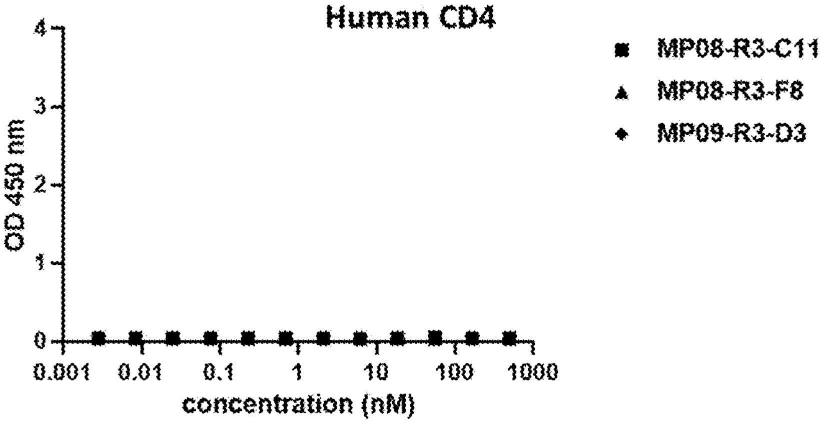

Binding specificity tested on human CD4 showed that none of the three antibody clones bound to this protein, neither in human IgG1 nor in rat IgG2b format (FIG. 1C for human IgG1 clones and FIG. 2C for rat IgG2b clones).

These results demonstrate that the three antibody clones (i.e., MP08-R3-F08, MP08-R3-C11 and MP09-R3-D03) possess strong binding towards human CD8α, as well as a good specificity towards human CD8α. Additionally, none of the three antibody clones exhibit binding towards human CD4 or cross-reactivity towards mouse CD8α.

TABLE 3

Summary of the EC50, CI 95% and Rsquared of the three antibody clones in the human IgG1 and rat IgG2b formats.

| | | MP08-R3-F08 | MP08-R3-C11 | MP09-R3-D03 |
|---|---|---|---|---|
| Human | EC50 (nM) | 0.28 | 2.4 | 2.0 |
| IgG1 | CI 95% (nM) | 0.26 to 0.30 | 1.8 to 3.1 | 1.5 to 2.8 |
| | Rsquared | 0.28 | 2.4 | 2.0 |
| Rat | EC50 (nM) | 0.20 | 0.48 | 0.99 |
| IgG2 | CI 95% (nM) | 0.18 to 0.22 | 0.36 to 0.66 | 0.69 to 1.4 |
| | Rsquared | 0.999 | 0.993 | 0.990 |

Example 3: Antibody Binding to CD8+ and Non-Binding to CD8− Cells

Materials and Methods 200,000 HPB-ALL cells (expressing CD8α and referred to as CD8+) or 1299 cells (not expressing CD8α and referred to as CD8−) were incubated with primary antibodies: mouse anti-CD8α (Sino biological #10980-MM28, 1:50 dilution), or with one of the three antibody clones (i.e., MP08-R3-F08, MP08-R3-C11, and MP09-R3-D03) in the human IgG1 or rat IgG2b format, at a concentration of 10, 3.3, 1.1 or 0.37 μg/mL. HPB-ALL is a cell line of human lymphocytes derived from T cell leukemia. 1299 (or H1299) is a cell line of human epithelial-like cells derived from non-small cell lung carcinoma.

Human antibodies were detected using an anti-human F(ab')2-AF647 antibody (Jackson #109-605-006, 1:100 dilution), rat antibodies with an anti-rat-FITC antibody (Sigma #F1763, 1:320 dilution) and the anti-human CD8α mouse antibody with an anti-mouse-FTTC antibody (Sigma #12-506, 1:100 dilution). Results were acquired on a CytoFLEX cytometer (Beckman Coulter) and analysed using FlowJo.

Results

Cells were validated by flow cytometry using control experiments (data not shown). Background signal from secondary antibodies was determined on both cell lines (data not shown). An irrelevant human IgG1 termed "13R4" showed no binding on either of the cell lines (FIG. 3D for HPB-ALL cells and FIG. 4D for H1299 cells). CD8α expression was also assessed using a commercial anti-CD8α antibody, showing a strong signal on HPB-ALL cells (CD8+ cells) and no signal on H1299 cells (CD8− cells), as expected (FIG. 3E for HPB-ALL cells and FIG. 4E for H1299 cells).

Figure 3A:
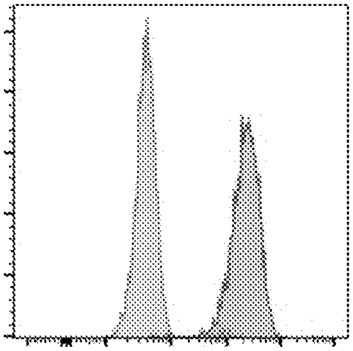
FIG. 3A-E is a combination of flow cytometry plots showing the binding of the 3 antibody clones (i.e., MP08-R3-F08, MP08-R3-C11 and MP09-R3-D03) in the human IgG1 format onto CD8+ cells (HPB-ALL cells). Irrelevant human IgG1 13R4 antibody was used as a negative control and a commercial mouse anti-human CD8α antibody was used as a positive control. Antibodies were used at a concentration of 3.3 μg/mL. Light grey represents cells alone (back ground signal), darker grey represents cells with one of the antibodies as indicated (binding signal).
Figure 3B:
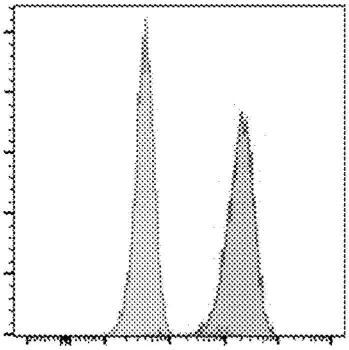
Figure 3C:
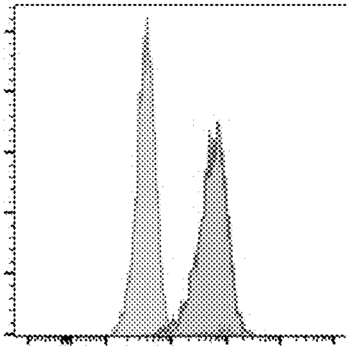
Figure 3D:
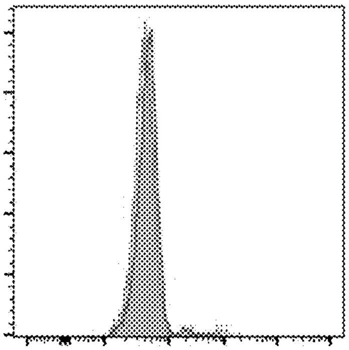
Figure 3E:
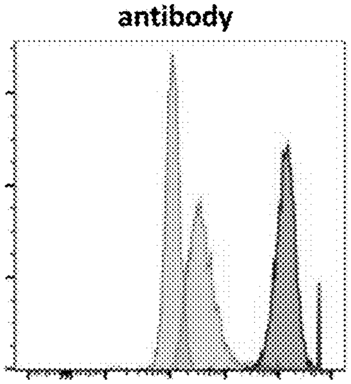
Figure 4A:
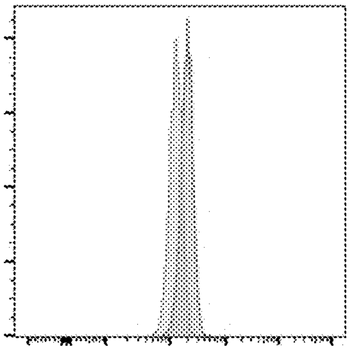
Figure 4B:
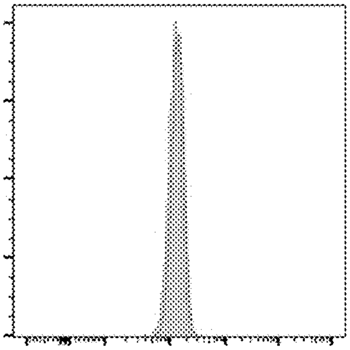
Figure 4C:
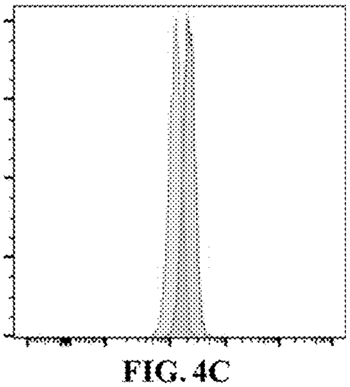
Figure 4D:
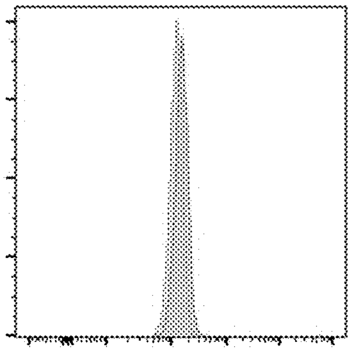
Figure 4E:
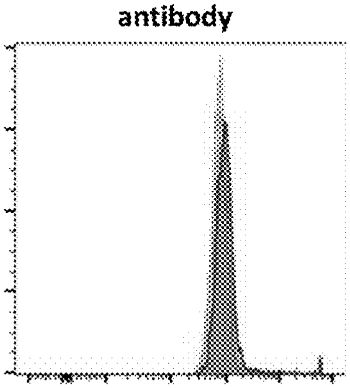

Antibody binding to both cell lines was assessed by flow cytometry. All three antibody clones in the human IgG1 format bound to HPB-ALL CD8+ cells (FIGS. 3A-C showing the 3.3 μg/mL concentration), while no binding was observed on H1299 CD8− cells (FIGS. 4A-C showing the 3.3 μg/mL concentration).

At the lowest concentration (0.37 μg/mL), clones MP08-R3-C11 and MP08-R3-F08 showed the strongest signals (data not shown), suggesting higher affinities.

Similar results were obtained with the rat IgG2b format, with clones MP08-R3-C11 and MP08-R3-F08 giving the strongest signals at 0.37 μg/mL (data not shown).

These results confirm the results obtained on recombinant human CD8α protein and demonstrate that the three antibody clones (i.e., MP08-R3-F08, MP08-R3-C11 and MP09-R3-D03) possess a strong binding and good specificity towards human CD8α.

Example 4: Antibody Binding to Primary CD8+ T Cells

Materials and Methods

Human PBMCs (peripheral blood mononuclear cells) were prepared from a buffy coat using density gradient. Buffy coat was diluted ½ in PBS-SVF 2% and 30 mL were loaded onto 15 mL of Lymphoprep (Fisher Scientific #17171036). Tubes were centrifuged 20 min at 2000 rpm with no brake. PBMC were taken at the lymphoprep/plasma interface, washed with PBS-SVF and centrifuged 5 min at 1200 rpm. CD8+ T cells isolation was performed using CD8α+ T Cell Isolation Kit (Miltenyi Biotec #130-104-075) according to manufacturer's instructions.

Cells were incubated with primary antibodies: mouse anti-CD8α (Sino biological #10980-MM28, 1:50 dilution), or with one of the three antibody clones (i.e., MP08-R3-F08, MP08-R3-C11, and MP09-R3-D03) in the human IgG1 or rat IgG2b format, at a concentration of 10, 3.3, 1.1 or 0.37 μg/mL. Human antibodies were detected using an anti-human F(ab')2-AF647 antibody (Jackson #109-605-006, 1:100 dilution), rat antibodies with anti-rat-FITC antibody (Sigma #F1763, 1:320 dilution) and the anti-human CD8α mouse antibody with an anti-mouse-FITC antibody (Sigma #12-506, 1:100 dilution). Results were acquired on a CytoFLEX cytometer (Beckman Coulter) and analyzed using FlowJo.

Results

Cells were validated by flow cytometry using control experiments (data not shown). Background signal from secondary antibodies was determined (data not shown). An irrelevant human IgG1 termed "13R4" showed no binding to fresh CD8+ T cells (FIG. 5D). CD8α expression was also assessed using a commercial anti-CD8α antibody, showing a strong signal on purified primary CD8+ T cells (FIG. 5E).

Figure 5A:
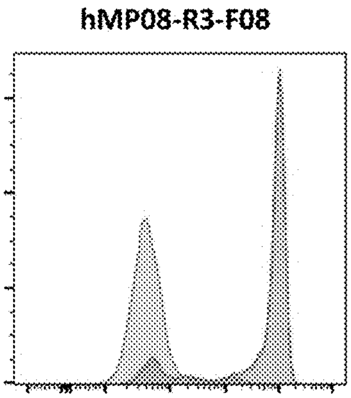
Figure 5B:
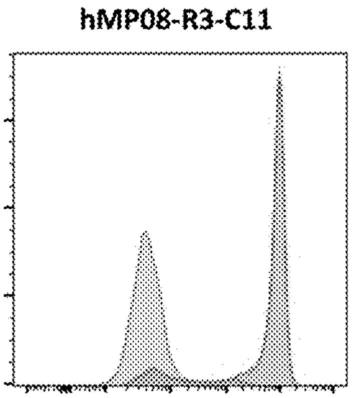
Figure 5C:
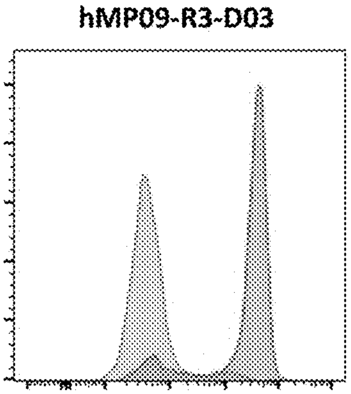
Figure 5D:
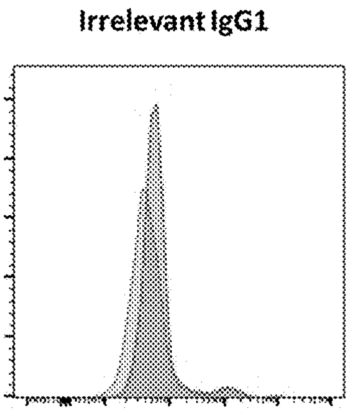
Figure 5E:
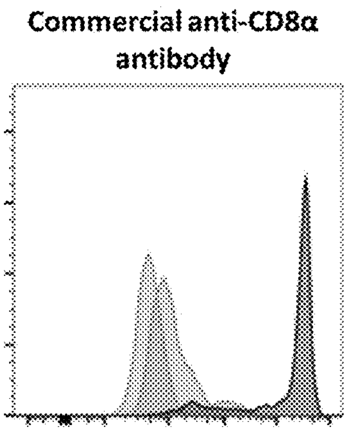

Antibody binding to fresh primary CD8+ T cells was assessed by flow cytometry, showing binding of all three antibody clones in the human IgG1 format (FIGS. 5A-C).

As with the HPB-ALL CD8+ cell line, at the lowest concentration (0.37 μg/mL), clones MP08-R3-C11 and MP08-R3-F08 showed again the strongest signals (data not shown), suggesting a higher affinity for these two clones.

Similar results were obtained in rat IgG2b format with clones MP08-R3-C11 and MP08-R3-F08 giving the strongest signals at 0.37 μg/mL (data not shown).

These results confirm the results obtained on recombinant human CD8α protein and on CD8+/CD8− cell lines and demonstrate that the three antibody clones (i.e., MP08-R3-F08, MP08-R3-C11 and MPO9-R3-D03) exhibits good binding for human CD8α.

Example 5: Human CD8 Depletion In Vivo

Materials and Methods

Mice

B6; SJL-Tg(CD8aCD8b)57Scr/J mice were used (Jackson Laboratory strain #003202, LaFace et al. Human CD8 transgene regulation of HLA recognition by murine T cells. J Exp Med. 1995 Nov. 1; 182(5):1315-25); and later designed as hCD8 mice. These hCD8 mice express a transgene containing the human CD8 (hCD8) alpha and beta chains expressed under the control of the murine $p56^{lck}$ proximal promoter.

Preliminary experiments confirmed the absence of expression of human CD8α (i.e., hCD8α) in control C57B16 mice (named control WT mice, FIG. 6A) and strong human CD8α expression in transgenic mice expressing hCD8α transgene (FIG. 6B). However, this hCD8α expression is not restricted to CD8 T cells.

Mice were maintained under identical standard conditions including housing, regular care, and normal chow diet in the same animal facility throughout the duration of the experiments (12 hours light/dark cycle with ad libitum access to food and water). Mice were aged 9 to 12 weeks at the beginning of experiments. Only males were used except for the hCD8 100 μg depletion group where half were females because of mice availability.

Antibody Injection

Upon isoflurane anesthesia, antibodies in the human IgG1 format (i.e., MP08-R3-F08, MP08-R3-C11 and MP09-R3-D03) were injected intravenously through the retro-orbital sinus with a 30-gauge insulin syringe. Mice were returned to their home cage after complete recovery from anesthesia.

Blood Sampling

At the required timepoints, blood was sampled from the submandibular vein. Upon isoflurane anesthesia, the left submandibular vein was punctured using a 25-gauge needle. A few drops of blood corresponding approximatively to 100 μL were collected in a collection tube containing 5 μL of heparin. After sample collection, bleeding was stopped by application of a sterile gauge. After complete recovery from the anesthesia, mice were returned to their home cage.

Flow Cytometry

For each sample, 50 μL of blood were incubated with 10 μL of FACS antibody solution for 30 minutes at room temperature.

In blood samples, erythrocytes were lysed using BD FACS lysis solution (BD Biosciences) after staining. Acquisition was performed on a LSR Fortessa cytometer, and further analysis performed using FlowJO v10.8. Forward scatter (FSC) and side scatter (SSC) parameters were used to gate live cells excluding red blood cells, debris, and cell aggregates. Cells were later selected based upon CD45 expression. For hCD8 transgenic mice, the expression level of hCD8α was assessed in total CD45+ cells; with control mice experiments, the expression of mCD8α was assessed from the CD45+CD11b-CD3+ cells.

Data Representation and Normalization

The number of $hCD8\alpha^{+}$ cells was evaluated within the total CD45+ cell population and then normalized to the average ratio of hCD8α+ in control non-depleted mice in order to assess the repopulation of the $hCD8\alpha^{+}$ cells.

Results

In order to evaluate the efficiency and duration of depletion of the hCD8α-expressing cells (hCD8+ cells), the 3 antibody clones (i.e., MP08-R3-F08, MP08-R3-C11 and MP09-R3-D03) were injected into mice at 3 different doses (50, 100 and 200 μg), with 3 mice per group. Immediate confirmation of depletion was performed by flow cytometry analysis 1 hour after antibody injection. Follow-up of hCD8α cell repopulation was done weekly for the 2 low doses; and at day 7, 14 and 42 for the high dose. In mice from the MP08-R3-C11 50 μg group one animal was excluded because of incorrect antibody injection.

Depletion of hCD8α-expressing cells was complete 1 hour after injection for all clones at 200 μg, while it was almost complete for the 50 μg and 100 μg doses (FIGS. 7A-C and 8A-C). At day 7 after injection, hCD8α depletion was total for all clones and doses (FIGS. 7A-C and 8A-C).

Later timepoints showed progressive hCD8α+ repopulation starting with the 50 μg dose, with the threshold of 50% repopulation attained by all clones at 50 μg by day 28 with very similar evolution (FIG. 8C). For higher dose, only clones MP08-R3-C11 (FIG. 7B) and MP09-R3-D03 (FIG. 7C) reached 50% repopulation at 100 μg and only MP09-R3-D03 reached 50% repopulation at 200 μg by day 42. The repopulation within 100 μg and 200 μg groups follow very similar trends for clones MP08-R3-F08 (FIG. 7A) and MP09-R3-D03 (FIG. 7C).

In order to investigate the cross-reactivity of the three human CD8α antibody clones with mouse CD8α, each of the three antibody clones were injected in control C57B16 mice and the evolution of the blood CD8 T cell population was evaluated.

As shown on the flow cytometry plots (FIG. 9A-D) and on the quantification (FIG. 9E), none of the three anti-human CD8α antibody clone was able to deplete mouse CD8 T cells in control mice, neither 1 hour after injection nor 7 days after. These results demonstrate that all three antibody clones do not cross-react with mouse CD8α.

Conclusion

These results show that all three antibody clones (i.e., MP08-R3-F08, MP08-R3-C11 and MP09-R3-D03) are capable of strongly binding to human CD8α recombinant protein, but also human CD8α expressed at the surface of CD8α-expressing cell lines and at the surface of primary CD8+ T cells. Additionally, all three antibody clones possess good specificity for human CD8α, with no binding to human CD4 and no cross-reactivity for mouse CD8α.

Furthermore, all three antibody clones are capable of depleting CD8α-expressing cells in vivo. Also, all three clones possess good specificity for human CD8α, with no cross-reactivity for mouse CD8α in vivo.

All clones induce a complete or almost complete depletion of CD8α-expressing cells within 1 hour after injection in human CD8α-expressing mice, depending on the dose. In addition, depletion is complete for all clones and doses for at least 7 days. After day 7 post-depletion, repopulation of hCD8α-expressing cells begins progressively. At the 50 μg dose, repopulation reaches 50% by day 28 with all clones, while the 50% repopulation is reached only by day 42 with clones MP08-R3-C11 and MP09-R3-D03 at dose 100 μg, and only with clone MP09-R3-D03 at dose 200 μg.

Thus, depletion of CD8α-expressing cells by the anti-CD8α antibodies of the invention is fast, almost complete if not complete, and transient. Indeed, CD8α-expressing cell repopulation after depletion is controlled and depends upon the dose of antibody used.

Taken together, these results indicate that the anti-CD8α antibodies as described herein could be valuable therapeutic tools for transiently depleting CD8α-expressing cells in a controlled manner.

Example 6: Antibody Specificity

Materials and Methods

The Retrogenix Cell Microarray Technology platform was used to screen for specific off-target binding interactions of the anti-CD8α antibody clone MP08-R3-F08.

Pre-Screen

The level of background binding of the anti-CD8α antibody clone MP08-R3-F08 to fixed untransfected HEK293 cells, and to cells overexpressing CD8α (isoform 1, isoform 2 secreted or tethered secreted) was evaluated. Binding to untransfected cells and target-expressing cells was assessed using an AlexaFluor 647 labelled anti-human IgG Fc detection antibody, followed by fluorescence imaging.

Library Screen

The level of binding of the anti-CD8α antibody clone MP08-R3-F08 was screened using fixed human HEK293 cells, individually over-expressing 6105 full-length human plasma membrane proteins, human secreted proteins, and cell surface-tethered human secreted proteins, as well as additional 400 human heterodimers.

Binding detection was performed using the same AlexaFluor 647 labelled anti-human IgG Fc detection antibody as above, followed by fluorescence imaging. The anti-CD8α antibody clone MP08-R3-F08 was tested against 2 replicates. Fluorescent images were analyzed and quantitated using Image Quant software.

A protein interaction was defined as a duplicate spot showing a raised signal compared to background levels. Interactions were classified as strong, medium, weak or very weak depending on the intensity of the duplicate spots.

Confirmation Screen

All proteins identified as interacting with the anti-CD8α antibody clone MP08-R3-F08 at the Library screen step were re-expressed in HEK293 cells. The level of binding of the anti-CD8α antibody clone MP08-R3-F08 was assessed on both fixed and non-fixed cells in the same manner than for the library screen using fluorescence imagining, and compared to Rituximab (anti-CD20 antibody) used as control antibody. The goal was to determine which interactions were repeatable and specific to the anti-CD8α antibody clone MP08-R3-F08.

Results

Pre-Screen

The anti-CD8α antibody clone MP08-R3-F08 showed low levels of background binding to fixed untransfected HEK293 cells at all three tested concentrations (i.e., 2, 5 and 20 μg/mL). The anti-CD8α antibody clone MP08-R3-F08 exhibited binding towards over-expressed CD8α (isoform 2 both secreted or tethered secreted) at all 3 concentrations, while binding towards over-expressed CD8α (isoform 1) was observed only at 5 and 20 μg/mL. Based on these results, further screenings were performed at 20 μg/mL on fixed cells.

Library Screen

After screening 6105 full-length human plasma membrane proteins, human secreted proteins, and cell surface-tethered human secreted proteins, as well as additional 400 human heterodimers over-expressed in HEK293 cells using 20 μg/mL anti-CD8α antibody clone MP08-R3-F08, 23 interactions were identified and further analyzed.

Confirmation Screen

For confirmation screen, the 23 proteins identified as interacting with anti-CD8α antibody clone MP08-R3-F08 at the step of library screen, as well as CD8α (isoform 1) and two control receptors (CD20 and EGFR) were over-expressed in HEK293 cells. Cells were used fixed or non-fixed and interaction with the anti-CD8α antibody clone MP08-R3-F08 was evaluated and compared with the control antibody (i.e., Rituximab).

On fixed cells microarrays, 22 out of the 23 proteins identified as interacting with the anti-CD8α antibody clone MP08-R3-F08 were reproducibly observed as interacting with anti-CD8α antibody clone MP08-R3-F08 (FIG. 10A).

The exception was FCGR3B, which showed a very weak intensity in the library screen, and lack of reproducibility into the confirmation screen indicates that the interaction was not real. Seventeen out of the 23 identified proteins were bound by both the anti-CD8α antibody clone MP08-R3-F08 and control antibody, and were therefore classified as non-specific interactions (FIGS. 10A-B). Those included Fc gamma receptors, which were presumably Fc-domain mediated, and IGHG3, which is bound directly by the detection antibody.

Additional three out of the 23 proteins, as well as CD8α (isoform 1) appeared to be specific to the anti-CD8α antibody clone MP08-R3-F08. However, signal intensities were so weak and close to background levels that they were categorized as non-significant.

After excluding the non-reproducible, non-specific, and non-significant interactions, only two remained that were significant and specific to the anti-CD8α antibody clone MP08-R3-F08: CD8α isoform 2 both secreted or tethered secreted forms. On non-fixed cells, the interactions with CD8α isoform 2 both secreted or tethered secreted forms of the anti-CD8α antibody clone MP08-R3-F08 was confirmed (FIG. 10C).

As a conclusion, anti-CD8α antibody clone MP08-R3-F08 showed a significant specific interaction with CD8α (isoform 2 both secreted or tethered secreted) on both fixed and live cell microarrays. No other specific interactions were identified, indicating high specificity of the anti-CD8α antibody clone MP08-R3-F08 for its target CD8α isoform 2.

Example 7: CD8 Depletion in Non-Human Primates

Materials and Methods

Animals

Four naïve healthy male Cynomolgus Monkeys aged 2 to 4 years old were used for this study. Animals were housed in stainless steel cages, one monkey per cage. The room temperature was maintained between 2° and 29° C. with a relative humidity of 40-70%. Fluorescent illumination was on 12-hour light (08:00-20:00) and 12-hour dark cycle. Monkeys had illimited access to water and food.

Antibody Injection

Each monkey was intravenously infused through the saphenous vein with either (1) 20 mg/kg bodyweight of anti-CD8α antibody clone MP08-R3-F08, (2) 20 mg/kg bodyweight of anti-CD8α antibody clone MP08-R3-C11, (3) 20 mg/kg bodyweight of anti-CD8α antibody clone MP09-R3-D3, or (4) 7.5 mg/kg bodyweight of anti-CD8α antibody clone MP08-R3-F08. Antibody infusion was completed within 30 minutes.

Sample Collection

Whole blood was collected into potassium (K2) EDTA tubes from each animal at day −1, day 0 (1 h), day 0 (6 h), day 0 (24 h), day 5, day 10, day 15 and day 22 post-injection for the three monkeys which received the 20 mg/kg dose of antibody and at day −1, day 0 (3 h), day 0 (6 h), day 0 (24 h), day 7, day 14, day 28, day 48 and day 62 post-injection for the monkey which received the 7.5 mg/kg dose of antibody.

Flow Cytometry

From whole blood samples, erythrocytes were lysed using BD FACS lysis solution (BD Biosciences cat #555898). After lysis, pelleted cells were washed twice with PBS 1% FBS. Cells were resuspended in PBS 1% FBS and incubated with FcR blocking buffer for 10 minutes, before staining for 1 h at 4° C. with antibodies as detailed in Table 4 below. After staining, cells were washed twice with PBS 1% FBS, fixed with fixation buffer for 10 minutes, washed again and resuspended in PBS before acquisition on a flow cytometer. Forward scatter (FSC) and side scatter (SSC) parameters were used to gate live cells excluding red blood cells, debris, and cell aggregates. Cells were later selected based upon CD45 expression. CD8+ cells were identified as CD45+ CD11b-CD3+CD4-CD8+ cells.

TABLE 4

Antibodies used for flow cytometry in non-human primate experiments.

| Antibody/Dye | Cat. # | Vendor |
|---|---|---|
| CD45-BV510 | 563530 | BD |
| CD11b-APC | 17-0118-42 | ebioscience |
| CD20-FITC | 555622 | BD |
| CD3-BV605 | 562994 | BD |
| CD4-BB700 | 566479 | BD |
| CD8- BV786 | 563823 | BD |
| CD16-R718 | 566969 | BD |
| CD14-BV650 | 563419 | BD |
| CD56-PE | 556647 | BD |
| CD66b-BV421 | 562940 | BD |
| Live/Dead- APC-CY7 | 565388 | BD |

Data Representation

The number of CD8α$^+$ cells was evaluated within the total CD45+ cell population and represented as a percentage of the CD45+ cells.

Results

In order to evaluate the efficiency of depletion of the CD8α-expressing cells, the 3 antibody clones (i.e., MP08-R3-F08, MP08-R3-C11 and MP09-R3-D03) were injected into monkeys at a dose of 20 mg/kg bodyweight, with one monkey per group. Immediate confirmation of depletion was performed by flow cytometry analysis 1 hour and 6 hours after antibody injection. Follow-up of CD8α-expressing cell depletion was done at 24 hours, day 5, day 10, day 15 and day 22 after antibody injection.

Depletion of CD8α-expressing cells was complete 1 hour after injection for clone MP08-R3-F08, and the percentage of CD8+ cells remained at 0% until day 22 (FIG. 10A). Antibody clones MP08-R3-C11 and MP09-R3-D03 induced an important decrease of CD8α-expressing cells, which lasted until day 22 (FIG. 10A). However, the depletion of CD8α-expressing cells induced by antibody clones MP08-R3-C11 and MP09-R3-D03 was not total.

Since antibody clone MP08-R3-F08 induced the most efficient depletion of the CD8α-expressing cells, another dose was tested. In order to evaluate the efficiency of depletion of the CD8α-expressing cells, antibody clone MP08-R3-F08 was injected into one additional monkey at a dose of 7.5 mg/kg bodyweight. Immediate confirmation of depletion was performed by flow cytometry analysis 1 hour and 6 hours after antibody injection. Follow-up of CD8α-expressing cell depletion was done at 24 hours, day 7, day 14, day 28, day 48 and day 62 after antibody injection.

Even at the lower dose of 7.5 mg/kg bodyweight, antibody clone MP08-R3-F08 induced a complete depletion of CD8α-expressing cells within 1 hour after injection. Additionally, the percentage of CD8+ cells remained at 0% until day 14 post injection. From day 14, CD8α-expressing cells started re-increasing very progressively and reached 2.5% by day 62 (FIG. 10B).

Example 8: Effect of the Anti-CD8α Antibody in a Mouse Model of Myocardial Infarction

Materials and Methods

Mice

B6; SJL-Tg(CD8aCD8b)57Scr/J were used (Jackson Laboratory strain #003202); and later designed as hCD8 mice, as described in Example 5 above.

Mice were maintained under identical standard conditions including housing, regular care, and normal chow diet in the same animal facility throughout the duration of the experiments (12 h light/dark cycle with ad libitum access to food and water). Mice were aged 9 to 15 weeks at the beginning of experiments. Both males and females were used.

Myocardial Infarction

Myocardial infarction (MI) was induced by permanent ligation of the left anterior descending artery in its proximal third, as previously described (Zouggari et al., Nature medicine, 2013). Mice were anesthetized by peritoneal injection of ketamine (100 mg per kg body weight; Ketamine 1000, Vibrac) and Xylazine (10 mg per kg body weight; Xylazine 2%, Bayer), intubated and ventilated with air using a small animal respirator (SAR 830/AP Ventilator, CWE Incorporated, Ardmore, USA). Body temperature was maintained to 37° C. using a homeothermic blanket system (Harvard Apparatus). The chest wall was shaved and a thoracotomy was performed in the fourth left intercostal space. The left ventricle was localized and the pericardial sac was opened. The left anterior descending artery was permanently ligated using a 7/0 PVDF monofilament suture (Peters surgical, France) 5 mm below the site of its emergence from the left atrium. Permanent whitening of the myocardium below the ligation was considered indicative of a successful coronary occlusion. The thorax and the skin were closed with 6/0 PVDF monofilament sutures (Peters surgical, France), with local application of lidocaine (Lidocaine 20 mg/mL, Aguettant). The endotracheal tube was removed once spontaneous respiration resumed, and mice were placed in a cage on a warm pad maintained at 37° C. until completely vigil. To reduce pain, buprenorphine (0.1 mg/kg) was injected before, 6 hours after the onset of surgery and twice a day for 48 to 72 hours.

Antibody Injection

One hour after the end of surgery, mice were injected intravenously with anti-CD8α antibody clone MP08-R3-F08 or sterile saline solution. Using a 29 Gauge insulin syringe, 100 μL of a solution containing either 100 μg of anti-CD8α antibody clone MP08-R3-F08 or saline solution was slowly injected in the retro-orbital sinus over 10 seconds. Mice were then placed in a cage on a warm pad maintained at 37° C. and returned to their home cage after complete recovery from anesthesia.

Organ Harvesting

Mice were euthanized using 150 mg/kg Euthasol in 250 μL of saline solution injected intraperitoneally upon isoflurane sedation. Blood from the vena cava was collected using a 27-gauge needle. Spleen and heart are weighed and rinsed in PBS for further analysis.

Cell Suspension Preparation and Flow Cytometry

Mice were sacrificed at day 3 or 21 post-MI. Peripheral blood was drawn via inferior vena using a syringe with a 27 Gauge needle primed with heparin solution. For blood staining, erythrocytes were lysed using BD FACS lysis solution (BD Biosciences). Spleens were surgically removed and dissociated, obtaining a single cell suspension that was filtered through 40 m nylon mesh (BD Biosciences). Cell suspensions were centrifuged at 400 g for 15 min at 4° C. Red blood cells were removed using a red blood lysis buffer (Sigma-Aldrich) and cells were washed with PBS and resuspended in 5 mL PBS supplemented with 3% FBS.

General characteristics of antibodies are summarized in Table 5 below. Surface marker staining was performed by incubating the cell suspension (50 μL blood or 50 μL of splenocytes suspension) with 10 μL of the antibody cocktail for 30 minutes at 4° C. before washing with PBS. Forward scatter (FSC) and side scatter (SSC) parameters were used to gate live cells excluding red blood cells, debris, and cell aggregates. Cells were analyzed using a BD LSR Fortessa flow cytometer (BD Biosciences) and data were analyzed using FlowJo v10.9 software (BD Biosciences).

The expression level of hCD8α was assessed in total CD45+ cells.

TABLE 5

Antibodies used for flow cytometry in mouse model of MI experiments

| Marker | Dye | Manufacturer | Clone | Reference | Dilution |
|---|---|---|---|---|---|
| CD45 | PerCP | BD Bioscience | 30-F11 | 557235 | 1:100 |
| CD11b | BV605 | BD Bioscience | M1/70 | 563015 | 1:100 |
| CD3 | PerCP-Cy5,5 | eBioscience | 145-2C11 | 45-0031-82 | 1:100 |
| B220 | V500 | BD Bioscience | RA3-6B2 | 561226 | 1:100 |
| CD4 | Efluor450 | eBioscience | RM4-5 | 48-0042-82 | 1:100 |
| mCD8a | AF700 | BD Bioscience | 53-6.7 | 557959 | 1:100 |
| hCD8a | FITC | eBioscience | HIT8a | 11-0089-42 | 1:100 |
| NK1.1 | APC | eBioscience | PK136 | 25-5941-82 | 1:100 |
| Ly6C | APC-Cy7 | BD Bioscience | AL-21 | 560596 | 1:100 |
| Ly6G | PE | BD Bioscience | 1A8 | 551461 | 1:100 |

Infarct Size Evaluation at Day 3 by TTC Staining

To evaluate infarct size at an early time point (3 days after MI), 2,3,5-triphenyltetrazolium chloride (TTC, Sigma Aldrich) was used. Hearts were harvested and sectioned into four 1.5-2 mm thick slices from the apex, in a semi-frozen state. The slices were then incubated for 40 min in PBS-1% TTC solution at 37° C. Sections were then rinsed twice 5 min with PBS at room temperature. Slices were photographed and infarct size was calculated using ImageJ blindly by measuring the total tissue area and the infarcted tissue area on each tissue slice.

Echocardiography

Cardiac function was assessed 21 days after MI. Chest wall was shaved using depilatory cream. Upon isoflurane anesthesia (2.5% Isoflurane & 2 μL/min oxygen for induction; 2% isoflurane & 1 μL/min oxygen for echography), cardiac function was recorded using a VEVO 2100 Imaging System and a MS400 transducer appropriate for mouse cardiovascular imaging (18-38 MHz) (VisualSonics, Canada). Data were analyzed using the cardiac package in VEVO-Lab (VisualSonics, Canada). Left ventricular end-diastolic volume (EDV) and end-systolic volume (ESV) were calculated on cine-loops using the 2-dimensional area-length method, allowing the calculation of left ventricular ejection fraction (EF) as EF (%)=[(EDV−ESV)/EDV]×100.

Histopathological Analyses

Cardiac remodeling following MI was assessed at day 21. Hearts were harvested, rinsed in PBS; atria and right ventricle were excised and the remaining left ventricle (LV) was embedded in Tissue-TEK O.C.T. compound (Sakura) and frozen in liquid nitrogen-cooled isopentane and stored at −80° C. Hearts were cut along their length into 8 m thick cardiac muscle cryosections (CM 3050S, Leica). Serial sections were mounted on microscope slides, each section being spaced from the next one by 500 m. In this way, 8 cuts allowed entire LV tissue analysis. Masson's trichrome and Sirius Red staining were performed for infarct size and interstitial fibrosis evaluation, respectively. Infarct size was calculated as a percentage of infarct area to total LV area. The collagen volume fraction was calculated as the ratio of the total area of interstitial fibrosis to the total cardiac area in the entire visual field of the section.

Results

In order to evaluate the effect of the anti-CD8α antibody of the invention on myocardial infarction, the anti-CD8α antibody clone MP08-R3-F08 was injected into transgenic mice expressing human CD8α one hour after induction of myocardial infarction.

First, depletion of hCD8+ cells in the blood and spleen of hCD8α-expressing transgenic mice which received either saline solution (control) or the anti-CD8α antibody clone MP08-R3-F08 was assessed, 3 days after induction of myocardial infarction and injection of saline solution or anti-CD8α antibody clone MP08-R3-F08.

As shown on FIG. 12A-C and FIG. 13A-C depletion of CD45+hCD8α+ cells is total in the blood of mice treated with the anti-CD8α antibody clone MP08-R3-F08 (FIGS. 12B & C) as compared to control mice (FIGS. 12A & C), while there is more than 90% depletion in the spleen of mice treated with the anti-CD8α antibody clone MP08-R3-F08 (FIGS. 13B & C) as compared to control mice (FIGS. 13A & C).

In addition, 3 days after induction of myocardial infarction and injection of saline solution or anti-CD8α antibody clone MP08-R3-F08, hearts were harvested from the mice, sectioned and stained with 2,3,5-triphenyltetrazolium chloride (TTC) in order to measure the necrosis induced after myocardial infarction.

As shown of FIG. 14, there is a significant 20% decrease in necrosis area in transgenic mice treated with the anti-CD8α antibody clone MP08-R3-F08, as compared to control transgenic mice treated with saline solution.

Conclusion

These results show that the anti-CD8α antibody clone MP08-R3-F08 possess a strong specificity for its target CD8α isoform 2 (both secreted form and tethered secreted form). Additionally, the anti-CD8α antibody clone MP08-R3-F08 does not exhibit any off-target binding.

Furthermore, all three anti-CD8α antibody clones (i.e., MP08-R3-F08, MP08-R3-C11 and MP09-R3-D03) are capable of depleting CD8α-expressing cells in vivo in non-human primates. All anti-CD8α antibody clones (i.e., MP08-R3-F08, MP08-R3-C11 and MP09-R3-D03) induce a strong or even complete depletion of CD8α-expressing cells within 1 hour after antibody injection in non-human primates. Moreover, depletion is total for the anti-CD8α antibody clone MP08-R3-F08 for at least 14 days. 14 days post-depletion, repopulation of the CD8α-expressing cells begins slowly and progressively at the 7.5 mg/kg bodyweight dose, and reaches only 2.5% at day 62 post-injection. Thus, depletion of CD8α-expressing cells by the anti-CD8α antibodies of the invention is fast, strong if not complete, and transient. Repopulation of CD8α-expressing cells after depletion is slow and progressive.

Moreover, the anti-CD8α antibody clone MP08-R3-F08 is able to limit the necrosis area induced after myocardial infarction in hCD8α-expressing transgenic mice.

Taken together, these results indicate that the anti-CD8α antibodies as described herein could be valuable therapeutic tools for transiently depleting CD8α-expressing cells in a controlled manner and for the treatment of cardiovascular diseases such as myocardial infarction.

The invention claimed is:

1. An isolated anti-CD8α antibody, or an antigen-binding fragment thereof, wherein:

a) the variable region of the heavy chain (VH) of said isolated anti-CD8α antibody, or antigen-binding fragment thereof, comprises the three following CDRs:

$V_H$-CDR1: $NX_1X_2MN$, wherein
$X_1$ is N or Y,
$X_2$ is D or A or Y,
$V_H$-CDR2: $X_3ISGSSX_4YIX_5YADFVKG$ (SEQ ID NO: 1), wherein
$X_3$ is D or S,
$X_4$ is S or R,
$X_5$ is D or G or Y,
$V_H$-CDR3: $SSX_6X_7X_8X_9YX_{10}X_{11}X_{12}X_{13}MDV$ (SEQ ID NO: 2), wherein
$X_6$ is N or no amino acid,
$X_7$ is Y or no amino acid,
$X_8$ is Y or G or no amino acid,
$X_9$ is D or S or no amino acid,
$X_{10}$ is S or N or F,
$X_1$ is A or G,
$X_{12}$ is S or D or N,
$X_{13}$ is A or G; and b) the variable region of the light chain (VL) of said isolated anti-CD8α antibody, or antigen-binding fragment thereof, comprises the three following CDRs:

$V_L$-CDR1: $AGTSSDVGGX_{14}X_{15}X_{16}VS$ (SEQ ID NO: 3), wherein
$X_{14}$ is G or N or Y,
$X_{15}$ is S or Y,
$X_{16}$ is S or Y,
$V_L$-CDR2: $X_{17}DSX_{18}RPS$ (SEQ ID NO: 4), wherein
$X_{17}$ is Q or S or Y,
$X_{18}$ is Y or S,
$V_L$-CDR3: $SSX_{19}TX_{20}YSTRV$ (SEQ ID NO: 5), wherein
$X_{19}$ is Y or D,
$X_{20}$ is Y or Q or S.

2. The isolated anti-CD8α antibody, or antigen-binding fragment thereof, according to claim 1, wherein:

a) the VH of said isolated anti-CD8α antibody, or antigen-binding fragment thereof, comprises the three following CDRs:

$V_H$-CDR1:
(SEQ ID NO: 6)
NNAMN,
(SEQ ID NO: 12)
NYDMN,
or
(SEQ ID NO: 18)
NYYMN;

-continued $V_H$-CDR2:
(SEQ ID NO: 7)
DISGSSRYIGYADFVKG,
(SEQ ID NO: 13)
DISGSSSYIDYADFVKG,
or
(SEQ ID NO: 19)
SISGSSRYIYYADFVKG;

$V_H$-CDR3:
(SEQ ID NO: 8)
SSNYYDYNADAMDV,
(SEQ ID NO: 14)
SSYYSGSGMDV,
or
(SEQ ID NO: 20)
SSGSYFGNAMDV;

b) the VL of said isolated anti-CD8α antibody, or antigen-binding fragment thereof, comprises the three following CDRs:

$V_L$-CDR1:
(SEQ ID NO: 9)
AGTSSDVGGNSYVS,
(SEQ ID NO: 15)
AGTSSDVGGGSSVS,
or
(SEQ ID NO: 21)
AGTSSDVGGYYSVS;

$V_L$-CDR2:
(SEQ ID NO: 10)
SDSSRPS,
(SEQ ID NO: 16)
QDSYRPS,
or
(SEQ ID NO: 22)
YDSSRPS $V_L$-CDR3:
(SEQ ID NO: 11)
SSYTQYSTRV,
(SEQ ID NO: 17)
SSYTYYSTRV,
or
(SEQ ID NO: 23)
SSDTSYSTRV.

3. The isolated anti-CD8α antibody, or antigen-binding fragment thereof, according to claim 1, wherein said isolated anti-CD8α antibody, or antigen-binding fragment thereof, comprises the six following CDRs:

$V_H$-CDR1: (SEQ ID NO: 6)

NNAMN, $V_H$-CDR2: (SEQ ID NO: 7)

DISGSSRYIGYADFVKG, $V_H$-CDR3: (SEQ ID NO: 8)

SSNYYDYNADAMDV, $V_L$-CDR1: (SEQ ID NO: 9)

AGTSSDVGGNSYVS, $V_L$-CDR2: (SEQ ID NO: 10)

SDSSRPS,
and $V_L$-CDR3: (SEQ ID NO: 11)

SSYTQYSTRV;
or $V_H$-CDR1: (SEQ ID NO: 12)

NYDMN, $V_H$-CDR2: (SEQ ID NO: 13)

DISGSSSYIDYADFVKG, $V_H$-CDR3: (SEQ ID NO: 14)

SSYYSGSGMDV, $V_L$-CDR1: (SEQ ID NO: 15)

AGTSSDVGGGSSVS, $V_L$-CDR2: (SEQ ID NO: 16)

QDSYRPS,
and $V_L$-CDR3: (SEQ ID NO: 17)

SSYTYYSTRV;
or $V_H$-CDR1: (SEQ ID NO: 18)

NYYMN, $V_H$-CDR2: (SEQ ID NO: 19)

SISGSSRYIYYADFVKG, $V_H$-CDR3: (SEQ ID NO: 20)

SSGSYFGNAMDV, $V_L$-CDR1: (SEQ ID NO: 21)

AGTSSDVGGYYSVS, $V_L$-CDR2: (SEQ ID NO: 22)

YDSSRPS,
and

-continued $V_L$-CDR3: (SEQ ID NO: 23)

SSDTSYSTRV.

4. The isolated anti-CD8α antibody, or antigen-binding fragment thereof, according to claim 1, wherein said isolated anti-CD8α antibody, or antigen-binding fragment thereof, comprises a variable region of the heavy chain (VH) comprising a sequence as set forth in SEQ ID NO: 24, SEQ ID NO: 26, or SEQ ID NO: 28, or a sequence having at least 80% identity with SEQ ID NO: 24, SEQ ID NO: 26, or SEQ ID NO: 28.

5. The isolated anti-CD8α antibody, or antigen-binding fragment thereof, according to claim 1, wherein said isolated anti-CD8α antibody, or antigen-binding fragment thereof, comprises a variable region of the light chain (VL) comprising a sequence as set forth in SEQ ID NO: 25, SEQ ID NO: 27, or SEQ ID NO: 29, or a sequence having at least 80% identity with SEQ ID NO: 25, SEQ ID NO: 27, or SEQ ID NO: 29.

6. The isolated anti-CD8α antibody, or antigen-binding fragment thereof, according to claim 1, wherein said isolated anti-CD8α antibody, or antigen-binding fragment thereof, comprises:

a VH comprising a sequence as set forth in SEQ ID NO: 24, or a sequence having at least 80% identity with SEQ ID NO: 24, and a VL comprising a sequence as set forth in SEQ ID NO: 25, or a sequence having at least 80% identity with SEQ ID NO: 25; or a VH comprising a sequence as set forth in SEQ ID NO: 26, or a sequence having at least 80% identity with SEQ ID NO: 26, and a VL comprising a sequence as set forth in SEQ ID NO: 27, or a sequence having at least 80% identity with SEQ ID NO: 27; or a VH comprising a sequence as set forth in SEQ ID NO: 28, or a sequence having at least 80% identity with SEQ ID NO: 28, and a VL comprising a sequence as set forth in SEQ ID NO: 29, or a sequence having at least 80% identity with SEQ ID NO: 29.

7. The isolated anti-CD8α antibody, or antigen-binding fragment thereof, according to claim 1, wherein said isolated anti-CD8α antibody, or antigen-binding fragment thereof, is a CD8α-expressing cell depleting antibody.

8. A fusion protein comprising the anti-CD8α antibody, or antigen-binding fragment thereof, according to claim 1.

9. A pharmaceutical composition comprising the isolated anti-CD8α antibody, or antigen-binding fragment thereof, according to claim 1, and at least one pharmaceutically acceptable excipient.

10. A method for treating a CD8-related disease in a subject in need thereof, said method comprising administering to the subject at least one isolated anti-CD8α antibody, or antigen-binding fragment thereof, according to claim 1.

11. The method according to claim 10, wherein said CD8-related disease is a cardiovascular disease.

12. An in vitro method for depleting CD8α-expressing cells in a sample, comprising a step of contacting said sample with the isolated anti-CD8α antibody, or antigen-binding fragment thereof, according to claim 1.

13. An in vitro method for detecting and/or quantifying CD8α in a sample, cell, tissue or organ, comprising contacting said sample, cell, tissue or organ with the isolated anti-CD8α antibody, or antigen-binding fragment thereof, according to claim 1.

* * * * *

SEQUENCE LISTING

```
Sequence total quantity: 36
SEQ ID NO: 1            moltype = AA  length = 17
FEATURE                 Location/Qualifiers
source                  1..17
                        mol_type = protein
                        organism = synthetic construct
VARIANT                 1
                        note = X is D or S
VARIANT                 7
                        note = X is S or R
VARIANT                 10
                        note = X is D or G or Y
SEQUENCE: 1
XISGSSXYIX YADFVKG                                               17

SEQ ID NO: 2            moltype = AA  length = 14
FEATURE                 Location/Qualifiers
source                  1..14
                        mol_type = protein
                        organism = synthetic construct
VARIANT                 3
                        note = X is N or no amino acid
VARIANT                 4
                        note = X is Y or no amino acid
VARIANT                 5
                        note = X is Y or G or no amino acid
VARIANT                 6
                        note = X is D or S or no amino acid
VARIANT                 8
                        note = X is S or N or F
VARIANT                 9
                        note = X is A or G
VARIANT                 10
                        note = X is S or D or N
VARIANT                 11
                        note = X is A or G
SEQUENCE: 2
SSXXXXYXXX XMDV                                                  14
```

-continued

```
SEQ ID NO: 3            moltype = AA  length = 14
FEATURE                 Location/Qualifiers
source                  1..14
                        mol_type = protein
                        organism = synthetic construct
VARIANT                 10
                        note = X is G or N or Y
VARIANT                 11
                        note = X is S or Y
VARIANT                 12
                        note = X is S or Y
SEQUENCE: 3
AGTSSDVGGX XXVS                                                    14

SEQ ID NO: 4            moltype = AA  length = 7
FEATURE                 Location/Qualifiers
source                  1..7
                        mol_type = protein
                        organism = synthetic construct
VARIANT                 1
                        note = X is Q or S or Y
VARIANT                 4
                        note = X is Y or S
SEQUENCE: 4
XDSXRPS                                                            7

SEQ ID NO: 5            moltype = AA  length = 10
FEATURE                 Location/Qualifiers
source                  1..10
                        mol_type = protein
                        organism = synthetic construct
VARIANT                 3
                        note = X is Y or D
VARIANT                 5
                        note = X is Y or Q or S
SEQUENCE: 5
SSXTXYSTRV                                                         10

SEQ ID NO: 6            moltype = AA  length = 5
FEATURE                 Location/Qualifiers
source                  1..5
                        mol_type = protein
                        organism = synthetic construct
SEQUENCE: 6
NNAMN                                                              5

SEQ ID NO: 7            moltype = AA  length = 17
FEATURE                 Location/Qualifiers
source                  1..17
                        mol_type = protein
                        organism = synthetic construct
SEQUENCE: 7
DISGSSRYIG YADFVKG                                                 17

SEQ ID NO: 8            moltype = AA  length = 14
FEATURE                 Location/Qualifiers
source                  1..14
                        mol_type = protein
                        organism = synthetic construct
SEQUENCE: 8
SSNYYDYNAD AMDV                                                    14

SEQ ID NO: 9            moltype = AA  length = 14
FEATURE                 Location/Qualifiers
source                  1..14
                        mol_type = protein
                        organism = synthetic construct
SEQUENCE: 9
AGTSSDVGGN SYVS                                                    14

SEQ ID NO: 10           moltype = AA  length = 7
FEATURE                 Location/Qualifiers
source                  1..7
                        mol_type = protein
                        organism = synthetic construct
SEQUENCE: 10
SDSSRPS                                                            7

SEQ ID NO: 11           moltype = AA  length = 10
```

-continued

```
FEATURE               Location/Qualifiers
source                1..10
                      mol_type = protein
                      organism = synthetic construct
SEQUENCE: 11
SSYTQYSTRV                                                    10

SEQ ID NO: 12         moltype = AA  length = 5
FEATURE               Location/Qualifiers
source                1..5
                      mol_type = protein
                      organism = synthetic construct
SEQUENCE: 12
NYDMN                                                         5

SEQ ID NO: 13         moltype = AA  length = 17
FEATURE               Location/Qualifiers
source                1..17
                      mol_type = protein
                      organism = synthetic construct
SEQUENCE: 13
DISGSSSYID YADFVKG                                            17

SEQ ID NO: 14         moltype = AA  length = 11
FEATURE               Location/Qualifiers
source                1..11
                      mol_type = protein
                      organism = synthetic construct
SEQUENCE: 14
SSYYSGSGMD V                                                  11

SEQ ID NO: 15         moltype = AA  length = 14
FEATURE               Location/Qualifiers
source                1..14
                      mol_type = protein
                      organism = synthetic construct
SEQUENCE: 15
AGTSSDVGGG SSVS                                               14

SEQ ID NO: 16         moltype = AA  length = 7
FEATURE               Location/Qualifiers
source                1..7
                      mol_type = protein
                      organism = synthetic construct
SEQUENCE: 16
QDSYRPS                                                       7

SEQ ID NO: 17         moltype = AA  length = 10
FEATURE               Location/Qualifiers
source                1..10
                      mol_type = protein
                      organism = synthetic construct
SEQUENCE: 17
SSYTYYSTRV                                                    10

SEQ ID NO: 18         moltype = AA  length = 5
FEATURE               Location/Qualifiers
source                1..5
                      mol_type = protein
                      organism = synthetic construct
SEQUENCE: 18
NYYMN                                                         5

SEQ ID NO: 19         moltype = AA  length = 17
FEATURE               Location/Qualifiers
source                1..17
                      mol_type = protein
                      organism = synthetic construct
SEQUENCE: 19
SISGSSRYIY YADFVKG                                            17

SEQ ID NO: 20         moltype = AA  length = 12
FEATURE               Location/Qualifiers
source                1..12
                      mol_type = protein
                      organism = synthetic construct
SEQUENCE: 20
SSGSYFGNAM DV                                                 12
```

```
SEQ ID NO: 21           moltype = AA  length = 14
FEATURE                 Location/Qualifiers
source                  1..14
                        mol_type = protein
                        organism = synthetic construct
SEQUENCE: 21
AGTSSDVGGY YSVS                                                    14

SEQ ID NO: 22           moltype = AA  length = 7
FEATURE                 Location/Qualifiers
source                  1..7
                        mol_type = protein
                        organism = synthetic construct
SEQUENCE: 22
YDSSRPS                                                            7

SEQ ID NO: 23           moltype = AA  length = 10
FEATURE                 Location/Qualifiers
source                  1..10
                        mol_type = protein
                        organism = synthetic construct
SEQUENCE: 23
SSDTSYSTRV                                                         10

SEQ ID NO: 24           moltype = AA  length = 123
FEATURE                 Location/Qualifiers
source                  1..123
                        mol_type = protein
                        organism = synthetic construct
SEQUENCE: 24
EVQLVESGGS LVKPGGSLRL SCAASGFTFS NNAMNWVRQA PGKGLEWISD ISGSSRYIGY  60
ADFVKGRFTI SRDNAKNSLY LQMNSLRAED TAVYYCVRSS NYYDYNADAM DVWGRGTLVT  120
VSS                                                                123

SEQ ID NO: 25           moltype = AA  length = 110
FEATURE                 Location/Qualifiers
source                  1..110
                        mol_type = protein
                        organism = synthetic construct
SEQUENCE: 25
QSVLTQPASV SGSPGQSITI SCAGTSSDVG GNSYVSWYQQ HPGKAPKLMI YSDSSRPSGV  60
SNRFSGSKSG NTASLTISGL QAEDEADYYC SSYTQYSTRV FGGGTKLAVL             110

SEQ ID NO: 26           moltype = AA  length = 120
FEATURE                 Location/Qualifiers
source                  1..120
                        mol_type = protein
                        organism = synthetic construct
SEQUENCE: 26
EVQLVESGGS LVKPGGSLRL SCAASGFTFS NYDMNWVRQA PGKGLEWISD ISGSSSYIDY  60
ADFVKGRFTI SRDNAKNSLY LQMNSLRAED TAVYYCVRSS YYSGSGMDVW GRGTLVTVSS  120

SEQ ID NO: 27           moltype = AA  length = 110
FEATURE                 Location/Qualifiers
source                  1..110
                        mol_type = protein
                        organism = synthetic construct
SEQUENCE: 27
QSVLTQPASV SGSPGQSITI SCAGTSSDVG GGSSVSWYQQ HPGKAPKLMI YQDSYRPSGV  60
SNRFSGSKSG NTASLTISGL QAEDEADYYC SSYTYYSTRV FGGGTKLAVL             110

SEQ ID NO: 28           moltype = AA  length = 121
FEATURE                 Location/Qualifiers
source                  1..121
                        mol_type = protein
                        organism = synthetic construct
SEQUENCE: 28
EVQLVESGGS LVKPGGSLRL SCAASGFTFS NYYMNWVRQA PGKGLEWISS ISGSSRYIYY  60
ADFVKGRFTI SRDNAKNSLY LQMNSLRAED TAVYYCVRSS GSYFGNAMDV WGRGTLVTVS  120
S                                                                  121

SEQ ID NO: 29           moltype = AA  length = 110
FEATURE                 Location/Qualifiers
source                  1..110
                        mol_type = protein
                        organism = synthetic construct
SEQUENCE: 29
QSVLTQPASV SGSPGQSITI SCAGTSSDVG GYYSVSWYQQ HPGKAPKLMI YYDSSRPSGV  60
SNRFSGSKSG NTASLTISGL QAEDEADYYC SSDTSYSTRV FGGGTKLAVL             110
```

```
SEQ ID NO: 30          moltype = AA  length = 235
FEATURE                Location/Qualifiers
source                 1..235
                       mol_type = protein
                       organism = Homo sapiens
SEQUENCE: 30
MALPVTALLL PLALLLHAAR PSQFRVSPLD RTWNLGETVE LKCQVLLSNP TSGCSWLFQP  60
RGAAASPTFL LYLSQNKPKA AEGLDTQRFS GKRLGDTFVL TLSDFRRENE GYYFCSALSN  120
SIMYFSHFVP VFLPAKPTTT PAPRPPTPAP TIASQPLSLR PEACRPAAGG AVHTRGLDFA  180
CDIYIWAPLA GTCGVLLLSL VITLYCNHRN RRRVCKCPRP VVKSGDKPSL SARYV       235

SEQ ID NO: 31          moltype = DNA  length = 1461
FEATURE                Location/Qualifiers
source                 1..1461
                       mol_type = other DNA
                       organism = synthetic construct
SEQUENCE: 31
gcggccgcaa actacaagac agacttgcaa aagaaggcat gcacagctca gcactgctct  60
gttgcctggt cctcctgact ggggtgaggg ccgaggtgca gctggtggag agcgggggca  120
gcctggtgaa gccaggggga agcctgaggc tgagctgtgc cgcatccggg tttacatttt  180
ccaacaacgc catgaactgg gtgaggcagg cacccggcaa agggctggag tggatttcag  240
acatttccgg cagtagcaga tacatcggct acgccgactt cgtgaagggc aggttcacaa  300
tcagcagaga caacgctaag aacagcctgt acctgcagat gaactccctg agggccgagg  360
acacagccgt gtactactgc gtgaggagct ccaactacta tgactacaac gccgacgcta  420
tggatgtgtg gggaaggggc accctggtga ccgtgagctc cgctagcacc aagggcccat  480
cggtcttccc cctggcaccc tcctccaaga gcacctctgg gggcacagcg gccctgggct  540
gcctggtcaa ggactacttc cccgaaccgg tgacggtgtc gtggaactca ggcgccctga  600
ccagcggcgt gcacaccttc ccggctgtcc tacagtcctc aggactctac tccctcagca  660
gcgtggtgac cgtgccctcc agcagcttgg gcacccagac ctacatctgc aacgtgaatc  720
acaagcccag caacaccaag gtggacaaga aagttgagcc caaatcttgt gacaaaactc  780
acacatgccc accgtgccca gcacctgaac tcctgggggg accgtcagtc ttcctcttcc  840
ccccaaaacc caaggacacc ctcatgatct cccggacccc cgaggtcaca tgcgtggtgg  900
tggacgtgag ccacgaagac cctgaggtca agttcaactg gtacgtggac ggcgtggagg  960
tgcataatgc caagacaaag ccgcgggagg agcagtacaa cagcacgtac cgtgtggtca  1020
gcgtcctcac cgtcctgcac caggactggc tgaatggcaa ggagtacaag tgcaaggtct  1080
ccaacaaagc cctcccagcc cccatcgaga aaaccatctc caaagccaaa gggcagcccc  1140
gagaaccaca ggtgtacacc ctgcccccat cccgggagga gatgaccaag aaccaggtca  1200
gcctgacctg cctggtcaaa ggcttctatc ccagcgacat cgccgtggag tgggagagca  1260
atgggcagcc ggagaacaac tacaagacca cgcctcccgt gctggactcc gacggctcct  1320
tcttcctcta cagcaagctc accgtggaca agagcaggtg gcagcagggg aacgtcttct  1380
catgctccgt gatgcatgag gctctgcaca accactacac gcagaagagc ctctccctgt  1440
ctccgggtaa atgattctag a                                            1461

SEQ ID NO: 32          moltype = DNA  length = 750
FEATURE                Location/Qualifiers
source                 1..750
                       mol_type = other DNA
                       organism = synthetic construct
SEQUENCE: 32
gcggccgcaa actacaagac agacttgcaa aagaaggcat gcacagctca gcactgctct  60
gttgcctggt cctcctgact ggggtgaggg cccagtccgt gctgacccag cccgcctccg  120
tgtccggaag cccaggacag tccatcacca tctcctgcgc cggcacctcc tccgacgtgg  180
gaggaaacag ctacgtgtcc tggtatcaac agcaccccgg caaagcaccc aaactgatga  240
tctactccga cagttcccgc ccctccggcg tgtccaacag gttcagcggc tccaagagcg  300
gcaacaccgc ctccctgact atctccggcc tgcaggctga agacgaagcc gactactact  360
gctcctccta cacccagtac tccacccgcg tgttcggcgg cggcaccaaa ctggccgtgc  420
tgggtcagcc caaggccaac cccactgtca ctctgttccc gccctcctct gaggagctcc  480
aagccaacaa ggccacacta gtgtgtctga tcagtgactt ctacccggga gctgtgacag  540
tggcctggaa ggcagatggc agccccgtca aggcgggagt ggagaccacc aaaccctcca  600
aacagagcaa caacaagtac gcggccagca gctacctgag cctgacgccc gagcagtgga  660
agtcccacag aagctacagc tgccaggtca cgcatgaagg gagcaccgtg gagaagacag  720
tggcccctac agaatgttca tgattctaga                                   750

SEQ ID NO: 33          moltype = DNA  length = 1452
FEATURE                Location/Qualifiers
source                 1..1452
                       mol_type = other DNA
                       organism = synthetic construct
SEQUENCE: 33
gcggccgcaa actacaagac agacttgcaa aagaaggcat gcacagctca gcactgctct  60
gttgcctggt cctcctgact ggggtgaggg ccgaggtgca gctggtggag agcgggggca  120
gcctggtgaa gccaggggga agcctgaggc tgagctgtgc cgcatccggg tttacatttt  180
ccaactacga catgaactgg gtgaggcagg cccccggcaa aggactggag tggatttcag  240
acatctccgg cagcagttcc tacatcgact acgctgattt tgtgaagggc aggttcacaa  300
tctcccggga caacgctaag aactccctgt acctgcagat gaacagtctg agggccgagg  360
acaccgctgt gtactactgc gtgaggtcct cctactatag tggcagcggc atggacgtgt  420
ggggccgggg aaccctggtg accgtgtcct ctgctagcac caagggccca tcggtcttcc  480
ccctggcacc ctcctccaag agcacctctg ggggcacagc ggccctgggc tgcctggtca  540
```

```
aggactactt ccccgaaccg gtgacggtgt cgtggaactc aggcgccctg accagcggcg  600
tgcacacctt cccggctgtc ctacagtcct caggactcta ctccctcagc agcgtggtga  660
ccgtgccctc cagcagcttg ggcacccaga cctacatctg caacgtgaat cacaagccca  720
gcaacaccaa ggtggacaag aaagttgagc ccaaatcttg tgacaaaact cacacatgcc  780
caccgtgccc agcacctgaa ctcctggggg gaccgtcagt cttcctcttc cccccaaaac  840
ccaaggacac cctcatgatc tcccggaccc ccgaggtcac atgcgtggtg gtggacgtga  900
gccacgaaga ccctgaggtc aagttcaact ggtacgtgga cggcgtggag gtgcataatg  960
ccaagacaaa gccgcgggag gagcagtaca acagcacgta ccgtgtggtc agcgtcctca  1020
ccgtcctgca ccaggactgg ctgaatggca aggagtacaa gtgcaaggtc tccaacaaag  1080
ccctcccagc ccccatcgag aaaaccatct ccaaagccaa agggcagccc cgagaaccac  1140
aggtgtacac cctgccccca tcccgggagg agatgaccaa gaaccaggtc agcctgacct  1200
gcctggtcaa aggcttctat cccagcgaca tcgccgtgga gtgggagagc aatgggcagc  1260
cggagaacaa ctacaagacc acgcctcccg tgctggactc cgacggctcc ttcttcctct  1320
acagcaagct caccgtggac aagagcaggt ggcagcaggg gaacgtcttc tcatgctccg  1380
tgatgcatga ggctctgcac aaccactaca cgcagaagag cctctccctg tctccgggta  1440
aatgattcta ga                                                      1452

SEQ ID NO: 34           moltype = DNA  length = 750
FEATURE                 Location/Qualifiers
source                  1..750
                        mol_type = other DNA
                        organism = synthetic construct
SEQUENCE: 34
gcggccgcaa actacaagac agacttgcaa aagaaggcat gcacagctca gcactgctct  60
gttgcctggt cctcctgact ggggtgaggg cccagtccgt gctgacccag cccgcctccg  120
tgtccggaag cccaggacag tccatcacca tctcctgcgc cggcacctcc tccgacgtgg  180
gaggaggaag ctccgtgagc tggtatcaac agcaccccgg caaagcaccc aaactgatga  240
tctaccagga cagctacagg ccctccggcg tgtccaacag gttcagcggc tccaagagcg  300
gaaacacagc ctctctgacc atctccggcc tgcaggctga ggacgaagcc gactactact  360
gctcatccta cacttactat tccaccaggg tgttcggagg cggaacaaaa ctggccgtgc  420
tgggtcagcc caaggccaac cccactgtca ctctgttccc gccctcctct gaggagctcc  480
aagccaacaa ggccacacta gtgtgtctga tcagtgactt ctacccggga gctgtgacag  540
tggcctggaa ggcagatggc agccccgtca aggcgggagt ggagaccacc aaaccctcca  600
aacagagcaa caacaagtac gcggccagca gctacctgag cctgacgccc gagcagtgga  660
agtcccacag aagctacagc tgccaggtca cgcatgaagg gagcaccgtg gagaagacag  720
tggcccctac agaatgttca tgattctaga                                  750

SEQ ID NO: 35           moltype = DNA  length = 1455
FEATURE                 Location/Qualifiers
source                  1..1455
                        mol_type = other DNA
                        organism = synthetic construct
SEQUENCE: 35
gcggccgcaa actacaagac agacttgcaa aagaaggcat gcacagctca gcactgctct  60
gttgcctggt cctcctgact ggggtgaggg ccgaggtgca gctggtggag agcgggggca  120
gcctggtgaa gccaggggga agcctgaggc tgagctgtgc cgcatccggg tttacatttt  180
ccaactacta tatgaactgg gtgaggcagg cccctggcaa gggcctggag tggatttcat  240
ctatctccgg cagtagtcga tacatctact acgctgactt tgtgaagggc cggttcacca  300
tctccaggga caacgctaag aactccctgt atctgcagat gaactccctg cgcgccgagg  360
acaccgccgt gtactactgc gtgcgctcct ccggcagcta cttcggaaat gctatggatg  420
tgtgggggag ggggaccctg gtgaccgtgt cctccgctag caccaagggc ccatcggtct  480
tcccccctggc accctcctcc aagagcacct ctgggggcac agcggccctg ggctgcctgg  540
tcaaggacta cttccccgaa ccggtgacgg tgtcgtggaa ctcaggcgcc ctgaccagcg  600
gcgtgcacac cttcccggct gtcctacagt cctcaggact ctactccctc agcagcgtgg  660
tgaccgtgcc ctccagcagc ttgggcaccc agacctacat ctgcaacgtg aatcacaagc  720
ccagcaacac caaggtggac aagaaagttg agcccaaatc ttgtgacaaa actcacacat  780
gcccaccgtg cccagcacct gaactcctgg ggggaccgtc agtcttcctc ttccccccaa  840
aacccaagga caccctcatg atctcccgga cccccgaggt cacatgcgtg gtggtggacg  900
tgagccacga agaccctgag gtcaagttca actggtacgt ggacggcgtg gaggtgcata  960
atgccaagac aaagccgcgg gaggagcagt acaacagcac gtaccgtgtg gtcagcgtcc  1020
tcaccgtcct gcaccaggac tggctgaatg gcaaggagta caagtgcaag gtctccaaca  1080
aagccctccc agcccccatc gagaaaacca tctccaaagc caaagggcag ccccgagaac  1140
cacaggtgta caccctgccc ccatcccggg aggagatgac caagaaccag gtcagcctga  1200
cctgcctggt caaaggcttc tatcccagcg acatcgccgt ggagtgggag agcaatgggc  1260
agccggagaa caactacaag accacgcctc ccgtgctgga ctccgacggc tccttcttcc  1320
tctacagcaa gctcaccgtg gacaagagca ggtggcagca ggggaacgtc ttctcatgct  1380
ccgtgatgca tgaggctctg cacaaccact acacgcagaa gagcctctcc ctgtctccgg  1440
gtaaatgatt ctaga                                                   1455

SEQ ID NO: 36           moltype = DNA  length = 750
FEATURE                 Location/Qualifiers
source                  1..750
                        mol_type = other DNA
                        organism = synthetic construct
SEQUENCE: 36
gcggccgcaa actacaagac agacttgcaa aagaaggcat gcacagctca gcactgctct  60
gttgcctggt cctcctgact ggggtgaggg cccagtccgt gctgacccag cccgcctccg  120
tgtccggaag cccaggacag tccatcacca tctcctgcgc cggcacctcc tccgacgtgg  180
gaggatacta ctccgtgagc tggtatcaac agcaccccgg caaagccccc aaactgatga  240
```

-continued

```
tctactacga cagctcccgg ccctccggcg tgtctaacag gttctccggc tccaagagcg  300
gcaacaccgc cagcctgacc atctccggcc tgcaggcaga agacgaggcc gactactact  360
gctcctccga cacctcctac agcaccaggg tgttcggcgg tggcaccaag ctggccgtgc  420
tgggtcagcc caaggccaac cccactgtca ctctgttccc gccctcctct gaggagctcc  480
aagccaacaa ggccacacta gtgtgtctga tcagtgactt ctacccggga gctgtgacag  540
tggcctggaa ggcagatggc agccccgtca aggcgggagt ggagaccacc aaaccctcca  600
aacagagcaa caacaagtac gcggccagca gctacctgag cctgacgccc gagcagtgga  660
agtcccacag aagctacagc tgccaggtca cgcatgaagg gagcaccgtg gagaagacag  720
tggcccctac agaatgttca tgattctaga                                    750
```